# (12) United States Patent
Yamazaki et al.

(10) Patent No.: US 8,697,742 B2
(45) Date of Patent: Apr. 15, 2014

(54) BCRP/ABCG2 INHIBITOR

(75) Inventors: Ryuta Yamazaki, Minato-ku (JP); Yukiko Nishiyama, Minato-ku (JP); Tomio Furuta, Minato-ku (JP); Takeshi Matsuzaki, Minato-ku (JP); Hiroshi Hatano, Minato-ku (JP); Oh Yoshida, Minato-ku (JP); Masato Nagaoka, Minato-ku (JP); Ritsuo Aiyama, Minato-ku (JP); Shusuke Hashimoto, Minato-ku (JP); Yoshikazu Sugimoto, Kashiwa (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 1184 days.

(21) Appl. No.: 11/909,805

(22) PCT Filed: Mar. 29, 2006

(86) PCT No.: PCT/JP2006/306560
§ 371 (c)(1),
(2), (4) Date: Sep. 27, 2007

(87) PCT Pub. No.: WO2006/106778
PCT Pub. Date: Oct. 12, 2006

(65) Prior Publication Data
US 2009/0253656 A1 Oct. 8, 2009

(30) Foreign Application Priority Data
Mar. 30, 2005 (JP) .................. 2005-097661

(51) Int. Cl.
*A01N 43/06* (2006.01)
*A61K 31/38* (2006.01)
*A01N 43/40* (2006.01)
*A61K 31/435* (2006.01)
*C07D 333/02* (2006.01)
*C07D 487/00* (2006.01)

(52) U.S. Cl.
USPC .................. 514/438; 514/277; 549/29; 532/1

(58) Field of Classification Search
None
See application file for complete search history.

(56) References Cited

U.S. PATENT DOCUMENTS

| 5,589,506 A | 12/1996 | Hashimoto et al. |
| 5,710,164 A * | 1/1998 | Elokdah et al. ............... 514/300 |
| 2003/0125265 A1 | 7/2003 | Hung et al. |
| 2006/0128636 A1 | 6/2006 | Yamazaki et al. |
| 2006/0135445 A1 | 6/2006 | Yamazaki et al. |

FOREIGN PATENT DOCUMENTS

| EP | 0 640 586 A1 | 3/1995 |
| EP | 1 591 112 A1 | 11/2005 |
| EP | 1 591 117 A1 | 11/2005 |
| JP | 05-506857 | 10/1993 |
| JP | 6-316543 | 11/1994 |
| JP | 7-48336 | 2/1995 |
| JP | 9-500386 | 1/1997 |
| JP | 11-506754 | 6/1999 |
| WO | WO91/16051 | * 10/1991 |
| WO | WO 94/20456 | 9/1994 |
| WO | WO 96/39387 | 12/1996 |
| WO | 99/40056 | 8/1999 |
| WO | 2004/069233 | 8/2004 |
| WO | 2004/069243 | 8/2004 |

OTHER PUBLICATIONS

Xu et al. (Annals of Oncology,vol. 13, pp. 1841-1851; 2002).*
Scheffer et al. (J Clin Pathol, vol. 55, pp. 332-339; 2002).*
Buu-Hoi, et al., "Thiophen Derivatives of Potential Biological Interest. Part II. Thionaphihen Analogues of Stilbene and Related Compounds.", Journal of the Chemical Society, 1951, pp. 251-255. XP003001224.
Toshiyuki Yoneda, et al., "The Antiproliferative Effects of Tyrosine Kinase Inhibitors Tyrphostins on a Human Squamous Cell Carcinoma in Vitro and in Nude Mice", Cancer Research , vol. 51, Aug. 15, 1991, pp. 4430-4435.
Raymond N. Castle, et al., "The Reaction of Pyridine Aldehydes with Phenylacetonitriles", Journal of Organic Chemistry, vol. 20, 1955, pp. 987-989.
Wakao Sato, et al., "Circumvention of Multidrug Resistance by a Newly Synthesized Quinoline Derivative, MS-073[1]", Cancer Research 51, May 1, 1991, pp. 2420-2424.
Ken-ichi Miyamoto, et al., "Inhibition of Multidrug Resistance by a New Staurosporine Derivative, Na-382, in Vitro and in Vivo[1]", Cancer Research 53, Apr. 1, 1993, pp. 1555-1559.
Michael J. Newman, et al., "Discovery and Characterization of OC144-093, a Novel Inhibitor of P-Glycoprotein-mediated Multidrug Resistance". Cancer Research 60, Jun. 1, 2000, pp. 2964-2972.
John D. Allen, et al., "Multidrug Resistance and Pharmacological Protection Mediated by the Breast Cancer Resistance Protein (BCRP/ABCG2)[1]", Molecular Cancer Therapeutics, vol. 1, Apr. 2002, pp. 427-434.
I. G. Binev, et al., "Nitrile Frequency and Intensity-Structure Relationships of Trans-1,2-Diaryl-Agrylonitriles/ L. F. E. R. and Quantum-Chemical Approaches", Izvestiya po Khimiya, Institute of Organic Chemistry, vol. 12, XP009122581, 1979, pp. 228-246.
Dore, Jean-Christophe et al., "Antitumor chemotherapy and synthesis of natural antitumor agents. VI. Cytotoxic antitumor activity of trans-α-cyanostilbenes in vitro and antitumor activity in vivo against Kreb II ascites carcinoma", Journal de Pharmacie de Belgique, vol. 28, No. 1, pp. 3-23, 1973.
McLeod, H. L. et al., "In vivo pharmacology and anti-tumour evaluation of the tyrphostin tyrosine kinase inhibitor RG13022", British Journal of Cancer, vol. 74, No. 11, pp. 1714-1718, 1996.

(Continued)

*Primary Examiner* — Jeffrey S. Lundgren
*Assistant Examiner* — Michael Schmitt
(74) *Attorney, Agent, or Firm* — Oblon, Spivak, McClelland, Maier & Neustadt, L.L.P.

(57) ABSTRACT

A breast cancer resistance protein (BCRP/ABCG2) inhibitor. The BCRP inhibitor contains, as an active ingredient, an acrylonitrile derivative or a salt thereof.

12 Claims, 2 Drawing Sheets

(56) References Cited

OTHER PUBLICATIONS

Regaila, H.A.A. et al., "Synthesis of some new benzimidazole and N-acetylpyrazoline derivatives", Chemical Abstracts, vol. 92, p. 617, 1980.
Lavagnino, E. R. et al., "Substituted acrylonitriles from heterocycric aldehydes and 3, 4-dimethoxyphenylacetonitrile", Journal of Organic Chemistry, vol. 22, No. 457-458, 1957.
Buu-Hio, N.P. et al., "Thiophene derivatives of potential biological interest. II. Thianaphtene analogs of stilbene and related compounds", Chemical Abstracts, vol. 45, columns 8509 to 8910, 8509, Par. No. {0002}, Lines e to h, 1951.
Cagniant, P. et al., "A few derivatives of 3-(cyanomethyl) thianaphtene and of 3-formylthianaphtene", Chemical Abstracts, vol. 45, col. 8508, Par. No. [0002], Lines a to d, 1951.
Sonar, Vijayakumar N. et al., "(Z)-3-(1H-Indol-3-y1)-2-(3-thienyl)-acrylonitrile and (Z)-3) [1-(4-tert-butylbenzyl)-1H-indol-3-yl]-2-(3-thienyl) acrylonitrile", Acta Crystallographica, Section C:Crystal Structre Communications, vol. C61, No. 2, pp. o78 to o80, 2005.
Sonar, Vijayakumar N., "(Z)-3-(1-Methyl-1H-indol-3-yl)-2-(thiophen-3-yl)acrylonitrile", Acta Crystallographica, Section C: Crystal Structure Communication, vol. C60, No. 3, pp. o217 to o218, 2004.
Carta, Antonio et al., "Synthesis and antiproliferative activity of 3-aryl-2-(1H-benzotriazol-1-yl)acrylonitriles. Part III" European Journal of Medicinal Chemistry, vol. 37, pp. 891-900, 2002.
Bradamante, Silvia et al., "Heterocycles as donor and acceptor units in push-pull conjugated molecules. Part 1", Journal of Physical organic Chemistry, vol. 10, No. 7, pp. 517-524, 1997.
Brunton, Valerie G. et al., "Synthesis and antiproliferative activity of tyrphostins containing quinoline moieties", Anti-Cancer Drug Design, vol. 11, No. 6, pp. 463-483, 1996.
Wilkens, Jochen et al., Hetero-Cope Rearrangements. VI[1]. Short and Stereoselective Synthesis of 2-Vinylindoles by a Tandem-process, Tetrahedron, vol. 43, No. 14, pp. 3237-3246, 1987.
Efremova T.M. et al., "Carbolines. VII. 1-Metyl-4-hetarylmethyl-βcarbolines", Chemical Abstracts, vol. 82, p. 423, 1975.
Borsche, W. et al., "Quinolyl-2-pyroracemic acid and quinolyl-2-acetic acid", Chemical Abstracts, vol. 31, cols. 405 to 406, col. 406, line 41, 1937.
Minot, C., et al., "Photocyclization of stilbenes and related indole compounds: contribution to utilization of reactivity indexes", Tetrahedon vol. 36, pp. 1209-1214, 1980.
Riche, C., et al.,"Rearrangements at the time of photochemical synthesis of indole compounds", Tetrahedron Letters No. 51, pp. 4567-4570, 1975.
Dieng, C., et al., Studies of indole series: VII (1a). Synthesis of new pyridocarbazoles obtained by photocyclization of 1-(β-indolyl)-2-(pyridyl)acrylonitriles (1b-d), Journal of heterocyclic Chem. 12, 3, pp. 455-460, Jun. 1975.
Chemistry, Biochemistry, and Safety of Acrylamide. A Review, Mental Friedman, J. Agric. Food Chem., 2003, 51 (16), pp. 4504-4526, Publication Date (web) : K;u 3, 2003 (Review).
Synthesis, X-ray Crystal Structures, Stabilities, and in Vitro Cytotoxic Activities of New Heteroarylacrylontiriles, Franciszek Saczewski et al., J. Med. Chem., ACS Med. Chem., 2004, 47 (13), pp. 3438-3449, Oybkucatuib Date (web): May 15, 2004 (Article).
Extended European Search Report issued on May 3, 2011 for European Patent Application No. 11000788.7.
W. Borsche and R. Manteuffel: "Über Chinolyl-2-brentzraubensaure and Chinolyl-2-essigsa ure", Justus Liebigs Annalen Der Chemie. vol. 526, 1936. pp. 22-46. XP002633357.
Efremova T M et al., "1-Methyl-4-hetarylmethyl-beta-carolines", Chemistry of Heterocyclic Compounds, vol. 10, 1974, pp. 1210-1214, XP002633356.

Gazit, Aviv et al., "Tyrphostins. 5. Potent Inhibitors of Platelet-Derived Growth Factor Receptor Tyrosine Kinase: Structure-Activity Relationships in Quinoxalines, Quinolines, and Indole Tyrphostins", Journal of Medicinal Chemistry, vol. 39, No. 11, pp. 2170-2177, 1996.
Wilkens, Jochen et al., Hetero-Cope Rearrangements. VI[1]. Short and Stereoselective Synthesis of 2-Vinylindoles by a Tandem-process, Tetrahedron, vol. 43, No. 14, pp. 3237-3246, 1987.
Minot, C. et al., "Photocyclization of Stilbenes and of Related Indolic Compounds: Contribution of the use of Reactivity Indexes, Tetrahedron", vol. 36, No. 9, pp. 1209-1214, 1980 Considered the structures and information related to ISR.
Shafiee, a. et al., "Photochemical Synthesis of [1] Benzothieno [3, 2-h] isoquinoline", Journal of Heterocylclic Chemistry, vol. 13, No. 1, pp. 141-144, 1976.
Riche Claude et al., "Rearrangements in the Photochemical Synthesis of Indolic Compounds", Tetrahedeon Letters, vol. 51, pp. 4567-4570, 1975, Considered the structures and information related to ISR.
Dieng, C. et al., "Indol series. VII. Synthesis of new pyridocarbazoles obtained by photocylization of 1-(β-indolyl)-2-(pyridyl) acrylonitriles", Journal of heterocyclic Chemistry, vol. 12, No. 3, pp. 455-460, 1975 Considered the structures and information related to ISR.
Efremove, T.M. et al., "Carbolines. VII. 1-Metyl-4-hetarylmethyl-βcarbolines", Chemical Abstracts, vol. 82, p. 423, 1975.
Sreenivasulu, B. et al., "Search for Physiologically Active Compounds. Part XXI. Synthesis of 3-(2-Furyl) and 3-(2-Furyl)-4-Methyl Coumarins", Indian Academy of Sciences, Section 1, vol. 78, No. 4, pp. 159-168, 1973.
Buu-Hoi, N. P. et al., "Synthesis of Two Fluorinated 1-Naphthylacetic Acids", Journal of Organic chemistry, vol. 23, pp. 189-190, 1958.
Borsche, W. et al., "Quinolyl-2-pyroracemic acid and quinolyl-2-acetic acid", Chemical Abstracts, vol. 31, columns 405 to 406, col. 406, line 41, 1937.
Buu-Hoi, N. P. et al., "Thiophene derivatives of poltential biological interest. I. Thiophene analogs of stilbene and related compounds", Chemical abstracts, vol. 45, col. 3374, Par. No. [0002], lines f to h, 1951.
Doyle, L. Austin at el., "A multidrug resistance transporter from human MCF-7 breast cancer cells", The National Academy of Sciences, vol. 95, pp. 15665-15670, 1998.
Brangi, Mariafiorella et al., "Camptothecin Resistance: Role of the ATP-binding Cassette (ABC), Mitoxantrone-resistance Half-Transporter (MXR), and Potential for Glucuronidation in MXR-expressing Cells", Cancer Research, vol. 59, pp. 5938-5946, 1999.
Kruijtzer, C.M.F. et al., "Increased Oral Bioavailability of Topotecan in Combination With the Beast Cancer Resistance Protein and P-Glycoprotein Inhibitor GF120918", Journal of Clinical Oncology, vol. 20, No. 13, pp. 2943-2950, 2002.
Allen, John D. et al., "Potent and Specific Inhibition of the Beast Cancer Resistance Protein Multidrug Transporter in Vitro and in Mouse Intestine by a Novel Analogue of Fumitremorgin C[1]", Molecular Cancer Therapeutics, vol. 1, pp. 417-425, 2002.
Sugimoto, Yoshikazu et al., "Reversal of Breast Cancer Resistance Protein-mediated Drug Resistance by Estrogen Antagonists and Agonists[1]", Molecular Cancer Therapeutics, vol. 2, pp. 105-112, 2003.
Shiozawa, Ken et al., "Reversal of Breast Cancer Resistance Protein (BCRP-ABCG2)-Mediated Drug Resistance by Novobiocin, A Coumermycin Antibiotic", Publication of the International Union Against Cancer, vol. 108, pp. 146-151, 2004.
U.S. Appl. No. 11/909,805, filed Sep. 27, 2007, Yamazaki, et al.

* cited by examiner

BCRP/ABCG2 INHIBITOR

TECHNICAL FIELD

The present invention relates to a breast cancer resistance protein (BCRP/ABCG2) inhibitor.

BACKGROUND ART

Serious problems associated with cancer chemotherapy include intrinsic resistance to an anticancer agent, which invalidates the effect of the anticancer agent from the beginning of cancer therapy, and development of acquired resistance to an anticancer agent (i.e., reduction of the effect of the drug, which is caused by long-term continuous administration thereof). Overcoming such resistance to anticancer agents has been envisaged to lead to improvement in the performance of cancer chemotherapy, and thus attempts have been made to elucidate various resistance mechanisms. Particularly, expression of a drug transporter, which actively transports an anticancer agent out of cancer cells, thereby reducing the amount of intracellular accumulation of the drug, is considered to play an important role in such a resistance mechanism.

P-glycoprotein, in particular, which is a drug transporter discovered in the 1970s and is encoded by an MDR1 gene, has been considered a potent target molecule of a multidrug-resistance-overcoming agent, since this protein causes cross-resistance to a plurality of anticancer agents having different chemical structures and action mechanisms. However, it has been gradually elucidated that the anticancer agent resistance mechanism cannot be analyzed on the sole basis of P-glycoprotein, and demand has arisen for development of a resistance-overcoming agent which targets another drug transporter.

Under such circumstances, there was discovered, in 1998, breast cancer resistance protein (BCRP, also called ABCG2, MXR, or ABCP), which is a drug transporter belonging to a group which is called "ATP-binding cassette (ABC) transporter superfamily" to which P-glycoprotein also belongs (see Non-Patent Document 1). BCRP has a structure including only one ATP-binding cassette, which differs from that of P-glycoprotein or another ABC transporter, which has two ATP-binding cassettes. BCRP is involved in the mechanism of resistance to a topoisomerase I inhibitor (e.g., irinotecan hydrochloride (CPT-11) or topotecan), to a topoisomerase II inhibitor (e.g., mitoxantrone), or to a molecule-targeting therapeutic drug (e.g., gefitinib and imatinib). Meanwhile, BCRP has been elucidated to exhibit substrate specificity different from that of P-glycoprotein, since BCRP does not act on, for example, paclitaxel or vincristine, which is excreted by P-glycoprotein, and BCRP is involved in excretion of a camptothecin derivative (e.g., CPT-11 or 7-ethyl-10-hydroxycamptothecin (SN-38: active metabolite of CPT-11), which is barely excreted extracellularly by P-glycoprotein (see Non-Patent Document 2). In addition, BCRP has been suggested to be involved in the limitation of the bioavailability of an orally administered anticancer agent (see Non-Patent document 3). In view of the foregoing, demand has arisen for development of a BCRP inhibitor, which is envisaged to exhibit the effect of overcoming anticancer agent resistance that is not overcome by a conventional resistance-overcoming agent, and to improve the bioavailability of an anticancer agent.

Hitherto, in an attempt to overcome resistance to anticancer agents, a variety of P-glycoprotein inhibitors have been developed. In contrast, only a few reports have been given for BCRP inhibitors, and the reported inhibitory action is not satisfactory. Therefore, continuous efforts have been made to develop more effective BCRP inhibitors. Examples of the compounds exhibiting BCRP inhibitory action which have heretofore reported include an FTC (Fumitremorgin C) derivative (see Non-Patent Document 4), estrogen and anti-estrogen (see Non-Patent Document 5), and novobiocin (see Non-Patent Document 6). The present inventors also found that a flavonoid (see Patent Document 1) and a diphenylacrylonitrile derivative (see Patent Document 2) have potent BCRP inhibitory action.

Meanwhile, regarding acrylonitrile derivatives having a heterocyclic ring, an anticancer agent activated by CYP1B1 (see Patent Document 3), and 12-lipoxygenase inhibitor (Patent Document 4) have been reported. However, there have never been reported an acrylonitrile derivative having a heterocyclic ring which can serve as a BCRP inhibitor, an agent for overcoming resistance to anticancer agent, and an agent for potentiating anticancer agent effect.

Patent Document 1: WO 2004/069233
Patent Document 2: WO 2004/069243
Patent Document 3: WO 99/40056
Patent Document 4: JP-A-7-48336
Non-Patent Document 1: Proc. Natl. Acad. Sci. USA, 1998, 95: 15665-15670
Non-Patent Document 2: Cancer Res., 1999, 59: 5938-5946
Non-Patent Document 3: J. Clin. Oncol., 2002, 20: 2943-2950
Non-Patent Document 4: Mol. Cancer. Ther., 2002, 1: 417-425
Non-Patent Document 5: Mol. Cancer. Ther., 2003, 2: 105-112
Non-Patent Document 6: Int. J. Cancer, 2004, 108: 146-151

DISCLOSURE OF THE INVENTION

Problems to be Solved by the Invention

An object of the present invention is to provide drug for inhibiting a breast cancer resistance protein (BCRP).

Means for Solving the Problems

In an attempt to solve the aforementioned problems, the present inventors have carried out screening of compounds by use of cancer cells which have acquired anticancer drug resistance through BCRP expression, and have found that acrylonitrile derivatives represented by the following formula (1) exhibit potent BCRP inhibitory action. The inventors have also found that these acrylonitrile derivatives exhibiting BCRP inhibitory action include novel compounds. The present invention has been accomplished on the basis of these findings.

Accordingly, the present invention provides a BCRP inhibitor comprising, as an active ingredient, an acrylonitrile derivative represented by formula (1):

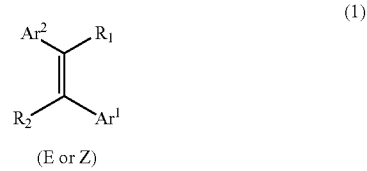

(1)

(E or Z)

[wherein one of $R_1$ and $R_2$ represents a cyano group and the other represents a hydrogen atom;

$Ar^1$ represents a group selected from among the groups represented by formulas (2) to (4):

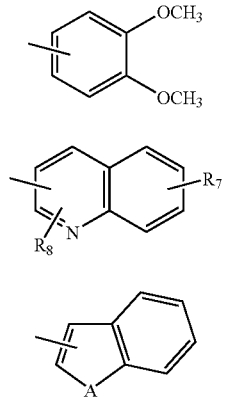

(wherein $R_7$ and $R_8$, which are identical to or different from each other, each represent a hydrogen atom, a halogen atom, or a lower alkoxy group;

A represents an oxygen atom, a sulfur atom, or $NR_9$; and $R_9$ represents a hydrogen atom or a lower alkyl group);

$Ar^2$ represents an aromatic hydrocarbon group having a condensed ring which may be substituted by a halogen atom, or a group selected from among the groups represented by formulas (5) to (15):

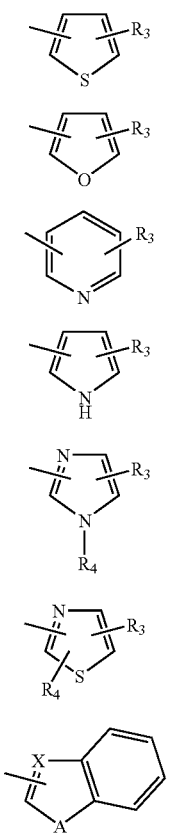

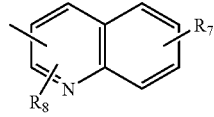

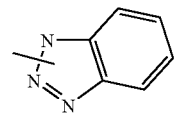

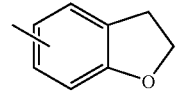

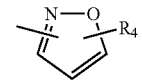

(wherein $R_3$ represents a hydrogen atom, an oxygen atom (as N-oxide), a lower alkyl group, a lower alkoxy group, a halogen atom, a nitro group, a methylsulfanyl group, a lower hydroxyalkyl group, an aromatic hydrocarbon group which may have a substituent, or $NR_5(R_6)$;

$R_9$ and $R_6$, which are identical to or different from each other, each represent a hydrogen atom, a lower alkyl group which may have a substituent, a lower hydroxyalkyl group, or an aromatic hydrocarbon group which may have a substituent or heterocyclic group; $R_5$ and $R_6$ may form, with their adjacent nitrogen atom, a heterocyclic ring which may have a substituent; and the hydroxyl group of the lower hydroxyalkyl group or the heterocyclic ring substituted by a hydroxyl group or a lower hydroxyalkyl group may form an ester bond with a phosphoric acid group or a salt thereof or with an acyl group which may have a substituent;

$R_4$ represents a hydrogen atom, a lower alkyl group, a phenyl group which may have a substituent, or a benzyl group;

X represents a carbon atom, CH, or a nitrogen atom, provided that when A is an oxygen atom, X is not a nitrogen atom); and A, $R_7$, $R_8$, and $R_9$ have the same meanings as defined above)] or a salt thereof.

The present invention also provides an agent for overcoming resistance to an anticancer agent (hereinafter referred to as "an agent for overcoming anticancer agent resistance") or an agent for potentiating the effect of an anticancer agent (hereinafter referred to as "an agent for potentiating anticancer agent effect"), which agent comprises, as an active ingredient, the aforementioned acrylonitrile derivative or a salt thereof.

The present invention also provides an anticancer agent composition containing the aforementioned acrylonitrile derivative or a salt thereof and an anticancer agent which serves as a BCRP substrate.

The present invention also provides use of the aforementioned acrylonitrile derivative or a salt thereof for the production of a BCRP inhibitor, an agent for overcoming anticancer agent resistance, or an agent for potentiating anticancer agent effect.

The present invention also provides a method for the treatment of cancer which has acquired drug resistance by the mediation of BCPR, characterized in that the method comprises administering the aforementioned acrylonitrile derivative or a salt thereof.

Among the compounds represented by formula (1), the compounds represented by the following formula (1a) are novel compounds. Thus, the present invention provides an acrylonitrile derivative represented by formula (1a):

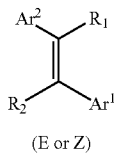

(1a)

(E or Z)

[wherein one of $R_1$ and $R_2$ represents a cyano group and the other represents a hydrogen atom;

$Ar^1$ represents a group selected from among the groups represented by formulas (2) to (4):

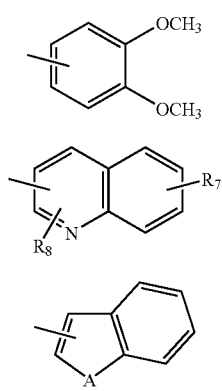

(2), (3), (4)

(wherein $R_7$ and $R_8$, which are identical to or different from each other, each represent a hydrogen atom, a halogen atom, or a lower alkoxy group;

A represents an oxygen atom, a sulfur atom, or $NR_9$; and $R_9$ represents a hydrogen atom or a lower alkyl group);

$Ar^2$ represents an aromatic hydrocarbon group having a condensed ring which may be substituted by a halogen atom, or a group selected from among the groups represented by formulas (5) to (15):

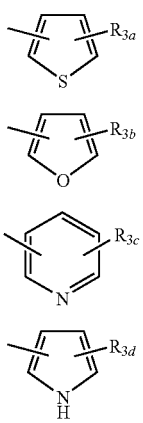

(5), (6), (7), (8)

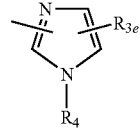

(9)

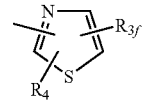

(10)

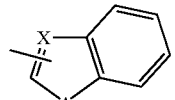

(11)

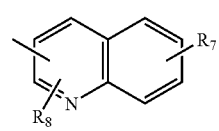

(12)

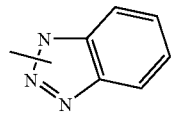

(13)

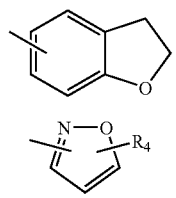

(14)

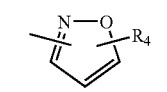

(15)

($R_{3a}$ represents a hydrogen atom ($Ar^1$ is a group represented by formula (3) or (4)), a lower alkyl group, a lower alkoxy group, a halogen atom, a nitro group, a methylsulfanyl group, a lower hydroxyalkyl group, an aromatic hydrocarbon group which may be substituted by a nitro group or an amino group, or $NR_5$ ($R_6$);

$R_{3b}$ represents a hydrogen atom, a lower alkyl group, a lower alkoxy group, a halogen atom, a nitro group, a methylsulfanyl group, a lower hydroxyalkyl group, an aromatic hydrocarbon group which may be substituted by an amino group, or $NR_5$ ($R_6$);

$R_{3c}$ represents a hydrogen atom ($Ar^1$ is a group represented by formula (3) or (4)), an oxygen atom (as N-oxide), a lower alkyl group, a lower alkoxy group, a halogen atom, a nitro group, a methylsulfanyl group, a lower hydroxyalkyl group, an aromatic hydrocarbon group which may be substituted by a nitro group or an amino group, or $NR_5(R_6)$;

each of $R_{3d}$, $R_{3e}$, and $R_{3f}$ represents a hydrogen atom, an oxygen atom (as N-oxide), a lower alkyl group, a lower alkoxy group, a halogen atom, a nitro group, a methylsulfanyl group, a lower hydroxyalkyl group, an aromatic hydrocarbon group which may be substituted by an amino group, or $NR_5$ ($R_6$);

$R_5$ and $R_6$, which are identical to or different from each other, each represent a hydrogen atom, a lower alkyl group which may have a substituent, a lower hydroxyalkyl group, or an aromatic hydrocarbon group which may have a substituent or heterocyclic group; $R_5$ and $R_6$ may form, with their adjacent nitrogen atom, a heterocyclic ring which may have a substituent; and the hydroxyl group of the lower hydroxyalkyl group or the heterocyclic ring substituted by a hydroxyl group or a lower hydroxyalkyl group may form an ester bond with a phosphoric acid group or a salt thereof or with an acyl group which may have a substituent;

$R_4$ represents a hydrogen atom, a lower alkyl group, a phenyl group which may have a substituent, or a benzyl group;

X represents a carbon atom, CH, or a nitrogen atom, provided that when A is an oxygen atom, X is not a nitrogen atom); and A, $R_7$, $R_8$, and $R_9$ have the same meanings as defined above)] or a salt thereof.

The present invention also provides a drug comprising, as an active ingredient, a compound represented by formula (1a) or a salt thereof.

The present invention also provides a pharmaceutical composition containing a compound represented by formula (1a) or a salt thereof and a pharmaceutically acceptable carrier.

The present invention also provides use of a compound represented by formula (1a) or a salt thereof, for producing a drug.

EFFECTS OF THE INVENTION

According to the present invention, the BCRP inhibitory effect of the acrylonitrile derivative or a salt thereof can overcome BCRP-related resistance to an anticancer agent. In addition, the effect of an anticancer agent with respect to cancer cells in which BCRP is intrinsically expressed can be potentiated. Furthermore, according to the present invention, bioavailability of an anticancer agent is envisaged to be enhanced, leading to improvement in the performance of cancer chemotherapy.

BEST MODES FOR CARRYING OUT THE INVENTION

Figure 1:
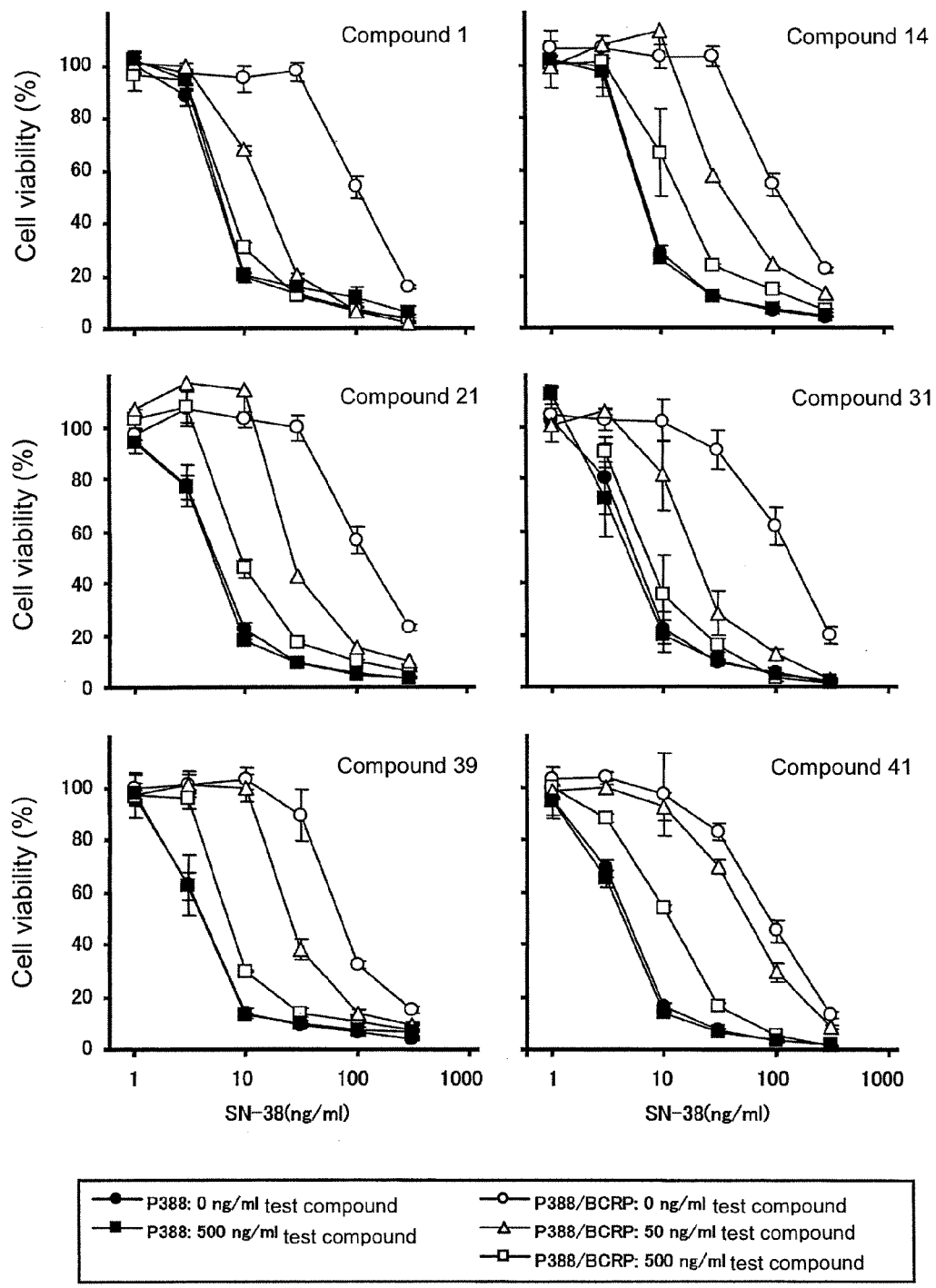
FIG. 1 Graphs showing action of some compounds of the present invention on SN-38 resistance of P388/BCRP cells.

Examples of the aromatic hydrocarbon group having a condensed ring which may be substituted by a halogen atom represented by $Ar^2$ in formula (1) include C10 to C14 aryl groups. Specific examples include naphthyl, anthracenyl, and phenanthryl. Examples of the halogen atom by which the aromatic hydrocarbon group of $Ar^2$ may be substituted include a fluorine atom, a chlorine atom, and an iodine atom.

Examples of the lower alkyl group represented by $R_3$, $R_{3a}$ to $R_{3f}$, $R_4$, or $R_9$ in formula (1) include linear or branched-chain C1 to C6 alkyl groups. Specific examples include methyl, ethyl, n-propyl, isopropyl, and n-butyl. Of these, methyl is particularly preferred.

Examples of the lower alkoxy group represented by $R_3$, $R_{3a}$ to $R_{3f}$, $R_7$, or $R_8$ include linear or branched-chain C1 to C6 alkoxy groups and C3 to C6 cycloalkyloxy groups. Specific examples include methoxy, ethoxy, n-propoxy, isopropoxy, and n-butoxy. Of these, methoxy is particularly preferred.

Examples of the halogen atom include a fluorine atom, a chlorine atom, a bromine atom, and an iodine atom.

Examples of the lower hydroxyalkyl group represented by $R_3$, or $R_{3a}$ to $R_{3f}$ include linear or branched-chain C1 to C6 hydroxyalkyl groups. Specific examples include hydroxymethyl, hydroxyethyl, and 1-hydroxypropyl. Of these, hydroxymethyl is particularly preferred.

Examples of the aromatic hydrocarbon group represented by $R_3$ or $R_{3a}$ to $R_{3f}$ include C6 to C14 aryl groups. Specific examples include phenyl and naphthyl. Examples of the group by which the aromatic hydrocarbon group $R_3$ may be substituted include an amino group and a nitro group. Specific examples include a nitrophenyl group and an aminophenyl group.

Examples of the group by which the phenyl group $R_4$ may be substituted include halogen atoms and lower alkoxy groups. The halogen atom and the lower alkoxy group have the same meanings as defined in relation to $R_3$.

Examples of the lower alkyl group which may have a substituent and which is represented by $R_5$ or $R_6$ include linear or branched-chain C1 to C6 alkyl groups. Examples of the group by which the lower alkyl group may be substituted include C1 to C6 alkylamino groups and di(C1 to C6 alkyl) amino groups. Specific examples include methylamino, ethylamino, n-propylamino, isopropylamino, cyclopropylamino, dimethylamino, and diethylamino.

The lower hydroxyalkyl group represented by $R_5$ or $R_6$ and the aromatic hydrocarbon group which may have a substituent have the same meanings as defined in relation to $R_3$.

Examples of the heterocyclic group represented by $R_5$ or $R_6$ include alycyclic or aromatic heterocyclic compounds each having at least one hetero atom in the ring. Specific examples include piperazinyl, piperidino, morpholino, imidazolyl, and pyrrolidinyl.

Examples of the heterocyclic ring which may have a substituent and which may be formed from $R_5$ and $R_6$ with their adjacent nitrogen atom include pyrrolidine, imidazole, pyridine, piperidine, pyrimidine, piperazine, morpholine, indole, benzimidazole, benzpyrazole, and quinoline. Examples of the group by which these heterocyclic rings may be substituted include a hydroxyl group, lower alkyl groups, and lower hydroxyalkyl groups. These groups have the same meanings as defined above.

Examples of the substituent $NR_5(R_6)$ include an amino group, a dimethylamino group, an N-methyl-ethanolamino group (—N(CH$_3$)CH$_2$CH$_2$OH), a phosphate ester of an N-methyl-ethanolamino group (—N(CH$_3$)CH$_2$CH$_2$OH) and a salt thereof, a monosuccinate of an N-methyl-ethanolamino group (—N(CH$_3$)CH$_2$CH$_2$OH), a pyrrolidino group, a piperidino group, a morpholino group, a 4-hydroxypiperidino group, a phosphate ester of a 4-hydroxypiperidino group and a salt thereof, a monosuccinate of a 4-hydroxypiperidino group, a 4-methylpiperazino group, a 4-ethanolpiperazino group, a phosphate ester of a 4-ethanolpiperazino group and a salt thereof, a monosuccinate of a 4-ethanolpiperazino group, and an N,N,N'-trimethylethylenediamino group (—N(CH$_3$)CH$_2$CH$_2$N(CH$_3$)$_2$).

The hydroxy group in the lower hydroxyalkyl group represented by $R_5$ or $R_6$, and the hydroxy group in the hydroxyl group or the lower hydroxyalkyl group by which the heterocyclic group may be substituted, the heterocyclic group formed from $R_5$ and $R_6$ with their adjacent nitrogen atom, may form an ester bond with a phosphate group or a salt thereof or with an acyl group which may have a substituent.

Examples of the acyl group include C1 to C8 lower alkanoly groups. Specific examples include formyl, acetyl, propionyl, malonyl, and succinyl. The group by which the acyl group may be substituted include di-lower alkylamino groups; phenylcarbamoyl groups which may have a substituent; N-lower alkylcarbamoyl groups which may have a substituent, N,N-di-lower alkylcarbamoyl groups; and N-heterocyclic carbamoyl groups which may be substituted by an aliphatic heterocyclic ring. The lower alkyl group has the same meaning as defined above.

Examples of the group by which the phenylcarbamoyl group, the N-lower alkylcarbamoyl group, or the N,N-di-lower alkylcarbamoyl group may be substituted include a lower alkylamino groups such as a methylamino group and an ethylamino group; and di-lower alkylamino groups such as a diethylamino group and a dipropylamino group.

Examples of the N-heterocyclic carbamoyl group which may be substituted by an aliphatic heterocyclic ring include N-piperidinocarbonyl groups each substituted by pyrrolidine, piperidine, piperazine, or a similar heterocyclic ring.

Examples of the acyl group which may have a substituent include a dimethylaminoacetyl group, a diethylaminoethylaminocarbonylpropionyl group, a diethylaminopropylaminocarbonylpropionyl group, a diethylaminophenylaminocarbonylpropionyl group, a 4-piperidinopiperidin-1-yl-carbonyl group, and a 4-piperidinopiperidin-1-yl-carbonylpropionyl group.

The acrylonitrile derivatives of the present invention may form pharmaceutically acceptable salts thereof, and these salts also fall within the scope of the present invention. Examples of the salts include inorganic salts such as hydrochlorides, sulfates, nitrates, and phosphates; alkali metal salts such as sodium salts and potassium salts; alkaline earth metal salts such as calcium salts and magnesium salts; and organic acid salts such as p-toluenesulfonates, methanesulfonates, fumarates, succinates, and lactates. The compounds of the present invention may be present in the form of solvate (hydrate). The hydrates also fall within the scope of the present invention. The acrylonitrile derivatives of the present invention may include isomers thereof, and each of these isomers and mixtures of the isomers also fall within the scope of the present invention.

Of these, more preferred are the following compounds and salts:

(Z)-2-(3,4-dimethoxy-phenyl)-3-(5-nitro-thiophen-2-yl)-acrylonitrile (Compound 1), (Z)-3-(5-bromo-thiophen-2-yl)-2-(3,4-dimethoxy-phenyl)-acrylonitrile (Compound 2), (Z)-3-(5-amino-thiophen-2-yl)-2-(3,4-dimethoxy-phenyl)-acrylonitrile (Compound 3), (Z)-2-(3,4-dimethoxy-phenyl)-3-(5-piperidin-1-yl-thiophen-2-yl)-acrylonitrile (Compound 4) or a hydrochloric acid salt thereof (Compound 11), (Z)-2-(3,4-dimethoxy-phenyl)-3-(5-morpholin-4-yl-thiophen-2-yl)-acrylonitrile (Compound 5), (Z)-2-(3,4-dimethoxy-phenyl)-3-[5-(4-hydroxy-piperidin-1-yl)-thiophen-2-yl]-acrylonitrile (Compound 6) or a hydrochloric acid salt thereof (Compound 12), (Z)-2-(3,4-dimethoxy-phenyl)-3-{5-[(2-hydroxy-ethyl)-methyl-amino]-thiophen-2-yl}-acrylonitrile (Compound 7), (Z)-2-(3,4-dimethoxy-phenyl)-3-[5-(4-methyl-piperazin-1-yl)-thiophen-2-yl]-acrylonitrile (Compound 8) or a hydrochloric acid salt thereof (Compound 13), (Z)-2-(3,4-dimethoxy-phenyl)-3-{5-[4-(2-hydroxy-ethyl)-piperazin-1-yl]-thiophen-2-yl}-acrylonitrile (Compound 9), a hydrochloric acid salt thereof (Compound 14), a methanesulfonic acid salt thereof (Compound 59), a ½ sulfuric acid salt thereof (Compound 100), a sulfuric acid salt thereof (Compound 101), or a nitric acid salt thereof (Compound 102), (Z)-2-(3,4-dimethoxy-phenyl)-3-{5-[(2-dimethylamino-ethyl)-methyl-amino]-thiophen-2-yl}-acrylonitrile (Compound 10) or a hydrochloric acid salt thereof (Compound 15), mono-(1-{5-[(Z)-2-cyano-2-(3,4-dimethoxy-phenyl)-vinyl]-thiophen-2-yl}-piperidin-4-yl)phosphate (Compound 16) or a sodium salt thereof (Compound 17), mono-(1-{5-[(Z)-2-cyano-2-(3,4-dimethoxy-phenyl)-vinyl]-thiophen-2-yl}-piperidin-4-yl)succinate (Compound 18) or a sodium salt thereof (Compound 57), (Z)-2-(3,4-dimethoxy-phenyl)-3-(5-nitro-furan-2-yl)-acrylonitrile (Compound 19), (Z)-2-(3,4-dimethoxy-phenyl)-3-(5-hydroxy-methyl-furan-2-yl)-acrylonitrile (Compound 20), (Z)-2-(3,4-dimethoxy-phenyl)-3-[5-(3-nitro-phenyl)-furan-2-yl]-acrylonitrile (Compound 21), (Z)-3-[5-(3-amino-phenyl)-furan-2-yl]-2-(3,4-dimethoxy-phenyl)-acrylonitrile (Compound 22) or a hydrochloric acid salt thereof (Compound 23), (Z)-2-(3,4-dimethoxy-phenyl)-3-(5-piperidin-1-yl-furan-2-yl)-acrylonitrile (Compound 24), (Z)-2-(3,4-dimethoxy-phenyl)-3-(5-morpholin-4-yl-furan-2-yl)-acrylonitrile (Compound 25), (Z)-2-(3,4-dimethoxy-phenyl)-3-[5-(4-hydroxy-piperidin-1-yl)-furan-2-yl]-acrylonitrile (Compound 26), (Z)-2-(3,4-dimethoxy-phenyl)-3-[5-(4-methyl-piperazin-1-yl)-furan-2-yl]-acrylonitrile (Compound 27) or a hydrochloric acid salt thereof (Compound 29), (Z)-2-(3,4-dimethoxy-phenyl)-3-{5-[4-(2-hydroxy-ethyl)-piperazin-1-yl]-furan-2-yl}-acrylonitrile (Compound 28) or a hydrochloric acid salt thereof (Compound 50), (Z)-2-(3,4-dimethoxy-phenyl)-3-pyridin-4-yl-acrylonitrile (Compound 30), a hydrochloric acid salt thereof (Compound 31), or a methanesulfonic acid salt thereof (Compound 32), (Z)-2-(3,4-dimethoxy-phenyl)-3-pyridin-4-yl-acrylonitrile N-oxide (Compound 33), (Z)-2-(3,4-dimethoxy-phenyl)-3-pyridin-3-yl-acrylonitrile (Compound 34) or a hydrochloric acid salt thereof (Compound 36), (Z)-2-(3,4-dimethoxy-phenyl)-3-(6-methoxy-pyridin-3-yl)-acrylonitrile (Compound 35) or a hydrochloric acid salt thereof (Compound 37), (Z)-2-(3,4-dimethoxy-phenyl)-3-pyridin-2-yl-acrylonitrile (Compound 38), (Z)-2-(3,4-dimethoxy-phenyl)-3-(1H-pyrrol-2-yl)-acrylonitrile (Compound 39) or a hydrochloric acid salt thereof (Compound 40), (Z)-2-(3,4-dimethoxy-phenyl)-3-(3H-imidazol-4-yl)-acrylonitrile (Compound 41), (Z)-3-(3-benzyl-2-methylsulfanyl-3H-imidazol-4-yl)-2-(3,4-dimethoxy-phenyl)-acrylonitrile (Compound 42), (Z)-2-(3,4-dimethoxy-phenyl)-3-(4-methyl-2-phenyl-thiazol-5-yl)-acrylonitrile (Compound 43), (Z)-3-(3,4-dimethoxy-phenyl)-2-pyridin-3-yl-acrylonitrile (Compound 44) or a hydrochloric acid salt thereof (Compound 46), (Z)-3-(3,4-dimethoxy-phenyl)-2-pyridin-2-yl-acrylonitrile (Compound 45) or a hydrochloric acid salt thereof (Compound 47), (Z)-2-(3,4-dimethoxy-phenyl)-3-{5-[(2-dimethylamino-ethyl)-methyl-amino]-furan-2-yl}-acrylonitrile (Compound 48) or a hydrochloric acid salt thereof (Compound 49), mono-(1-{5-[(Z)-2-cyano-2-(3,4-dimethoxy-phenyl)-vinyl]-furan-2-yl}-piperidin-4-yl)succinate (Compound 51) or a sodium salt thereof (Compound 58), mono-(1-{5-[(Z)-2-cyano-2-(3,4-dimethoxy-phenyl)-vinyl]-furan-2-yl}-piperidin-4-yl)phosphate (Compound 52) or a sodium salt thereof (Compound 53), (Z)-3-(5-bromo-furan-2-yl)-2-(3,4-dimethoxy-phenyl)-acrylonitrile (Compound 54),
(E)-3-(3,4-dimethoxy-phenyl)-2-thiophen-2-yl-acrylonitrile (Compound 55),
(Z)-3-(3,4-dimethoxy-phenyl)-2-thiophen-3-yl-acrylonitrile (Compound 56),
1-[5-[(Z)-2-cyano-2-(3,4-dimethoxy-phenyl)-vinyl]-thiophen-2-yl]-piperidin-4-yl N-(2-diethylamino-ethyl)-succinamate hydrochloric acid salt (Compound 60),
1-[5-[(Z)-2-cyano-2-(3,4-dimethoxy-phenyl)-vinyl]-thiophen-2-yl]-piperidin-4-yl N-(3-diethylamino-propyl)-succinamate hydrochloric acid salt (Compound 61),
1-[5-[(Z)-2-cyano-2-(3,4-dimethoxy-phenyl)-vinyl]-thiophen-2-yl]-piperidin-4-yl dimethylamino-acetate p-toluenesulfonic acid salt (Compound 62) or a hydrochloric acid salt thereof (Compound 104),
1-[5-[(Z)-2-cyano-2-(3,4-dimethoxy-phenyl)-vinyl]-thiophen-2-yl]-piperidin-4-yl [1,4']bipiperidinyl-1'-carboxylate hydrochloric acid salt (Compound 63),
1-[5-[(Z)-2-cyano-2-(3,4-dimethoxy-phenyl)-vinyl]-thiophen-2-yl]-piperidin-4-yl 4-[1,4']bipiperidinyl-1'-yl-4-oxo-butylate hydrochloric acid salt (Compound 64),
(Z)-2-(3,4-dimethoxy-phenyl)-3-quinolin-4-yl-acrylonitrile (Compound 65),
(Z)-3-benzo[b]thiophen-3-yl-2-(3,4-dimethoxy-phenyl)-acrylonitrile (Compound 66),
(Z)-2-(3,4-dimethoxy-phenyl)-3-(1-methyl-1H-benzimidazol-2-yl)-acrylonitrile (Compound 67),
(Z)-2-(3,4-dimethoxy-phenyl)-3-(1-methyl-1H-indol-3-yl)-acrylonitrile (Compound 68),
(Z)-3-benzofuran-2-yl-(3,4-dimethoxy-phenyl)-acrylonitrile (Compound 69),
(Z)-3-(2-chloro-quinolin-3-yl)-2-(3,4-dimethoxy-phenyl)-acrylonitrile (Compound 70),
(E)-2-benzothiazol-1-yl-3-(3,4-dimethoxy-phenyl)-acrylonitrile (Compound 71),
(Z)-2-benzofuran-3-yl-3-(3,4-dimethoxy-phenyl)-acrylonitrile (Compound 72),
(Z)-3-(2-chloro-6-methoxy-quinolin-3-yl)-2-(3,4-dimethoxy-phenyl)-acrylonitrile (Compound 73),
(E)-2-benzothiazol-2-yl-3-(3,4-dimethoxy-phenyl)-acrylonitrile (Compound 74),
(Z)-3-(2,3-dihydro-benzofuran-5-yl)-2-(3,4-dimethoxy-phenyl)-acrylonitrile (Compound 75),
(Z)-2-(3,4-dimethoxy-phenyl)-3-[5-(4-fluoro-phenyl)-isoxazol-3-yl]-acrylonitrile (Compound 76),
(Z)-2-(3,4-dimethoxy-phenyl)-3-[5-(4-methoxy-phenyl)-isoxazol-3-yl]-acrylonitrile (Compound 77),
(Z)-2-(3,4-dimethoxy-phenyl)-3-quinolin-2-yl-acrylonitrile (Compound 78),
(Z)-3-(2-chloro-6-methoxy-quinolin-3-yl)-2-pyridin-2-yl-acrylonitrile (Compound 79),
(Z)-3-(2-chloro-6-methoxy-quinolin-3-yl)-2-pyridin-3-yl-acrylonitrile (Compound 80),
(E)-3-(2-chloro-6-methoxy-quinolin-3-yl)-2-thiophen-2-yl-acrylonitrile (Compound 81),
(Z)-3-(2-chloro-6-methoxy-quinolin-3-yl)-2-thiophen-3-yl-acrylonitrile (Compound 82),
(E)-2-benzotriazol-1-yl-3-(2-chloro-6-methoxy-quinolin-3-yl)-acrylonitrile (Compound 83),
(E)-2-benzothiazol-2-yl-3-(2-chloro-6-methoxy-quinolin-3-yl)-acrylonitrile (Compound 84),
(Z)-2-pyridin-2-yl-3-quinolin-4-yl-acrylonitrile (Compound 85),
(Z)-2-pyridin-3-yl-3-quinolin-4-yl-acrylonitrile (Compound 86),
(E)-3-quinolin-4-yl-2-thiophen-2-yl-acrylonitrile (Compound 87),
(Z)-3-quinolin-4-yl-2-thiophen-3-yl-acrylonitrile (Compound 88),
(E)-3-benzo[b]thiophen-3-yl-2-thiophen-2-yl-acrylonitrile (Compound 89),
(E)-3-benzo[b]thiophen-3-yl-2-benzothiazol-2-yl-acrylonitrile (Compound 90),
(Z)-3-benzofuran-2-yl-2-benzofuran-3-yl-acrylonitrile (Compound 91),
(E)-2-benzothiazol-2-yl-3-(1-methyl-1H-indol-3-yl)-acrylonitrile (Compound 92),
(Z)-3-(10-chloro-anthracen-9-yl)-2-(3,4-dimethoxy-phenyl)-acrylonitrile (Compound 93),
(Z)-2-(3,4-dimethoxy-phenyl)-3-naphthalen-2-yl-acrylonitrile (Compound 94),
(Z)-2-(3,4-dimethoxy-phenyl)-3-phenanthren-9-yl-acrylonitrile (Compound 95),
1-[5-[(Z)-2-cyano-2-(3,4-dimethoxy-phenyl)-vinyl]-thiophen-2-yl]-piperidin-4-yl diethylamino-acetate (Compound 103), a p-toluenesulfonic acid salt thereof (Compound 96), or a hydrochloric acid salt thereof (Compound 105),
1-[5-[(Z)-2-cyano-2-(3,4-dimethoxy-phenyl)-vinyl]-thiophen-2-yl]-piperidin-4-yl diethyl-carbamate (Compound 97),
1-[5-[(Z)-2-cyano-2-(3,4-dimethoxy-phenyl)-vinyl]-thiophen-2-yl]-piperidin-4-yl N-(2-diethylamino-ethyl)-N-methyl-succinamate hydrochloric acid salt (Compound 98), and
1-[5-[(Z)-2-cyano-2-(3,4-dimethoxy-phenyl)-vinyl]-thiophen-2-yl]-piperidin-4-yl N-(4-diethylamino-phenyl)-succinamate (Compound 99).

The acrylonitrile derivatives of the present invention and salts thereof may be produced through, for example the following reaction scheme (A) or (B):

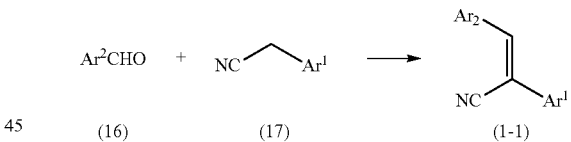

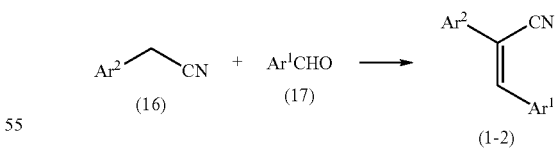

(wherein $Ar^1$ and $Ar^2$ have the same meanings as defined above).

Specifically, through condensation between an aromatic aldehyde (16) or (19) and an aromatic acetonitrile (17) or (18), an acrylonitrile derivative (1-1) or (1-2) can be produced. More specifically, condensation between an aromatic aldehyde (16) and 3,4-dimethoxybenzyl cyanide (17) yields an acrylonitrile derivative (1-1), whereas condensation between an aromatic acetonitrile (18) and 3,4-dimethoxybenzaldehyde (19) yields an acrylonitrile derivative (1-2).

Alternatively, through condensation between a polycyclic aromatic aldehyde (16) and 3,4-dimethoxybenzyl cyanide (17), an acrylonitrile derivative (1-1) can be produced. Through condensation between a heterocyclic acetonitrile (18) and a quinolinecarboxaldehyde (19), an acrylonitrile derivative (1-2) can be produced. Also, through condensation between a benzothiophenecarboxaldehyde, a benzofurancarboxaldehyde, or an indolecarboxaldehyde (19) and a heterocyclic acetonitrile (18), an acrylonitrile derivative (1-2) can be produced.

The condensation reaction is preferably carried out in the presence of a base such as sodium alkoxide, sodium hydroxide, or potassium hydroxide. When sodium alkoxide is employed, the condensation reaction is performed in an alcoholic solvent, such as methanol or ethanol, at between ice cooling temperature and reflux temperature, whereas when sodium hydroxide is employed, the condensation reaction is performed in a solvent mixture of water and an inert solvent, such as methylene chloride or chloroform, with a quaternary ammonium salt or a similar compound being added thereto.

The acrylonitrile derivatives each having a heterocyclic ring of the present invention or salts thereof may be administered as is. Alternatively, the derivatives or salts thereof may be mixed with a pharmaceutically acceptable carrier such as a dispersing aid or an excipient, and may be used in the form of an injection or a peroral preparation such as powder, solution, capsules, suspension, emulsion, syrup, elixir, granules, pills, tablets, troches, or lemonade. These products may be prepared through a conventional method.

Examples of such a carrier include water-soluble monosaccharides, oligosaccharides, and polysaccharides, such as mannitol, lactose, and dextran; gel-forming or water-soluble celluloses, such as hydroxypropyl cellulose, hydroxypropylmethyl cellulose, and methyl cellulose; water-absorbing and poorly water-soluble celluloses, such as crystalline cellulose, α-cellulose, cross-linked carboxymethylcellulose sodium, and derivatives thereof; water-absorbing and poorly water-soluble polysaccharides, such as hydroxypropyl starch, carboxymethyl starch, cross-linked starch, amylose, amylopectin, pectin, and derivatives thereof; water-absorbing and poorly water-soluble gums, such as gum arabic, tragacanth gum, glucomannan, and derivatives thereof; cross-linked vinyl polymers, such as polyvinyl pyrrolidone, cross-linked polyacrylic acid and salts thereof, cross-linked polyvinyl alcohol, polyhydroxyethyl methacrylate, and derivatives thereof; and molecular aggregate (e.g., liposome)-forming lipids, such as phospholipid and cholesterol.

When the compound of the present invention exhibits low solubility, the compound may be subjected to solubilization. Examples of the solubilization technique include techniques which are generally applicable to drugs, such as a technique in which a surfactant (e.g., a polyoxyethylene alcohol ether, a polyoxyethylene acyl ester, a sorbitan acyl ester, or a polyoxyethylene sorbitan acyl ester) is added to the compound, and a technique employing a water-soluble polymer (e.g., polyethylene glycol). If desired, there may be employed, for example, a technique for forming a soluble salt of the compound, or a technique for forming a clathrate compound by use of cyclodextrin or a similar material. A solubilization technique may be appropriately selected in accordance with the target acrylonitrile derivative or a salt thereof.

By virtue of a potent inhibitory BCRP effect, the compound of the present invention can be employed as an agent for overcoming anticancer agent resistance, and an agent for potentiating anticancer agent effect. The BCRP inhibitor may be employed as an agent for overcoming anticancer agent resistance for a cancer which has acquired BCRP-mediated resistance through administration of an anticancer drug. Meanwhile, the BCRP inhibitor may be employed as an agent for potentiating anticancer agent effect for a cancer which intrinsically expresses BCRP and exhibits low sensitivity to an anticancer drug. No particular limitation is imposed on the target anticancer drug on which the agent for overcoming anticancer agent resistance or agent for potentiating anticancer agent effect containing, as an active ingredient, the BCRP inhibitor of the present invention, acts, so long as the anticancer drug can serve as a substrate for BCRP or its analog. Examples of such an anticancer drug include topoisomerase I inhibitors such as irinotecan hydrochloride/CPT-11 (active metabolite: SN-38) and topotecan; topoisomerase II inhibitors such as mitoxantrone, doxorubicin, daunorubicin, bisantrene, and etoposide; antifolates such as methotrexate; and molecule-targeting therapeutic drugs such as gefitinib and imatinib. Notably, no particular limitation is imposed on the BCPR analog, so long as it has the same anticancer resistance as that of BCRP.

The dose of the BCRP inhibitor of the present invention may be appropriately determined in accordance with, for example, the administration method or the symptom of a patient. The daily dose for an adult is preferably 1 mg to 10 g, more preferably 100 mg to 10 g, particularly preferably 500 mg to 10 g. No particular limitations are imposed on the ratio between an anticancer drug and the BCRP inhibitor, and the preferred ratio varies in accordance with, for example, the type of an anticancer drug or inhibitor to be employed. When, for example, irinotecan hydrochloride is employed as an anticancer drug, the ratio by weight of the anticancer drug to the BCRP inhibitor is preferably 1:1 to 1:500, particularly preferably 1:1 to 1:100, more preferably 1:1 to 1:10.

EXAMPLE

The present invention will next be described in more detail by way of examples, which should not be construed as limiting the invention thereto.

Example 1

Production of an Acrylonitrile Derivative Having a Heterocyclic Ring

Production Step 1

Introduction of Amine into a Halogenated Heterocyclic Aldehyde

Water was added to a reactor in which a halogenated heterocyclic aldehyde, and an amine (3 eq.) was added to the reactor. Under reflux conditions, the mixture was stirred for several ten minutes to one day. After cooling, the mixture was extracted with chloroform. The organic layer was washed with brine and dried over sodium sulfate anhydrate. The solvent was evaporated to dryness. The reside was purified by silica gel column chromatography, to thereby yield a compound of interest.

Production Step 2

Method A

Step of Condensation Between Aromatic or Polycyclic Aromatic Aldehyde and 3,4-Dimethoxybenzyl Cyanide Equiamounts (eq.) of an aromatic or polycyclic aromatic aldehyde derivative and 3,4-dimethoxybenzyl cyanide were placed in a reactor, and ethanol was added thereto. A calcium chloride tube was attached to the reactor, and the mixture was stirred in the reactor for dissolution. Separately, 1 to 2 eqs. of sodium ethoxide was weighed and dissolved in ethanol, and the solution was added dropwise portion by portion to the above-prepared solution. The mixture was stirred at about an ice cooling temperature to a reflux temperature. After completion of reaction, water was added to the reaction mixture, and ethanol was evaporated to dryness. The mixture was extracted with chloroform, and the organic layer was washed with brine, followed by drying over sodium sulfate anhydrate. The solvent was evaporated to dryness. The residue was purified by silica gel column chromatography and recrystallized from ethanol, to thereby yield a compound of interest.

Production Step 2

Method B

Step of Condensation Between Aromatic Acetonitrile and 3,4-Dimethoxybenzaldehyde Equiamounts (eq.) of an aromatic acetonitrile derivative and 3,4-dimethoxybenzaldehyde were placed in a reactor, and ethanol was added thereto. A calcium chloride tube was attached to the reactor, and the mixture was stirred in the reactor for dissolution. Separately, 1 to 2 eqs. of sodium ethoxide was weighed and dissolved in ethanol, and the solution was added dropwise portion by portion to the above-prepared solution. The mixture was stirred at room temperature. After completion of reaction, water was added to the reaction mixture, and ethanol was evaporated to dryness. The mixture was extracted with chloroform, and the organic layer was washed with brine, followed by drying over sodium sulfate anhydrate. The solvent was evaporated to dryness. The residue was purified by silica gel column chromatography and recrystallized from ethanol, to thereby yield a compound of interest.

Production Step 3

Method B

Step of Condensation Between Heterocyclic Acetonitrile and Quinolinecarboxaldehyde, Benzothiophenecarboxaldehyde, Benzofurancarboxaldehyde, or Indolecarboxaldehyde Equiamounts (eq.) of a heterocyclic acetonitrile derivative and an aldehyde derivative were placed in a reactor. Through the same procedure as employed in "Production step 2: method B," a compound of interest was yielded.

Specific production of various such derivatives and analytical results will next be described.

Production of (Z)-2-(3,4-dimethoxy-phenyl)-3-(5-nitro-thiophen-2-yl)-acrylonitrile (Compound 1)

5-Nitrothiophene-2-carboxaldehyde (3.14 g) was condensed with 3,4-dimethoxybenzyl cyanide (3.54 g) through Method A (production step 2), to thereby yield the target product (yield: 540 mg, 8.5%).
Orange Crystals
MS (APCI, m/z): 316(M)$^-$
$^1$H-NMR (CDCl$_3$) δ: 7.93 (1H, d, J=4.4), 7.56 (1H, d, J=4.4), 7.43 (1H, s), 7.30 (1H, dd, J=2.0, 8.3), 7.12 (1H, d, J=2.0), 6.94 (1H, d, J=8.3), 3.97 (3H, s), 3.95 (3H, s)

Production of (Z)-3-(5-bromo-thiophen-2-yl)-2-(3,4-dimethoxy-phenyl)-acrylonitrile (Compound 2)

5-Bromothiophene-2-carboxaldehyde (381 mg) was condensed with 3,4-dimethoxybenzyl cyanide (355 mg) through Method A (production step 2), to thereby yield the target product (yield: 359 mg, 51%).
Slightly Yellow Crystals
MS (APCI, m/z): 349 (M)$^+$
$^1$H-NMR (CDCl$_3$) δ: 7.41 (1H, s), 7.31 (1H, d, J=4.2), 7.21 (1H, dd, J=2.2, 8.5), 7.10 (1H, d, J=4.2), 7.08 (1H, d, J=2.2), 6.90 (1H, d, J=8.5), 3.96 (3H, s), 3.93 (3H, s)

Production of (Z)-3-(5-amino-thiophen-2-yl)-2-(3,4-dimethoxy-phenyl)-acrylonitrile (Compound 3)

Compound 1 (316 mg) was dissolved in ethanol (25 mL), and calcium chloride dihydrate (132 mg) and zinc powder (2.55 g) were added to the solution, followed by stirring for 2 hours under reflux. The reaction mixture was subjected to filtration by use of a celite pad, to thereby remove zinc powder, and the solvent was evaporated to dryness. The residue was purified by silica gel column chromatography (hexane-ethyl acetate), to thereby yield the target product (yield: 35 mg, 12%).
Yellowish Brown Crystals
MS (ESI, m/z): 287 (M+H)$^+$
$^1$H-NMR (CDCl$_3$) δ: 7.37 (1H, s), 7.14 (1H, d, J=3.9), 7.13 (1H, dd, J=2.4, 8.3), 7.04 (1H, d, J=2.4), 6.88 (1H, d, J=8.3), 6.13 (1H, d, J=3.9), 4.34 (2H, brs), 3.94 (3H, s), 3.91 (3H, s)

Production of (Z)-2-(3,4-dimethoxy-phenyl)-3-(5-piperidin-1-yl-thiophen-2-yl)-acrylonitrile (Compound 4)

Through the procedure as employed in Production step 1, an amine moiety derived from piperidine (1.02 g) was introduced into 5-bromothiophene-2-carboxaldehyde (764 mg), to thereby yield 5-piperidin-1-yl-thiophene-2-carbaldehyde (yield: 500 mg, 64%). The produced 5-piperidin-1-yl-thiophene-2-carbaldehyde (293 mg) was condensed with 3,4-dimethoxybenzyl cyanide (266 mg) through Method A (production step 2), to thereby yield the target product (yield: 279 mg, 53%).
Yellow Crystals
MS (ESI, m/z): 355 (M+H)$^+$
$^1$H-NMR (CDCl$_3$) δ: 7.36 (1H, s), 7.22 (1H, d, J=4.2), 7.12 (1H, dd, J=2.2, 8.5), 7.04 (1H, d, J=2.2), 6.87 (1H, d, J=8.5), 6.06 (1H, d, J=4.2), 3.94 (3H, s), 3.90 (3H, s), 3.29-3.43 (4H, m), 1.60-1.76 (6H, m)

Production of (Z)-2-(3,4-dimethoxy-phenyl)-3-(5-morpholin-4-yl-thiophen-2-yl)-acrylonitrile (Compound 5)

Through the procedure as employed in Production step 1, an amine moiety derived from morpholine (523 mg) was introduced into 5-bromothiophene-2-carboxaldehyde (382 mg), to thereby yield 5-morpholin-4-yl-thiophene-2-carbaldehyde (yield: 176 mg, 45%). The produced 5-morpholin-4-yl-thiophene-2-carbaldehyde (172 mg) was condensed with 3,4-dimethoxybenzyl cyanide (154 mg) through Method A (production step 2), to thereby yield the target product (yield: 46 mg, 15%).

Yellow Crystals

MS (ESI, m/z): 357 (M+H)$^+$ $^1$H-NMR (CDCl$_3$) δ: 7.38 (1H, s), 7.24 (1H, d, J=4.4), 7.14 (1H, dd, J=2.2, 8.3), 7.05 (1H, d, 2.2), 6.88 (1H, d, J=8.3), 6.08 (1H, d, J=4.4), 3.95 (3H, s), 3.91 (3H, s), 3.83-3.88 (4H, m), 3.28-3.33 (4H, m)

Production of (Z)-2-(3,4-dimethoxy-phenyl)-3-[5-(4-hydroxy-piperidin-1-yl)-thiophen-2-yl]-acrylonitrile (Compound 6)

Through the procedure as employed in Production step 1, an amine moiety derived from 4-hydroxypiperidine (3.03 g) was introduced into 5-bromothiophene-2-carboxaldehyde (1.91 g), to thereby yield 5-(4-hydroxypiperidin-1-yl)-thiophene-2-carbaldehyde (yield: 1.36 g, 64%). The produced 5-(4-hydroxypiperidin-1-yl)-thiophene-2-carbaldehyde (1.27 g) was condensed with 3,4-dimethoxybenzyl cyanide (1.06 g) through Method A (production step 2), to thereby yield the target product (yield: 1.09 g, 50%).

Yellow Crystals

MS (ESI, m/z): 371 (M+H)$^+$ $^1$H-NMR (CDCl$_3$) δ: 7.36 (1H, s), 7.22 (1H, d, J=4.4), 7.13 (1H, dd, J=2.2, 8.3), 7.04 (1H, d, J=2.2), 6.87 (1H, d, J=8.3), 6.04 (1H, d, J=4.4), 3.88-3.98 (1H, m), 3.94 (3H, s), 3.90 (3H, s), 3.60-3.67 (2H, m), 3.14-3.22 (2H, m), 1.98-2.06 (2H, m), 1.68-1.78 (2H, m)

Production of (Z)-2-(3,4-dimethoxy-phenyl)-3-{5-[(2-hydroxy-ethyl)-methyl-amino]-thiophen-2-yl}-acrylonitrile (Compound 7)

Through the procedure as employed in Production step 1, an amine moiety derived from N-methylethanolamine (2.25 g) was introduced into 5-bromothiophene-2-carboxaldehyde (1.91 g), to thereby yield 5-[(2-hydroxy-ethyl)-methyl-amino]-thiophene-2-carbaldehyde (yield: 991 mg, 53%). The produced 5-[(2-hydroxy-ethyl)-methyl-amino]-thiophene-2-carbaldehyde (682 mg) was condensed with 3,4-dimethoxybenzyl cyanide (654 mg) through Method A (production step 2), to thereby yield the target product (yield: 300 mg, 24%).

Orange Crystals

MS (ESI, m/z): 345 (M+H)$^+$ $^1$H-NMR (CDCl$_3$) δ: 7.35 (1H, s), 7.21 (1H, d, J=4.2), 7.12 (1H, dd, J=2.2, 8.3), 7.03 (1H, d, J=2.2), 6.87 (1H, d, J=8.3), 5.91 (1H, d, J=4.2), 3.94 (3H, s), 3.92 (2H, q, J=5.6), 3.90 (3H, s), 3.56 (2H, t, J=5.6), 3.15 (3H, s), 1.63 (1H, t, J=5.6)

Production of (Z)-2-(3,4-dimethoxy-phenyl)-3-[5-(4-methyl-piperazin-1-yl)-thiophen-2-yl]-acrylonitrile (Compound 8)

Through the procedure as employed in Production step 1, an amine moiety derived from 1-methylpiperazine (6.01 g) was introduced into 5-bromothiophene-2-carboxaldehyde (3.82 g), to thereby yield 5-(4-methyl-piperazin-1-yl)-thiophene-2-carbaldehyde (yield: 3.71 g, 88%). The produced 5-(4-methyl-piperazin-1-yl)-thiophene-2-carbaldehyde (2.10 g) was condensed with 3,4-dimethoxybenzyl cyanide (1.77 g) through Method A (production step 2), to thereby yield the target product (yield: 2.47 g, 67%).

Yellowish Orange Crystals

MS (ESI, m/z): 370 (M+H)$^+$ $^1$H-NMR (CDCl$_3$) δ: 7.37 (1H, s), 7.22 (1H, d, J=4.4), 7.13 (1H, dd, J=2.2, 8.5), 7.04 (1H, d, J=2.2), 6.87 (1H, d, J=8.5), 6.04 (1H, d, J=4.4), 3.94 (3H, s), 3.90 (3H, s), 3.33-3.37 (4H, m), 2.53-2.58 (4H, m), 2.36 (3H, s)

Production of (Z)-2-(3,4-dimethoxy-phenyl)-3-{5-[4-(2-hydroxy-ethyl)-piperazin-1-yl]-thiophen-2-yl}-acrylonitrile (Compound 9)

Through the procedure as employed in Production step 1, an amine moiety derived from 1-piperazineethanol (7.81 g) was introduced into 5-bromothiophene-2-carboxaldehyde (3.82 g), to thereby yield 5-[4-(2-hydroxy-ethyl)-piperazin-1-yl]-thiophene-2-carbaldehyde (yield: 3.22 g, 67%). The produced 5-[4-(2-hydroxy-ethyl)-piperazin-1-yl]-thiophene-2-carbaldehyde (1.85 g) was condensed with 3,4-dimethoxybenzyl cyanide (1.37 g) through Method A (production step 2), to thereby yield the target product (yield: 1.51 g, 49%).

Yellowish Orange Crystals

MS (ESI, m/z): 400 (M+H)$^+$ $^1$H-NMR (CDCl$_3$) δ: 7.37 (1H, s), 7.23 (1H, d, J=4.4), 7.13 (1H, dd, J=2.2, 8.3), 7.05 (1H, d, J=2.2), 6.88 (1H, d, J=8.3), 6.05 (1H, d, J=4.4), 3.95 (3H, s), 3.91 (3H, s), 3.67 (2H, m), 3.33-3.38 (4H, m), 2.65-2.70 (4H, m), 2.60-2.65 (2H, m), 2.57 (1H, m)

Production of (Z)-2-(3,4-dimethoxy-phenyl)-3-{5-[(2-dimethylamino-ethyl)-methyl-amino]-thiophen-2-yl}-acrylonitrile (Compound 10)

Through the procedure as employed in Production step 1, an amine moiety derived from N,N,N'-trimethylethylenediamine (6.13 g) was introduced into 5-bromothiophene-2-carboxaldehyde (3.82 g), to thereby yield 5-[(2-dimethylamino-ethyl)-methyl-amino]-thiophene-2-carbaldehyde (yield: 3.26 g, 77%). The produced 5-[(2-dimethylamino-ethyl)-methyl-amino]-thiophene-2-carbaldehyde (2.12 g) was condensed with 3,4-dimethoxybenzyl cyanide (1.77 g) through Method A (production step 2), to thereby yield the target product (yield: 1.20 g, 32%).

Yellowish Brown Oil

MS (ESI, m/z): 372 (M+H)$^+$ $^1$H-NMR (CDCl$_3$) δ: 7.34 (1H, s), 7.22 (1H, d, J=4.2), 7.11 (1H, dd, J=2.2, 8.3), 7.03 (1H, d, J=2.2), 6.87 (1H, d, J=8.3), 5.86 (1H, d, J=4.2), 3.94 (3H, s), 3.90 (3H, s), 3.48 (2H, t, J=7.1), 3.10 (3H, s), 2.56 (2H, t, J=7.1), 2.30 (6H, s)

Production of (Z)-2-(3,4-dimethoxy-phenyl)-3-(5-piperidin-1-yl-thiophen-2-yl)-acrylonitrile hydrochloride (Compound 11)

0.1N Hydrochloric acid (7.0 mL) was added to Compound 4 (226 mg), and purified water (30 mL), acetonitrile (30 mL), and chloroform (3 mL) were added to the mixture, to thereby dissolve the mixture. The solution was stirred at room temperature for 1 hour, and the solvent was evaporated to dryness. The residue was suspended in hexane-ethyl acetate, and the solvent was evaporated to dryness, followed by thoroughly drying, to thereby yield the target product (yield: 235 mg, 94%).

Yellow Crystals

MS (ESI, m/z): 355 (M−HCl+H)$^+$ $^1$H-NMR (CDCl$_3$) δ: 7.37 (1H, s), 7.23 (1H, brs), 7.13 (1H, dd, J=2.0, 8.5), 7.04 (1H, d, J=2.0), 6.87 (1H, d, J=8.5), 6.15 (1H, brs), 3.94 (3H, s), 3.90 (3H, s), 3.30-3.37 (4H, m), 1.72-1.80 (4H, m), 1.60-1.68 (2H, m)

Production of (Z)-2-(3,4-dimethoxy-phenyl)-3-[5-(4-hydroxy-piperidin-1-yl)-thiophen-2-yl]-acrylonitrile hydrochloride (Compound 12)

0.1N Hydrochloric acid (3.0 mL) was added to Compound 6 (100 mg), and purified water (5 mL), acetonitrile (30 mL), and chloroform (5 mL) were added to the mixture, to thereby dissolve the mixture. The solution was stirred at room temperature for 1 hour, and the solvent was evaporated to dryness, followed by thoroughly drying, to thereby yield the target product (yield: 95 mg, 87%).

Yellowish Orange Powder
MS (ESI, m/z): 371 (M−HCl+H)$^+$
$^1$H-NMR (DMSO-d$_6$) δ: 8.32 (1H, s), 7.89 (1H, s), 7.40 (1H, d, J=4.4), 7.16 (1H, d, J=2.0), 7.08 (1H, dd, J=2.0, 8.5), 7.00 (1H, d, J=8.5), 6.25 (1H, d, J=4.4), 4.82 (1H, d, J=3.9), 3.83 (3H, s), 3.77 (3H, s), 3.68-3.78 (1H, m), 3.50-3.60 (2H, m), 3.08-3.18 (2H, m), 1.80-1.90 (2H, m), 1.45-1.57 (2H, m)

Production of (Z)-2-(3,4-dimethoxy-phenyl)-3-[5-(4-methyl-piperazin-1-yl)-thiophen-2-yl]-acrylonitrile hydrochloride (Compound 13)

0.1N Hydrochloric acid (14.9 mL) was added to Compound 8 (500 mg) for dissolution, and purified water (10 mL) was added to the solution, followed by stirring at room temperature for 1 hour. The reaction mixture was lyophilized, to thereby yield the target product (yield: 546 mg, 99%).

Yellowish Orange Powder
MS (ESI, m/z): 370 (M−HCl+H)$^+$
$^1$H-NMR (CDCl$_3$) δ: 7.38 (1H, s), 7.21 (1H, d, J=4.1), 7.16 (1H, dd, J=2.2, 8.3), 7.05 (1H, d, J=2.2), 6.89 (1H, d, J=8.3), 6.16 (1H, d, J=4.1), 3.95 (3H, s), 3.92 (3H, s), 3.86-4.00 (2H, m), 3.65-3.78 (2H, m), 3.48-3.60 (2H, m), 2.98-3.11 (2H, m), 2.86 (3H, s)

Production of (Z)-2-(3,4-dimethoxy-phenyl)-3-{5-[4-(2-hydroxy-ethyl)-piperazin-1-yl]-thiophen-2-yl}-acrylonitrile hydrochloride (Compound 14)

0.1N Hydrochloric acid (13.8 mL) was added to Compound 9 (500 mg) for dissolution, and purified water (10 mL) was added to the solution, followed by stirring at room temperature for 1 hour. The reaction mixture was lyophilized, to thereby yield the target product (yield: 540 mg, 99%).

Yellowish Orange Powder
MS (ESI, m/z): 400 (M−HCl+H)$^+$
$^1$H-NMR (CDCl$_3$) δ: 7.39 (1H, s), 7.22 (1H, d, J=4.1), 7.16 (1H, dd, J=2.2, 8.3), 7.05 (1H, d, J=2.2), 6.89 (1H, d, J=8.3), 6.16 (1H, d, J=4.2), 4.05-4.15 (2H, m), 3.95 (3H, s), 3.92 (3H, s), 3.90-4.05 (2H, m), 3.65-3.83 (4H, m), 3.05-3.25 (4H, m)

Production of (Z)-2-(3,4-dimethoxy-phenyl)-3-{5-[(2-dimethylamino-ethyl)-methyl-amino]-thiophen-2-yl}-acrylonitrile hydrochloride (Compound 15)

0.1N Hydrochloric acid (3.0 mL) was added to Compound 10 (100 mg), and purified water (5 mL) and acetonitrile (5 mL) were added to the mixture, to thereby dissolve the mixture. The solution was stirred at room temperature for 1 hour, and the solvent was evaporated to dryness, followed by thoroughly drying, to thereby yield the target product (yield: 100 mg, 91%).

Orange Powder
MS (ESI, m/z): 372 (M−HCl+H)$^+$
$^1$H-NMR (CDCl$_3$) δ: 7.38 (1H, s), 7.21 (1H, d, J=4.1), 7.13 (1H, dd, J=2.2, 8.3), 7.03 (1H, d, J=2.2), 6.88 (1H, d, J=8.3), 6.09 (1H, d, J=4.1), 4.00-4.06 (2H, m), 3.95 (3H, s), 3.91 (3H, s), 3.24-3.30 (2H, m), 3.18 (3H, s), 2.90 (3H, s), 2.88 (3H, s)

Production of mono-(1-{5-[(Z)-2-cyano-2-(3,4-dimethoxy-phenyl)-vinyl]-thiophen-2-yl}-piperidin-4-yl)phosphate (Compound 16)

Compound 6 (400 mg) and bis(2,2,2-trichloroethyl)phosphorochloridate (1.64 g) were dissolved in pyridine (4 mL), and the solution was stirred at room temperature for 2 hours. After completion of reaction, methanol was added to the reaction mixture, followed by stirring for 30 minutes. The solvent was evaporated to dryness, and the residue was purified by silica gel column chromatography (ethyl acetate:hexane=7:13), to thereby yield 1-{5-[(Z)-2-cyano-2-(3,4-dimethoxy-phenyl)-vinyl]-thiophen-2-yl}-piperidin-4-yl bis-(2,2,2-trichloro-ethyl)phosphate (yield: 694 mg, 90%).

The produced 1-{5-[(Z)-2-cyano-2-(3,4-dimethoxy-phenyl)-vinyl]-thiophen-2-yl}-piperidin-4-yl bis-(2,2,2-trichloro-ethyl)phosphate (385 mg) was dissolved in a solvent mixture (5 mL) of pyridine and acetic acid (4:1). Zinc powder (353 mg) was added to the solution, followed by stirring at room temperature for 4 hours. Insoluble zinc powder was removed through filtration, and an IRC748 (NH$_4^+$) resin (11 g) was added to the filtrate, followed by stirring at room temperature for 30 minutes. Resinous material was removed through filtration, and the solvent was evaporated to dryness. The residue was washed with ethanol, to thereby yield the target product (yield: 195 mg, 80%).

Yellowish Brown Powder
MS (ESI, m/z): 449 (M−H)$^−$
$^1$H-NMR (DMSO) δ: 1.71-1.77 (2H, m), 1.96-1.99 (2H, m), 3.23-3.28 (2H, m), 3.50-3.56 (2H, m), 3.77 (3H, s), 3.83 (3H, s), 4.27-4.30 (1H, m), 6.28 (1H, d, J=3.9), 7.01 (1H, d, J=8.8), 7.08 (1H, dd, J=2.0, 8.3), 7.16 (1H, d, J=2.0), 7.91 (1H, s), 8.58 (1H, d, J=3.9)

Production of mono-(1-{5-[(Z)-2-cyano-2-(3,4-dimethoxy-phenyl)-vinyl]-thiophen-2-yl}-piperidin-4-yl)phosphate sodium salt (Compound 17)

Purified water (10 mL) was added to Compound 16 (100 mg) to form suspension. An IRC748 (Na) resin (2 g) was added to the suspension, followed by stirring at room temperature. After dissolution of starting materials, resinous material was removed through filtration, and the solvent was evaporated under reduced pressure, to thereby yield the target product (yield: 104 mg, 95%).

Yellowish Brown Powder
MS (ESI, m/z): 449 (M−2Na+H)$^−$
$^1$H-NMR (D$_2$O) δ: 7.13 (1H, s), 6.90 (1H, d, J=2.2), 6.60-6.75 (3H, m), 5.96 (1H, d, J=4.1), 4.05-4.08 (1H, m), 3.64 (3H, s), 3.63 (3H, s), 3.42-3.45 (2H, m), 2.69-3.01 (2H, m), 1.91-1.92 (2H, m), 1.57-1.59 (2H, m)

Production of mono-(1-{5-[(Z)-2-cyano-2-(3,4-dimethoxy-phenyl)-vinyl]-thiophen-2-yl}-piperidin-4-yl)succinate (Compound 18)

Compound 6 (200 mg) was dissolved in pyridine (2 mL), and succinic anhydride (270 mg) was added to the solution, followed by stirring under reflux for 2 hours. After completion of reaction, methanol was added to the reaction mixture, followed by stirring for 30 minutes. The solvent was evaporated to dryness, and the residue was extracted with chloroform and purified water. The organic layer was dried over sodium sulfate anhydrate, and the solvent was evaporated to dryness. The residue was washed with hexane, to thereby yield the target product (yield: 212 mg, 95%).
Yellow Powder
MS (ESI, m/z): 469 (M−H)⁻
¹H-NMR (CDCl$_3$) δ: 7.36 (1H, s), 7.22 (1H, d, J=4.1), 7.13 (1H, dd, J=2.2, 8.5), 7.04 (1H, d, J=2.2), 6.87 (1H, d, J=8.5), 6.05 (1H, d, J=4.1), 5.02-5.04 (1H, m), 3.94 (3H, s), 3.90 (3H, s), 3.50-3.55 (2H, m), 3.25-3.32 (2H, m), 2.69-2.72 (2H, m), 2.64-2.67 (2H, m), 2.00-2.05 (2H, m), 1.83-1.89 (2H, m)

Production of (Z)-2-(3,4-dimethoxy-phenyl)-3-(5-nitro-furan-2-yl)-acrylonitrile (Compound 19)

5-Nitro-2-furaldehyde (1.41 g) was condensed with 3,4-dimethoxybenzyl cyanide (1.77 g) through Method A (production step 2), to thereby yield the target product (yield: 88 mg, 2.9%).
Orange Crystals
MS (APCI, m/z): 300 (M)⁻
¹H-NMR (CDCl$_3$) δ: 7.53 (1H, d, J=3.9), 7.46 (1H, d, J=3.9), 7.36 (1H, s), 7.32 (1H, dd, J=2.4, 8.3), 7.13 (1H, d, J=2.4), 6.95 (1H, d, J=8.3), 3.97 (3H, s), 3.95 (3H, s)

Production of (Z)-2-(3,4-dimethoxy-phenyl)-3-(5-hydroxy-methyl-furan-2-yl)-acrylonitrile (Compound 20)

5-Acetoxymethyl-2-furaldehyde (505 mg) was condensed with 3,4-dimethoxybenzyl cyanide (532 mg) through Method A (production step 2), to thereby yield the target product (yield: 726 mg, 85%).
Orange Crystals
MS (ESI, m/z): 284 (M−H)⁻
¹H-NMR (CDCl$_3$) δ: 7.26 (1H, s), 7.22 (1H, dd, J=2.4, 8.5), 7.12 (1H, d, J=3.7), 7.09 (1H, d, J=2.4), 6.91 (1H, d, J=8.5), 6.48 (1H, d, J=3.7), 4.49 (2H, d, J=6.3), 3.85 (3H, s), 3.80 (3H, s)

Production of (Z)-2-(3,4-dimethoxy-phenyl)-3-[5-(3-nitro-phenyl)-furan-2-yl]-acrylonitrile (Compound 21)

5-(3-Nitrophenyl)furfural (1.09 g) was condensed with 3,4-dimethoxybenzyl cyanide (889 mg) through Method A (production step 2), to thereby yield the target product (yield: 1.85 g, 98%).
Yellowish Orange Crystals
MS (APCI, m/z): 376 (M)⁻
¹H-NMR (CDCl$_3$) δ: 8.61 (1H, t, J=2.0), 8.17 (1H, dd, J=2.0, 8.1), 8.16 (1H, dd, J=2.0, 8.1), 7.64 (1H, t, J=8.1), 7.31 (1H, s), 7.30 (1H, dd, J=2.2, 8.5), 7.16 (1H, d, J=3.7), 7.15 (1H, d, J=2.2), 7.00 (1H, d, J=3.7), 6.94 (1H, d, J=8.5), 3.99 (3H, s), 3.94 (3H, s)

Production of (Z)-3-[5-(3-amino-phenyl)-furan-2-yl]-2-(3,4-dimethoxy-phenyl)-acrylonitrile (Compound 22)

Acetic acid (300 mL) was added to Compound 21 (1.00 g) to form suspension. Zinc powder (3.47 g) was added to the suspension, followed by stirring at room temperature for 4 hours. The reaction mixture was subjected to filtration by use of a celite pad, and the celite pad was washed with chloroform. The filtrate (acetic acid-chloroform solution) was evaporated to dryness. The residue was purified by silica gel column chromatography (chloroform-methanol), to thereby yield the target product (yield: 184 mg, 24%).
Yellow Crystals
MS (ESI, m/z): 347 (M+H)⁺
¹H-NMR (CDCl$_3$) δ: 7.24-7.28 (2H, m), 7.18-7.23 (3H, m), 7.14 (1H, d, J=2.4), 7.08 (1H, d, J=3.9), 6.92 (1H, d, J=8.8), 6.79 (1H, d, J=3.9), 6.65-6.68 (1H, m), 3.97 (3H, s), 3.93 (3H, s)

Production of (Z)-3-[5-(3-amino-phenyl)-furan-2-yl]-2-(3,4-dimethoxy-phenyl)-acrylonitrile hydrochloride (Compound 23)

0.1N Hydrochloric acid (3.7 mL) was added to Compound 22 (117 mg), and purified water (30 mL), acetonitrile (30 mL), and chloroform (5 mL) were added to the mixture, to thereby dissolve the mixture. The solution was stirred at room temperature for 1 hour, and the solvent was evaporated to dryness. The residue was suspended in hexane-ethyl acetate, and the solvent was evaporated to dryness, followed by thoroughly drying, to thereby yield the target product (yield: 124 mg, 96%).
Yellowish Brown Powder
MS (ESI, m/z): 347 (M−HCl+H)⁺
¹H-NMR (DMSO-d$_6$) δ: 7.88 (1H, s), 7.75 (1H, brd, J=7.9), 7.63 (1H, brs), 7.53 (1H, t, J=7.9), 7.35 (1H, d, J=2.2), 7.22-7.28 (3H, m), 7.17 (1H, d, J=3.7), 7.09 (1H, d, J=8.8), 3.87 (3H, s), 3.82 (3H, s)

Production of (Z)-2-(3,4-dimethoxy-phenyl)-3-(5-piperidin-1-yl-furan-2-yl)-acrylonitrile (Compound 24)

Through the procedure as employed in Production step 1, an amine moiety derived from piperidine (1.28 g) was introduced into 5-bromo-2-furaldehyde (875 mg), to thereby yield 5-piperidin-1-yl-furan-2-carbaldehyde (yield: 650 mg, 73%). The produced 5-piperidin-1-yl-furan-2-carbaldehyde (179 mg) was condensed with 3,4-dimethoxybenzyl cyanide (177 mg) through Method A (production step 2), to thereby yield the target product (yield: 100 mg, 30%).
Orange Crystals
MS (ESI, m/z): 339 (M+H)⁺
¹H-NMR (CDCl$_3$) δ: 7.13 (1H, dd, J=2.2, 8.5), 7.05 (1H, d, J=2.2), 6.94 (1H, s), 6.87 (1H, d, J=8.5), 6.84 (1H, d, J=3.4), 5.24 (1H, d, J=3.4), 3.94 (3H, s), 3.90 (3H, s), 3.37-3.42 (4H, m), 1.61-1.72 (6H, m)

Production of (Z)-2-(3,4-dimethoxy-phenyl)-3-(5-morpholin-4-yl-furan-2-yl)-acrylonitrile (Compound 25)

Through the procedure as employed in Production step 1, an amine moiety derived from morpholine (523 mg) was introduced into 5-bromo-2-furaldehyde (350 mg), to thereby yield 5-morpholin-4-yl-furan-2-carbaldehyde (yield: 138 mg, 38%). The produced 5-morpholin-4-yl-furan-2-carbaldehyde (137 mg) was condensed with 3,4-dimethoxybenzyl cyanide (135 mg) through Method A (production step 2), to thereby yield the target product (yield: 102 mg, 40%).
Yellow Crystals
MS (ESI, m/z): 341 (M+H)⁺
¹H-NMR (CDCl$_3$) δ: 7.14 (1H, dd, J=2.2, 8.5), 7.05 (1H, d, J=2.2), 6.96 (1H, s), 6.88 (1H, d, J=8.5), 6.82 (1H, d, J=3.7), 5.29 (1H, d, J=3.7), 3.94 (3H, s), 3.91 (3H, s), 3.82-3.86 (4H, m), 3.37-3.42 (4H, m)

Production of (Z)-2-(3,4-dimethoxy-phenyl)-3-[5-(4-hydroxy-piperidin-1-yl)-furan-2-yl]-acrylonitrile (Compound 26)

Through the procedure as employed in Production step 1, an amine moiety derived from 4-hydroxypiperidine (1.52 g) was introduced into 5-bromo-2-furaldehyde (875 mg), to thereby yield 5-(4-hydroxy-piperidin-1-yl)-furan-2-carbaldehyde (yield: 660 mg, 68%). The produced 5-(4-hydroxy-piperidin-1-yl)-furan-2-carbaldehyde (390 mg) was condensed with 3,4-dimethoxybenzyl cyanide (354 mg) through Method A (production step 2), to thereby yield the target product (yield: 458 mg, 65%).

Orange Crystals
MS (ESI, m/z): 355 (M+H)$^+$
$^1$H-NMR (CDCl$_3$) δ: 7.13 (1H, dd, J=2.2, 8.3), 7.05 (1H, d, J=2.2), 6.94 (1H, s), 6.87 (1H, d, J=8.3), 6.83 (1H, d, J=3.7), 5.28 (1H, d, J=3.7), 3.88-3.96 (1H, m), 3.93 (3H, s), 3.90 (3H, s), 3.77-3.82 (2H, m), 3.15-3.23 (2H, m), 1.97-2.05 (2H, m), 1.63-1.73 (2H, m)

Production of (Z)-2-(3,4-dimethoxy-phenyl)-3-[5-(4-methyl-piperazin-1-yl)-furan-2-yl]-acrylonitrile (Compound 27)

Through the procedure as employed in Production step 1, an amine moiety derived from 1-methylpiperazine (1.03 g) was introduced into 5-bromo-2-furaldehyde (602 mg), to thereby yield 5-(4-methyl-piperazin-1-yl)-furan-2-carbaldehyde (yield: 447 mg, 67%). The produced 5-(4-methyl-piperazin-1-yl)-furan-2-carbaldehyde (388 mg) was condensed with 3,4-dimethoxybenzyl cyanide (355 mg) through Method A (production step 2), to thereby yield the target product (yield: 215 mg, 30%).

Yellow Crystals
MS (ESI, m/z): 354 (M+H)$^+$
$^1$H-NMR (CDCl$_3$) δ: 7.14 (1H, dd, J=2.2, 8.5), 7.05 (1H, d, J=2.2), 6.95 (1H, s), 6.87 (1H, d, J=8.5), 6.83 (1H, d, J=3.7), 5.28 (1H, d, J=3.7), 3.94 (3H, s), 3.90 (3H, s), 3.41-3.48 (4H, m), 2.50-2.56 (4H, m), 2.35 (3H, s)

Production of (Z)-2-(3,4-dimethoxy-phenyl)-3-{5-[4-(2-hydroxy-ethyl)-piperazin-1-yl]-furan-2-yl}-acrylonitrile (Compound 28)

Through the procedure as employed in Production step 1, an amine moiety derived from 1-piperazineethanol (3.91 g) was introduced into 5-bromo-2-furaldehyde (1.75 g), to thereby yield 5-[(4-(2-hydroxy-ethyl)-piperazin-1-yl)-furan-2-carbaldehyde (yield: 1.37 g, 61%). The produced 5-[(4-(2-hydroxy-ethyl)-piperazin-1-yl)-furan-2-carbaldehyde (1.12 g) was condensed with 3,4-dimethoxybenzyl cyanide (888 mg) through Method A (production step 2), to thereby yield the target product (yield: 1.32 g, 69%).

Yellowish Brown Oil
MS (ESI, m/z): 384 (M+H)$^+$
$^1$H-NMR (CDCl$_3$) δ: 7.14 (1H, dd, J=2.2, 8.5), 7.05 (1H, d, J=2.2), 6.96 (1H, s), 6.87 (1H, d, J=8.5), 6.82 (1H, d, J=3.7), 5.28 (1H, d, J=3.7), 3.94 (3H, s), 3.90 (3H, s), 3.63-3.69 (2H, m), 3.42-3.48 (4H, m), 2.58-2.68 (6H, m)

Production of (Z)-2-(3,4-dimethoxy-phenyl)-3-[5-(4-methyl-piperazin-1-yl)-furan-2-yl]-acrylonitrile hydrochloride (Compound 29)

0.1N Hydrochloric acid (3.1 mL) was added to Compound 27 (100 mg) for dissolution, and purified water (5 mL) was added to the solution, followed by stirring at room temperature for 30 minutes. The reaction mixture was lyophilized, to thereby yield the target product (yield: 109 mg, 99%).

Yellowish Brown Powder
MS (ESI, m/z): 354 (M−HCl+H)$^+$
$^1$H-NMR (CDCl$_3$) δ: 7.16 (1H, dd, J=2.2, 8.5), 7.05 (1H, d, J=2.2), 6.98 (1H, s), 6.89 (1H, d, J=8.5), 6.77 (1H, d, J=3.7), 5.41 (1H, d, J=3.7), 3.94 (3H, s), 3.91 (3H, s), 3.85-3.95 (4H, m), 3.50-3.58 (2H, m), 2.97-3.08 (2H, m), 2.86 (3H, s)

Production of (Z)-2-(3,4-dimethoxy-phenyl)-3-pyridin-4-yl-acrylonitrile (Compound 30)

4-Pyridinecarboxaldehyde (2.14 g) was condensed with 3,4-dimethoxybenzyl cyanide (3.54 g) through Method A (production step 2), to thereby yield the target product (yield: 3.36 g, 63%).

Slightly Yellow Crystals
MS (ESI, m/z): 267 (M+H)$^+$
$^1$H-NMR (CDCl$_3$) δ: 8.73 (2H, d, J=6.3), 7.69 (2H, d, J=6.3), 7.36 (1H, s), 7.31 (1H, dd, J=2.4, 8.8), 7.17 (1H, d, J=2.4), 6.95 (1H, d, J=8.8), 3.97 (3H, s), 3.95 (3H, s)

Production of (Z)-2-(3,4-dimethoxy-phenyl)-3-pyridin-4-yl-acrylonitrile hydrochloride (Compound 31)

0.1N Hydrochloric acid (12.4 mL) was added to Compound 30 (300 mg), and purified water (25 mL) and acetonitrile (20 mL) were added the mixture, to thereby dissolve the mixture. The solution was stirred in the dark at room temperature for 4 hours, and the solvent was evaporated to dryness. The residue was suspended in hexane-ethyl acetate, and the solvent was evaporated to dryness, followed by thoroughly drying, to thereby yield the target product (yield: 333 mg, 98%).

Yellowish Orange Powder
MS (ESI, m/z): 267 (M−HCl+H)$^+$
$^1$H-NMR (DMSO-d$_6$) δ: 8.94 (2H, d, J=5.4), 8.20 (3H, brs), 7.46 (1H, d, J=2.2), 7.39 (1H, dd, J=2.2, 8.5), 7.15 (1H, d, J=8.5), 3.88 (3H, s), 3.85 (3H, s)

Production of (Z)-2-(3,4-dimethoxy-phenyl)-3-pyridin-4-yl-acrylonitrile methanesulfonate (Compound 32)

0.1-mol/L Aqueous methanesulfonic acid solution (10.0 mL) was added to Compound 30 (266 mg), and purified water (10 mL) and acetonitrile (5 mL) were added to the mixture, to thereby dissolve the mixture. The solution was stirred in the dark at room temperature for 3 hours, and the solvent was evaporated to dryness. The residue was suspended in methanol, and the solvent was evaporated to dryness, followed by thoroughly drying, to thereby yield the target product (yield: 350 mg, 97%).

Yellowish Orange Crystals
MS (ESI, m/z): 267 (M−CH$_3$SO$_3$H+ H)$^+$
$^1$H-NMR (DMSO-d$_6$) δ: 9.01 (2H, d, J=6.8), 8.35 (2H, d, J=6.8), 8.22 (1H, s), 7.45 (1H, d, J=2.0), 7.39 (1H, dd, J=2.0, 8.3), 7.14 (1H, d, J=8.3), 3.87 (3H, s), 3.83 (3H, s), 2.40 (3H, s)

Production of (Z)-2-(3,4-dimethoxy-phenyl)-3-pyridin-4-yl-acrylonitrile N-oxide (Compound 33)

Compound 30 (266 mg) was dissolved in anhydrous dichloromethane (50 mL). m-chloroperoxybenzoic acid (266 mg) was added dropwise to the solution under stirring in an ice bath. The mixture was stirred for about 15 minutes under argon which was fed by means of a separately provided balloon filled with argon. The mixture was returned to room temperature, followed by stirring for 3 hours. The reaction mixture was extracted with purified water and chloroform. The organic layer was washed with brine, and the washed organic layer was dried over sodium sulfate anhydrate. The solvent was evaporated to dryness. The residue was purified by silica gel column chromatography (chloroform-methanol), to thereby yield the target product (yield: 265 mg, 94%).

Yellow Crystals

MS (ESI, m/z) 283 (M+H)$^+$ $^1$H-NMR (CDCl$_3$) δ: 8.23 (2H, d, J=7.3), 7.79 (2H, d, J=7.3), 7.29 (1H, dd, J=2.4, 8.3), 7.26 (1H, s), 7.13 (1H, d, J=2.4), 6.94 (1H, d, J=8.3), 3.97 (3H, s), 3.95 (3H, s)

Production of (Z)-2-(3,4-dimethoxy-phenyl)-3-pyridin-3-yl-acrylonitrile (Compound 34)

3-Pyridinecarboxaldehyde (2.14 g) was condensed with 3,4-dimethoxybenzyl cyanide (3.54 g) through Method A (production step 2), to thereby yield the target product (yield: 4.79 g, 90%).

Slightly Yellow Crystals

MS (ESI, m/z): 267 (M+H)$^+$ $^1$H-NMR (CDCl$_3$) δ: 8.83 (1H, d, J=2.4), 8.64 (1H, dd, J=1.5, 4.9), 8.44-8.48 (1H, m), 7.40-7.45 (2H, m), 7.30 (1H, dd, J=2.0, 8.3), 7.16 (1H, d, J=2.0), 6.94 (1H, d, J=8.3), 3.98 (3H, s), 3.95 (3H, s)

Production of (Z)-2-(3,4-dimethoxy-phenyl)-3-(6-methoxy-pyridin-3-yl)-acrylonitrile (Compound 35)

6-Methoxy-3-pyridinecarboxaldehyde (411 mg) was condensed with 3,4-dimethoxybenzyl cyanide (532 mg) through Method A (production step 2), to thereby yield the target product (yield: 850 mg, 96%).

Slightly Yellow Crystals

MS (ESI, m/z): 297 (M+H)$^+$ $^1$H-NMR (CDCl$_3$) δ: 8.40-8.45 (1H, m), 8.42 (1H, s), 7.34 (1H, s), 7.25 (1H, dd, J=2.2, 8.5), 7.13 (1H, d, J=2.2), 6.92 (1H, d, J=8.5), 6.85 (1H, m), 4.00 (3H, s), 3.97 (3H, s), 3.93 (3H, s)

Production of (Z)-2-(3,4-dimethoxy-phenyl)-3-pyridin-3-yl-acrylonitrile hydrochloride (Compound 36)

0.1N Hydrochloric acid (21.0 mL) was added to Compound 34 (500 mg), and purified water (40 mL), acetonitrile (50 mL), and chloroform (1 mL) were added to the mixture, to thereby dissolve the mixture. The solution was stirred in the dark at room temperature for 3 hours, and the solvent was evaporated to dryness. The precipitated crystals were thoroughly dried, to thereby yield the target product (yield: 550 mg, 97%).

Yellow Crystals

MS (ESI, m/z): 267 (M−HCl+H)$^+$ $^1$H-NMR (DMSO-d$_6$) δ: 9.12 (1H, brs), 8.80 (1H, brd, J=4.8), 8.65 (1H, brd, J=8.3), 8.14 (1H, s), 7.88 (1H, m), 7.40 (1H, d, J=2.4), 7.32 (1H, dd, J=2.4, 8.5), 7.13 (1H, d, J=8.8), 3.88 (3H, s), 3.83 (3H, s)

Production of (Z)-2-(3,4-dimethoxy-phenyl)-3-(6-methoxy-pyridin-3-yl)-acrylonitrile hydrochloride (Compound 37)

0.1N Hydrochloric acid (2.0 mL) was added to Compound 35 (50 mg), and purified water (8 mL) and acetonitrile (8 mL) were added to the mixture, to thereby dissolve the mixture. The solution was stirred in the dark at room temperature for 4 hours, and the solvent was evaporated to dryness. The precipitated crystals were thoroughly dried, to thereby yield the target product (yield: 55 mg, 98%).

Yellow Powder

MS (ESI, m/z): 297 (M−HCl+H)$^+$ $^1$H-NMR (DMSO-d$_6$) δ: 8.63 (1H, d, J=2.4), 8.35 (1H, dd, J=2.4, 8.8), 7.33 (1H, d, J=2.2), 7.25 (1H, dd, J=2.2, 8.5), 7.08 (1H, d, J=8.5), 7.02 (1H, d, J=8.8), 3.93 (3H, s), 3.86 (3H, s), 3.81 (3H, s)

Production of (Z)-2-(3,4-dimethoxy-phenyl)-3-pyridin-2-yl-acrylonitrile (Compound 38)

2-Pyridinecarboxaldehyde (2.14 g) was condensed with 3,4-dimethoxybenzyl cyanide (3.54 g) through Method A (production step 2), to thereby yield the target product (yield: 3.77 g, 71%).

Slightly Yellow Crystals

MS (ESI, m/z): 267 (M+H)$^+$ $^1$H-NMR (CDCl$_3$) δ: 8.73-8.77 (1H, m), 8.01 (1H, d, J=8.3), 7.8 (1H, m), 7.57 (1H, s), 7.36 (1H, dd, J=2.2, 8.5), 7.31 (1H, dd, J=4.9, 7.8), 7.23 (1H, d, J=2.4), 6.94 (1H, d, J=8.3), 3.96 (3H, s), 3.94 (3H, s)

Production of (Z)-2-(3,4-dimethoxy-phenyl)-3-(1H-pyrrol-2-yl)-acrylonitrile (Compound 39)

Pyrrole-2-carboxaldehyde (951 mg) was dissolved in dichloromethane (50 mL), and di-t-butyl dicarbonate (2.40 g), 4-dimethoxyaminopyridine (61 mg), and triethylamine (1.01 g) were added to the solution, followed by stirring at room temperature for 30 minutes. The solvent was evaporated to dryness, and the residue was purified by silica gel column chromatography (chloroform), to thereby yield t-butyl 2-formyl-pyrrole-1-carboxylate (yield: 1.95 g, ca. 100%). The produced t-butyl 2-formyl-pyrrole-1-carboxylate (976 mg) was condensed with 3,4-dimethoxybenzyl cyanide (886 mg) through Method A (production step 2), to thereby yield the target product (yield: 300 mg, 24%).

Yellow Powder

MS (ESI, m/z): 253 (M−H)$^-$ $^1$H-NMR (CDCl$_3$) δ: 9.74 (1H, brs), 7.28 (1H, s), 7.15 (1H, dd, J=2.2, 8.3), 7.05 (2H, m), 6.90 (1H, d, J=8.3), 6.63-6.68 (1H, m), 6.32-6.36 (1H, m), 3.95 (3H, s), 3.92 (3H, s)

Production of (Z)-2-(3,4-dimethoxy-phenyl)-3-(1H-pyrrol-2-yl)-acrylonitrile hydrochloride (Compound 40)

0.1N Hydrochloric acid (4.3 mL) was added to Compound 39 (100 mg), and acetonitrile (20 mL) was added to the mixture, to thereby dissolve the mixture. The solution was stirred in the dark at room temperature for 2.5 hours, and the solvent was evaporated to dryness. The precipitated crystals were thoroughly dried, to thereby yield the target product (yield: 100 mg, 88%).

Yellow Powder

MS (ESI, m/z): 253 (M−HCl−H)$^-$ $^1$H-NMR (DMSO-d$_6$) δ: 11.38 (1H, brs), 7.63 (1H, s), 7.02-7.17 (5H, m), 6.28-6.32 (1H, m), 3.83 (3H, s), 3.79 (3H, s)

Production of (Z)-2-(3,4-dimethoxy-phenyl)-3-(3H-imidazol-4-yl)-acrylonitrile (Compound 41)

4(5)-Imidazolecarboxaldehyde (285 mg) was condensed with 3,4-dimethoxybenzyl cyanide (532 mg) through Method A (production step 2), to thereby yield the target product (yield: 75 mg, 10%).
Slightly Yellow Powder
MS (ESI, m/z): 256 (M+H)$^+$
$^1$H-NMR (DMSO-d$_6$) δ: 12.5 (1H, brs), 7.86 (1H, s), 7.75 (1H, d, J=3.9), 7.25 (1H, d, J=2.2), 7.18 (1H, dd, J=2.2, 8.5), 7.04 (1H, d, J=8.5), 3.84 (3H, s), 3.79 (3H, s)

Production of (Z)-3-(3-benzyl-2-methylsulfanyl-3H-imidazol-4-yl)-2-(3,4-dimethoxy-phenyl)-acrylonitrile (Compound 42)

1-Benzyl-2-(methylsulfanyl)-1H-imidazole-5-carbaldehyde (465 mg) was condensed with 3,4-dimethoxybenzyl cyanide (354 mg) through Method A (production step 2), to thereby yield the target product (yield: 723 mg, 92%).
Yellow Powder
MS (ESI, m/z): 392 (M+H)$^+$
$^1$H-NMR (CDCl$_3$) δ: 8.24 (1H, s), 7.40-7.30 (3H, m), 7.14-7.10 (2H, m), 6.99 (1H, dd, J=2.2, 8.5), 6.94 (1H, d, J=1.0), 6.83 (1H, d, J=8.5), 6.78 (1H, d, J=2.2), 5.23 (2H, s), 3.89 (3H, s), 3.84 (3H, s), 2.72 (3H, s)

Production of (Z)-2-(3,4-dimethoxy-phenyl)-3-(4-methyl-2-phenyl-thiazol-5-yl)-acrylonitrile (Compound 43)

4-Methyl-2-phenyl-1,3-thiazole-5-carbaldehyde (407 mg) was condensed with 3,4-dimethoxybenzyl cyanide (354 mg) through Method A (production step 2), to thereby yield the target product (yield: 667 mg, 92%).
Yellow Powder
MS (ESI, m/z): 363 (M+H)$^+$
$^1$H-NMR (CDCl$_3$) δ: 8.06-8.00 (2H, m), 7.56 (1H, s), 7.49-7.44 (3H, m), 7.25 (1H, dd, J=2.2, 8.5), 7.13 (1H, d, J=2.2), 6.93 (1H, d, J=8.5), 3.97 (3H, s), 3.94 (3H, s), 2.65 (3H, s)

Production of (Z)-3-(3,4-dimethoxy-phenyl)-2-pyridin-3-yl-acrylonitrile (Compound 44)

3-Pyridineacetonitrile (1.18 g) was condensed with 3,4-dimethoxybenzaldehyde (1.66 g) through Method B (production step 2), to thereby yield the target product (yield: 1.96 g, 74%).
Slightly Yellow Crystals
MS (ESI, m/z): 267 (M+H)$^+$
$^1$H-NMR (CDCl$_3$) δ: 8.91 (1H, d, J=2.7), 8.61 (1H, dd, J=1.5, 4.9), 7.92-7.97 (1H, m), 7.74 (1H, d, J=2.2), 7.49 (1H, s), 7.36-7.41 (2H, m), 6.95 (1H, d, J=8.5), 3.98 (3H, s), 3.96 (3H, s)

Production of (Z)-3-(3,4-dimethoxy-phenyl)-2-pyridin-2-yl-acrylonitrile (Compound 45)

2-Pyridineacetonitrile (1.18 g) was condensed with 3,4-dimethoxybenzaldehyde (1.66 g) through Method B (production step 2), to thereby yield the target product (yield: 2.06 g, 77%).
Slightly Yellow Crystals
MS (ESI, m/z): 267 (M+H)$^+$
$^1$H-NMR (CDCl$_3$) δ: 8.61-8.65 (1H, m), 8.41 (1H, s), 7.73-7.81 (3H, m), 7.52 (1H, dd, J=2.1, 8.3), 7.28 (1H, m), 6.96 (1H, d, J=8.3), 3.98 (3H, s), 3.96 (3H, s)

Production of (Z)-3-(3,4-dimethoxy-phenyl)-2-pyridin-3-yl-acrylonitrile hydrochloride (Compound 46)

0.1N Hydrochloric acid (8.3 mL) was added to Compound 44 (200 mg) for dissolution, and purified water (5 mL) was added to the solution, followed by stirring at room temperature for 20 minutes. The reaction mixture was lyophilized, to thereby yield the target product (yield: 224 mg, 99%).
Yellow Powder
MS (ESI, m/z): 267 (M−HCl+H)$^+$
$^1$H-NMR (DMSO-d$_6$) δ: 9.04 (1H, d, J=1.7), 8.71 (1H, dd, J=1.5, 5.1), 8.33-8.38 (1H, m), 8.16 (1H, s), 7.76 (1H, dd, J=5.1, 8.1), 7.70 (1H, d, J=2.2), 7.60 (1H, dd, J=2.2, 8.5), 7.17 (1H, d, J=8.5), 3.85 (3H, s), 3.82 (3H, s)

Production of (Z)-3-(3,4-dimethoxy-phenyl)-2-pyridin-2-yl-acrylonitrile hydrochloride (Compound 47)

0.1N Hydrochloric acid (4.1 mL) was added to Compound 45 (100 mg), and acetonitrile (20 mL) was added to the mixture, to thereby dissolve the mixture. The solution was stirred in the dark at room temperature for 1 hour, and the solvent was evaporated to dryness. The precipitated crystals were thoroughly dried, to thereby yield the target product (yield: 112 mg, 99%).
Yellow Powder
MS (ESI, m/z): 267 (M−HCl+H)$^+$
$^1$H-NMR (DMSO-d$_6$) δ: 8.63-8.67 (1H, m), 8.41 (1H, s), 7.92-7.98 (1H, m), 7.82 (1H, d, J=8.3), 7.76 (1H, d, J=2.0), 7.66 (1H, dd, J=2.0, 8.3), 7.43 (1H, dd, J=4.8, 7.4), 7.16 (1H, d, J=8.3), 3.86 (3H, s), 3.83 (3H, s)

Production of (Z)-2-(3,4-dimethoxy-phenyl)-3-{5-[(2-dimethylamino-ethyl)-methyl-amino]-furan-2-yl}-acrylonitrile (Compound 48)

Through the procedure as employed in Production step 1, an amine moiety derived from N,N,N'-trimethylethylenediamine (3.06 g) was introduced into 5-bromo-2-furaldehyde (1.75 g), to thereby yield 5-(4-methyl-piperazin-1-yl)-furan-2-carbaldehyde (yield: 1.18 g, 60%). The produced 5-(4-methyl-piperazin-1-yl)-furan-2-carbaldehyde (1.18 g) was condensed with 3,4-dimethoxybenzyl cyanide (1.06 g) through Method A (production step 2), to thereby yield the target product (yield: 2.06 g, 96%).
Yellowish Brown Oil
MS (ESI, m/z): 356 (M+H)$^+$
$^1$H-NMR (CDCl$_3$) δ: 7.12 (1H, dd, J=2.2, 8.5), 7.05 (1H, d, J=2.2), 6.92 (1H, s), 6.86 (1H, d, J=8.5), 6.83 (1H, d, J=3.7), 5.16 (1H, d, J=3.7), 3.94 (3H, s), 3.90 (3H, s), 3.53 (2H, t, J=7.0), 3.07 (3H, s), 2.56 (2H, t, J=3.7), 2.31 (6H, s)

Production of (Z)-2-(3,4-dimethoxy-phenyl)-3-{5-[(2-dimethylamino-ethyl)-methyl-amino]-furan-2-yl}-acrylonitrile hydrochloride (Compound 49)

0.1N Hydrochloric acid (12.5 mL) was added to Compound 48 (404 mg) for dissolution, and purified water (20 mL) was added to the solution, followed by stirring at room temperature for 20 minutes. The reaction mixture was lyophilized, to thereby yield the target product (yield: 400 mg, 90%).
Yellowish Brown Powder
MS (ESI, m/z): 356 (M−HCl+H)$^+$
$^1$H-NMR (CDCl$_3$) δ: 7.11 (1H, dd, J=2.2, 8.5), 7.02 (1H, d, J=2.2), 6.91 (1H, s), 6.88 (1H, d, J=8.5), 6.70 (1H, d, J=3.7), 5.24 (1H, d, J=3.7), 4.03 (2H, t, J=7.3), 3.94 (3H, s), 3.91 (3H, s), 3.44 (2H, t, J=7.3), 3.11 (3H, s), 2.89 (6H, s)

Production of (Z)-2-(3,4-dimethoxy-phenyl)-3-{5-[4-(2-hydroxy-ethyl)-piperazin-1-yl]-furan-2-yl}-acrylonitrile hydrochloride (Compound 50)

0.1N Hydrochloric acid (11.8 mL) was added to Compound 28 (410 mg) for dissolution, and purified water (20 mL) was added to the solution, followed by stirring at room temperature for 20 minutes. The reaction mixture was lyophilized, to thereby yield the target product (yield: 404 mg, 90%).
Yellowish Brown Powder
MS (ESI, m/z): 384 (M−HCl+H)$^+$
$^1$H-NMR (CDCl$_3$) δ: 7.16 (1H, dd, J=2.2, 8.5), 7.05 (1H, d, J=2.2), 6.98 (1H, s), 6.89 (1H, d, J=8.5), 6.77 (1H, d, J=3.7), 5.41 (1H, d, J=3.7), 4.05-4.12 (2H, m), 3.94 (3H, s), 3.91 (3H, s), 3.90-3.94 (6H, m), 3.49 (2H, s), 3.18-3.22 (2H, m)

Production of mono-(1-{5-[(Z)-2-cyano-2-(3,4-dimethoxy-phenyl)-vinyl]-furan-2-yl}-piperidin-4-yl)succinate (Compound 51)

Compound 26 (800 mg) was dissolved in pyridine (4 mL), and succinic anhydride (1.13 g) was added to the solution, followed by stirring under reflux for 2 hours. After completion of reaction, methanol was added to the reaction mixture, followed by stirring for 30 minutes. The solvent was evaporated to dryness, and the residue was extracted with chloroform and purified water. The organic layer was dried over sodium sulfate anhydrate, and the solvent was evaporated to dryness. The residue was washed with hexane, to thereby yield the target product (yield: 954 mg, 93%).
Yellow Powder
MS (ESI, m/z): 453 (M−H)$^−$
$^1$H-NMR (DMSO) δ: 1.64-1.66 (2H, m), 1.87-1.89 (2H, m), 2.08-2.13 (2H, m), 2.34-2.39 (2H, m), 3.21-3.28 (2H, m), 3.59-3.62 (2H, m), 3.77 (3H, s), 3.82 (3H, s), 4.86-4.88 (1H, m), 5.60 (1H, d, J=3.7), 6.96 (1H, d, J=3.4), 7.00 (1H, d, J=8.5), 7.09 (1H, dd, J=2.0, 8.5), 7.16 (1H, d, J=2.0), 7.46 (1H, s)

Production of mono-(1-{5-[(Z)-2-cyano-2-(3,4-dimethoxy-phenyl)-vinyl]-furan-2-yl}-piperidin-4-yl)phosphate (Compound 52)

Compound 26 (383 mg) and bis(2,2,2-trichloroethyl) phosphorochloridate (1.64 g) were dissolved in pyridine (4 mL), and the solution was stirred at room temperature for 2 hours. After completion of reaction, methanol was added to the reaction mixture, followed by stirring for 30 minutes. The solvent was evaporated to dryness, and the residue was purified by silica gel column chromatography (ethyl acetate:hexane=7:13), to thereby yield 1-{5-[(Z)-2-cyano-2-(3,4-dimethoxy-phenyl)-vinyl]-furan-2-yl}-piperidin-4-yl bis-(2,2,2-trichloro-ethyl)phosphate (yield: 663 mg, 88%).
The produced 1-{5-[(Z)-2-cyano-2-(3,4-dimethoxy-phenyl)-vinyl]-furan-2-yl}-piperidin-4-yl bis-(2,2,2-trichloro-ethyl)phosphate (376 mg) was dissolved in a solvent mixture (5 mL) of pyridine and acetic acid (4:1). Zinc powder (353 mg) was added to the solution, followed by stirring at room temperature for 4 hours. Insoluble zinc powder was removed through filtration, and an IRC748 (NH$_4$$^+$) resin (11 g) was added to the filtrate, followed by stirring at room temperature for 30 minutes. Resinous material was removed through filtration and the solvent was evaporated to dryness. The residue was washed with ethanol, to thereby yield the target product (yield: 192 mg, 82%).
Yellowish Brown Powder
MS (ESI, m/z): 433 (M−H)$^−$
$^1$H-NMR (DMSO) δ: 1.68-1.72 (2H, m), 1.93-1.99 (2H, m), 3.24-3.30 (2H, m), 3.60-3.63 (2H, m), 3.77 (3H, s), 3.82 (3H, s), 4.27-4.30 (1H, m), 5.58 (1H, d, J=3.7), 6.96 (1H, d, J=3.4), 6.99 (1H, d, J=8.5), 7.08 (1H, dd, J=2.0, 8.5), 7.15 (1H, d, J=2.0), 7.44 (1H, s)

Production of mono-(1-{5-[(Z)-2-cyano-2-(3,4-dimethoxy-phenyl)-vinyl]-furan-2-yl}-piperidin-4-yl)phosphate sodium salt (Compound 53)

Purified water (10 mL) was added to Compound 52 (96 mg) to form suspension. An IRC748 (Na) resin (2 g) was added to the suspension, followed by stirring at room temperature. After dissolution of starting materials, resinous material was removed through filtration, and the solvent was evaporated to dryness, to thereby yield the target product (yield: 93 mg, 96%).
Yellowish Brown Powder
MS (ESI, m/z): 433 (M−2Na+H)$^−$
$^1$H-NMR (D$_2$O) δ: 1.50-1.53 (2H, m), 1.87-1.91 (2H, m), 2.96-2.99 (2H, m), 3.53-3.66 (2H, m), 3.64 (3H, s), 3.66 (3H, s), 4.04-4.06 (1H, m), 5.31 (1H, d, J=3.7), 6.64 (1H, d, J=3.9), 6.69-6.72 (2H, m), 6.78-6.81 (1H, m), 6.84 (1H, s)

Production of (Z)-3-(5-bromo-furan-2-yl)-2-(3,4-dimethoxy-phenyl)-acrylonitrile (Compound 54)

5-Bromo-2-furaldehyde (350 mg) was condensed with 3,4-dimethoxybenzyl cyanide (354 mg) through Method A (production step 2), to thereby yield the target product (yield: 558 mg, 84%).
Slightly Yellow Crystals
MS (APCI, m/z): 334 (M+H)$^+$
$^1$H-NMR (CDCl$_3$) δ: 7.23 (1H, s), 7.22 (1H, d, J=3.7), 7.22 (1H, dd, J=2.2, 8.5), 7.08 (1H, d, J=2.2), 6.91 (1H, d, J=8.5), 6.51 (1H, d, J=3.7), 3.95 (3H, s), 3.93 (3H, s)

Production of (E)-3-(3,4-dimethoxy-phenyl)-2-thiophen-2-yl-acrylonitrile (Compound 55)

2-Thiopheneacetonitrile (246 mg) was condensed with 3,4-dimethoxybenzaldehyde (332 mg) through Method B (production step 2), to thereby yield the target product (yield: 262 mg, 48%).
Yellow Crystals
MS (APCI, m/z): 272 (M+H)$^+$
$^1$H-NMR (CDCl$_3$) δ: 7.64 (1H, d, J=2.0), 7.31-7.36 (2H, m), 7.31 (1H, s), 7.28 (1H, dd, J=1.2, 5.1), 7.07 (1H, dd, J=3.7, 5.1), 6.92 (1H, d, J=8.5), 3.97 (3H, s), 3.95 (3H, s)

Production of (Z)-3-(3,4-dimethoxy-phenyl)-2-thiophen-3-yl-acrylonitrile (Compound 56)

3-Thiopheneacetonitrile (246 mg) was condensed with 3,4-dimethoxybenzaldehyde (332 mg) through Method B (production step 2), to thereby yield the target product (yield: 354 mg, 65%).

Slightly Yellow Crystals

MS (APCI, m/z): 272 (M+H)$^+$ $^1$H-NMR (CDCl$_3$) δ: 7.66 (1H, d, J=2.0), 7.55 (1H, dd, J=1.4, 2.9), 7.40 (1H, dd, J=2.9, 5.1), 7.38 (1H, s), 7.35 (1H, dd, J=1.4, 5.1), 7.33 (1H, dd, J=2.0, 8.0), 6.92 (1H, d, J=8.0), 3.97 (3H, s), 3.95 (3H, s)

Production of mono-(1-{5-[(Z)-2-cyano-2-(3,4-dimethoxy-phenyl)-vinyl]-thiophen-2-yl}-piperidin-4-yl)succinate sodium salt (Compound 57)

Purified water (10 mL) was added to Compound 18 (104 mg) to form suspension. An IRC748 (Na) resin (2 g) was added to the suspension, followed by stirring at room temperature. After dissolution of starting materials, resinous material was removed through filtration, and the solvent was evaporated to dryness, to thereby yield the target product (yield: 102 mg, 94%).

Yellow Powder

MS (ESI, m/z): 469 (M−Na)$^-$ $^1$H-NMR (D$_2$O) δ: 1.42-1.48 (2H, m), 1.64-1.70 (2H, m), 2.28-2.32 (2H, m), 2.39-2.43 (2H, m), 2.72-2.78 (2H, m), 3.05-3.10 (2H, m), 3.52 (3H, s), 3.62 (3H, s), 4.65-4.73 (1H, m), 5.67 (1H, d, J=3.4), 6.45 (1H, d, J=8.1), 6.59-6.61 (2H, m), 6.83 (1H, d, J=3.9), 7.03 (1H, s)

Production of mono-(1-{5-[(Z)-2-cyano-2-(3,4-dimethoxy-phenyl)-vinyl]-furan-2-yl}-piperidin-4-yl)succinate sodium salt (Compound 58)

Purified water (10 mL) was added to Compound 51 (101 mg) to form suspension. An IRC748 (Na) resin (2 g) was added to the suspension, followed by stirring at room temperature. After dissolution of starting materials, resinous material was removed through filtration, and the solvent was evaporated to dryness, to thereby yield the target product (yield: 96 mg, 91%).

Yellow Powder

MS (ESI, m/z): 453 (M−Na)$^-$ $^1$H-NMR (D$_2$O) δ: 1.44-1.52 (2H, m), 1.68-1.72 (2H, m), 2.31-2.34 (2H, m), 2.40-2.45 (2H, m), 2.91-2.98 (2H, m), 3.25-3.33 (2H, m), 3.56 (3H, s), 3.59 (3H, s), 4.68-4.76 (1H, m), 5.10-5.12 (1H, m), 6.44-6.49 (2H, m), 6.56-6.57 (3H, m)

Production of (Z)-2-(3,4-dimethoxy-phenyl)-3-{5-[4-(2-hydroxy-ethyl)-piperazin-1-yl]-thiophen-2-yl}-acrylonitrile methanesulfonate (Compound 59)

Methanesulfonic acid (81.6 μL) and ethanol (10 mL) were added to Compound 9 (500 mg), and the mixture was heated for dissolution (external temperature: 70° C.). The solution was returned to room temperature, followed by stirring overnight. The precipitated crystals were recovered through filtration, and the recovered crystals were washed sequentially with a small amount of ethanol and hexane. The crystals were thoroughly dried, to thereby yield the target product (yield: 530 mg, 85%).

Yellow Crystals

MS (ESI, m/z): 400 (M−CH$_3$SO$_3$H+H)$^+$ $^1$H-NMR (DMSO-d$_6$) δ: 7.98 (1H, s), 7.45 (1H, d, J=4.4), 7.19 (1H, d, J=2.2), 7.11 (1H, dd, J=2.2, 8.5), 7.02 (1H, J=8.5), 6.42 (1H, d, J=4.4), 3.83 (3H, s), 3.78 (3H, s), 3.75-3.83 (4H, m), 3.57-3.64 (2H, m), 3.25-3.40 (6H, m), 2.30 (3H, s),

Production of 1-[5-[(Z)-2-cyano-2-(3,4-dimethoxy-phenyl)-vinyl]-thiophen-2-yl]-piperidin-4-yl N-(2-diethylamino-ethyl)-succinamate hydrochloride (Compound 60)

Compound 18 (235 mg) was dissolved in methylene chloride (10 mL), and 2-chloro-4,6-dimethoxy-1,3,5-triazine (105 mg) and N-methylmorpholine (66 μL) were added to the solution, followed by stirring for 30 minutes with ice cooling. Subsequently, N,N-diethylethylenediamine (85 μL) and N-methylmorpholine (110 μL) were added to the mixture, followed by stirring at room temperature for 17 hours. The solvent was evaporated to dryness, and the residue was purified by silica gel column chromatography (CHCl$_3$-MeOH), to thereby yield the target product (yield: 287 mg, 95%).

Yellow Powder

MS (ESI, m/z): 569 (M−HCl+H)$^+$ $^1$H-NMR (CDCl$_3$) δ: 7.60 (1H, m), 7.37 (1H, s), 7.22 (1H, d, J=4.1), 7.13 (1H, dd, J=2.2, 8.3), 7.04 (1H, d, J=2.2), 6.87 (1H, d, J=4.1), 6.05 (1H, d, J=8.5 Hz), 4.96-5.00 (1H, m), 3.94 (3H, s), 3.90 (3H, s), 3.50-3.56 (2H, m), 3.39-3.43 (2H, m), 3.25-3.31 (2H, m), 3.05-3.17 (6H, m), 2.65-2.69 (2H, m), 2.56-2.59 (2H, m), 2.02-2.12 (2H, m), 1.97-2.01 (2H, m), 1.83-1.90 (2H, m), 1.39 (6H, t, J=7.3)

Production of 1-[5-[(Z)-2-cyano-2-(3,4-dimethoxy-phenyl)-vinyl]-thiophen-2-yl]-piperidin-4-yl N-(3-diethylamino-propyl)-succinamate hydrochloride (Compound 61)

Compound 18 (235 mg) was dissolved in methylene chloride (10 mL), and 2-chloro-4,6-dimethoxy-1,3,5-triazine (105 mg) and N-methylmorpholine (66 μL) were added to the solution, followed by stirring with ice cooling for 30 minutes. Subsequently, N,N-diethyl-1,3-diamino-propane (94 μL) and N-methylmorpholine (110 μL) were added to the mixture, followed by stirring at room temperature for 17 hours. The solvent was evaporated to dryness, and the residue was purified by silica gel column chromatography (CHCl$_3$-MeOH), to thereby yield the target product (yield: 279 mg, 90%).

Yellow Powder

MS (ESI, m/z): 583 (M−HCl+H)$^+$ $^1$H-NMR (CDCl$_3$) δ: 7.60 (1H, m), 7.37 (1H, s), 7.22 (1H, d, J=4.1), 7.13 (1H, dd, J=2.2, 8.3), 7.04 (1H, d, J=2.2), 6.87 (1H, d, J=4.1), 6.05 (1H, d, J=8.5), 4.96-5.00 (1H, m), 3.94 (3H, s), 3.90 (3H, s), 3.50-3.56 (2H, m), 3.39-3.43 (2H, m), 3.25-3.31 (2H, m), 3.05-3.17 (6H, m), 2.65-2.69 (2H, m), 2.56-2.59 (2H, m), 2.02-2.12 (2H, m), 1.97-2.01 (2H, m), 1.83-1.90 (2H, m), 1.39 (6H, t, J=7.3)

(1) Production of 1-[5-[(Z)-2-cyano-2-(3,4-dimethoxy-phenyl)-vinyl]-thiophen-2-yl]-piperidin-4-yl dimethylamino-acetate Compound 6 (3.70 g) was dissolved in pyridine (100 mL), and N,N-dimethylglycin (5.15 g) was added to the solution, followed by stirring at room temperature for 1 hour. Subsequently, p-toluenesulfonyl chloride (9.43 g) was added to the mixture, followed by stirring under reflux for 12 hours. After completion of reaction, the solvent was evaporated to dryness. Chloroform (800 mL) was added to the residue, and the mixture was washed with water three times. The pH of the aqueous layer was checked by use of a pH testpaper, and adjusted to 4 to 5 with 1N aqueous hydrochloric acid. The organic layer was dried over sodium sulfate anhydrate, and the solvent was evaporated to dryness. The residue was purified by silica gel column chromatography (CHCl₃-Hexane), to thereby yield the target product (yield: 3.48 g, 76%).

Yellow Powder

MS (ESI, m/z): 456 (M+H)⁺

$^1$H-NMR (CDCl₃) δ: 7.36 (1H, s), 7.22 (1H, d, J=4.1), 7.13 (1H, dd, J=2.2, 8.3), 7.04 (1H, d, J=2.2), 6.87 (1H, d, J=8.5), 6.05 (1H, d, J=4.1), 5.03-5.09 (1H, m), 3.94 (3H, s), 3.90 (3H, s), 3.54-3.60 (2H, m), 3.24-3.30 (2H, m), 3.19 (2H, s), 2.37 (6H, s), 2.02-2.07 (2H, m), 1.83-1.91 (2H, m)

(2) Production of 1-[5-[(Z)-2-cyano-2-(3,4-dimethoxy-phenyl)-vinyl]-thiophen-2-yl]-piperidin-4-yl dimethylamino-acetate p-toluenesulfonate (Compound 62)

Compound 6 (370 mg) was dissolved in toluene (80 mL), and N,N-dimethylglycin hydrochloride (140 mg) and p-toluenesulfonic acid monohydrate (380 mg) were added to the solution, followed by stirring under reflux for 5 hours. The solvent was evaporated to dryness, and the residue was purified by silica gel column chromatography (CHCl₃-MeOH), to thereby yield the target product (yield: 38 mg, 7.7%).

Yellow Powder

MS (ESI, m/z): 456 (M+H)⁺

$^1$H-NMR (DMSO) δ: 7.94 (1H, s), 7.49 (4H, d, J=7.8), 7.43 (1H, d, J=4.1), 7.17 (1H, d, J=2.2), 7.12 (4H, d, J=7.8), 7.09 (1H, dd, J=2.2, 8.5), 7.00 (1H, d, J=8.5), 6.32 (1H, d, J=4.1), 5.09-5.12 (1H, m), 4.26 (2H, s), 3.83 (3H, s), 3.78 (3H, s), 3.51-3.55 (2H, m), 3.31-3.37 (2H, m), 2.89 (6H, s), 2.29 (6H, s), 2.02-2.06 (2H, m), 1.78-1.82 (2H, m)

Production of 1-[5-[(Z)-2-cyano-2-(3,4-dimethoxy-phenyl)-vinyl]-thiophen-2-yl]-piperidin-4-yl[1,4']bipiperidinyl-1'-carboxylate hydrochloride (Compound 63)

Compound 6 (2.00 g) was dissolved in pyridine (50 mL), and 1-chlorocarbonyl-4-piperidinopiperidine (2.50 g) was added to the solution, followed by stirring under reflux for 2 hours. After completion of reaction, methanol was added to the reaction mixture, followed by stirring for 30 minutes. The solvent was evaporated under reduced pressure, and the residue was extracted with chloroform and purified water. The organic layer was dried over sodium sulfate anhydrate, and the solvent was evaporated to dryness. The residue was recrystallized from ethyl acetate, to thereby yield the target product (yield: 974 mg, 30%).

Yellow Powder

MS (ESI, m/z): 565 (M−HCl+H)⁺

$^1$H-NMR (CDCl₃) δ: 7.37 (1H, s), 7.22 (1H, d, J=4.4), 7.13 (1H, dd, J=2.0, 8.3), 7.04 (1H, d, J=2.0), 6.87 (1H, d, J=8.3), 6.05 (1H, d, J=4.4), 4.90-4.94 (1H, m), 3.94 (3H, s), 3.90 (3H, s), 3.48-3.54 (2H, m), 3.25-3.34 (2H, m), 2.74 (2H, m), 2.42-2.53 (7H, m), 2.01-2.06 (2H, m), 1.83-1.85 (4H, m), 1.60-1.61 (4H, m), 1.45 (4H, m)

Production of 1-[5-[(Z)-2-cyano-2-(3,4-dimethoxy-phenyl)-vinyl]-thiophen-2-yl]-piperidin-4-yl 4-[1,4']bipiperidinyl-1'-yl-4-oxo-butylate hydrochloride (Compound 64)

Compound 18 (1.00 g) was dissolved in methylene chloride (20 mL), and 2-chloro-4,6-dimethoxy-1,3,5-triazine (448 mg) and N-methylmorpholine (258 μL) were added to the solution, followed by stirring with ice cooling for 30 minutes. Subsequently, 4-piperidinopiperidine (429 mg) and N-methylmorpholine (430 μL) were added to the mixture, followed by stirring at room temperature for 17 hours. The solvent was evaporated to dryness, and the residue was recrystallized from ethyl acetate, to thereby yield the target product (yield: 1.37 g, 98%).

Yellow Powder

MS (ESI, m/z): 621 (M−HCl+H)⁺

$^1$H-NMR (CDCl₃) δ: 7.38 (1H, s), 7.22 (1H, d, J=4.4), 7.13 (1H, dd, J=2.4, 8.3), 7.04 (1H, d, J=2.4), 6.87 (1H, d, J=8.3), 6.05 (1H, d, J=4.4), 5.00-5.04 (1H, m), 3.94 (3H, s), 3.90 (3H, s), 3.50-3.56 (2H, m), 3.26-3.32 (2H, m), 3.00-3.06 (2H, m), 2.50-2.72 (11H, m), 1.95-2.04 (2H, m), 1.87-1.90 (4H, m), 1.65-1.70 (4H, m), 1.42-1.55 (4H, m)

Production of (Z)-2-(3,4-dimethoxy-phenyl)-3-quinolin-4-yl-acrylonitrile (Compound 65)

4-Quinolinecarboxaldehyde (500 mg) was condensed with 3,4-dimethoxybenzyl cyanide (564 mg) through Method A (production step 2), to thereby yield the target product (yield: 522 mg, 52%)

Pale Yellow Crystals

MS (ESI, m/z): 317 (M+H)⁺

$^1$H-NMR (CDCl₃) δ: 9.04 (1H, d, J=4.5), 8.20 (1H, d, J=8.5), 8.07 (1H, s), 7.99 (1H, d, J=8.5), 7.87 (1H, d, J=4.5), 7.77-7.81 (1H, m), 7.61-7.65 (1H, m), 7.39 (1H, dd, J=8.5, 2.3), 7.25 (1H, d, J=2.3), 6.98 (1H, d, J=8.5), 4.00 (3H, s), 3.97 (3H, s)

Production of (Z)-3-benzo[b]thiophen-3-yl-2-(3,4-dimethoxy-phenyl)-acrylonitrile (Compound 66)

Benzo[b]thiophene-3-carboxaldehyde (200 mg) was condensed with 3,4-dimethoxybenzyl cyanide (218 mg) through Method A (production step 2), to thereby yield the target product (yield: 365 mg, 92%).

Pale Yellow Crystals

MS (APCI, m/z): 322 (M+H)⁺

$^1$H-NMR (CDCl₃) δ: 8.56 (1H, s), 7.93 (1H, d, J=7.3), 7.89 (1H, d, J=7.3), 7.72 (1H, s), 7.43-7.51 (2H, m), 7.32 (1H, dd, J=2.3, 8.5), 7.20 (1H, d, J=2.3), 6.96 (1H, d, J=8.5), 3.99 (3H, s), 3.95 (3H, s)

Production of (Z)-2-(3,4-dimethoxy-phenyl)-3-(1-methyl-1H-benzimidazol-2-yl)-acrylonitrile (Compound 67)

1-Methyl-2-formylbenzimidazole (200 mg) was condensed with 3,4-dimethoxybenzyl cyanide (221 mg) through Method A (production step 2), to thereby yield the target product (yield: 369 mg, 93%).

Pale Yellow Crystals

MS (ESI, m/z): 320 (M+H)⁺

$^1$H-NMR (CDCl₃) δ: 7.88-7.92 (1H, m), 7.37 (1H, s), 7.32-7.39 (4H, m), 7.24 (1H, d, J=2.3), 6.94 (1H, d, J=8.5), 3.98 (3H, s), 3.95 (3H, s), 3.89 (3H, s)

Production of (Z)-2-(3,4-dimethoxy-phenyl)-3-(1-methyl-1H-indol-3-yl)-acrylonitrile (Compound 68)

1-Methylindole-3-carboxaldehyde (200 mg) was condensed with 3,4-dimethoxybenzyl cyanide (223 mg) through Method A (production step 2), to thereby yield the target product (yield: 292 mg, 73%).

Pale Yellow Crystals

MS (ESI, m/z): 319 (M+H)⁺

$^1$H-NMR (CDCl₃) δ: 8.29 (1H, s), 7.78 (1H, d, J=8.0), 7.74 (1H, s), 7.31-7.36 (1H, m), 7.37-7.42 (1H, m), 7.22-7.28 (3H, m), 7.16 (1H, d, J=2.3), 6.93 (1H, d, J=8.5), 3.98 (3H, s), 3.93 (3H, s), 3.91 (3H, s)

Production of (Z)-3-benzofuran-2-yl-(3,4-dimethoxy-phenyl)-acrylonitrile (Compound 69)

2-Benzofurancarboxaldehyde (166 mg) was condensed with 3,4-dimethoxybenzyl cyanide (201 mg) through Method A (production step 2), to thereby yield the target product (yield: 265 mg, 77%).
Yellow Crystals
MS (APCI, m/z): 306 (M+H)$^+$
$^1$H-NMR (CDCl$_3$) δ: 7.65 (1H, br d, J=7.8), 7.55 (1H, br d, J=8.3), 7.48 (1H, br s), 7.36-7.42 (2H, m), 7.31 (1H, dd, J=2.4, 8.5), 7.29 (1H, br d, J=7.8), 7.17 (1H, d, J=2.4), 6.94 (1H, d, J=8.5), 3.98 (3H, s), 3.94 (3H, s)

Production of (Z)-3-(2-chloro-quinolin-3-yl)-2-(3,4-dimethoxy-phenyl)-acrylonitrile (Compound 70)

2-Chloro-3-quinolinecarboxaldehyde (200 mg) was condensed with 3,4-dimethoxybenzyl cyanide (185 mg) through Method A (production step 2), to thereby yield the target product (yield: 311 mg, 85%).
Pale Yellow Crystals
MS (ESI, m/z): 351 (M+H)$^+$
$^1$H-NMR (CDCl$_3$) δ: 8.87 (1H, s), 8.05 (1H, br d, J=8.0), 7.96 (1H, br d, J=8.0), 7.83 (1H, s), 7.84-7.89 (1H, m), 7.61-7.66 (1H, m), 7.37 (1H, d, J=2.2, 8.5), 7.22 (1H, d, J=2.2), 6.98 (1H, d, J=8.5), 3.99 (3H, s), 3.96 (3H, s)

Production of (E)-2-benzothiazol-1-yl-3-(3,4-dimethoxy-phenyl)-acrylonitrile (Compound 71)

3,4-Dimethoxybenzaldehyde (210 mg) was condensed with 1H-benzotriazole-1-acetonitrile (200 mg) through Method B (production step 2), to thereby yield the target product (yield: 133 mg, 34%).
White Crystals (Colorless)
MS (ESI, m/z): 307 (M+H)$^+$.
$^1$H-NMR (CDCl$_3$) δ: 8.15 (1H, br d, J=8.5), 7.90 (1H, br d, J=8.5), 7.83 (1H, s), 7.69 (1H, d, J=2.2), 7.62-7.66 (1H, m), 7.47-7.51 (1H, m), 7.44 (1H, dd, J=2.2, 8.5), 6.99 (1H, d, J=8.5), 4.00 (3H, s), 3.99 (3H, s)

Production of (Z)-2-benzofuran-3-yl-3-(3,4-dimethoxy-phenyl)-acrylonitrile (Compound 72)

3,4-Dimethoxybenzaldehyde (106 mg) was condensed with benzofuran-3-acetonitrile (100 mg) through Method B (production step 2), to thereby yield the target product (yield: 110 mg, 57%).
White Needles (Colorless)
MS (APCI, m/z): 306 (M+H)$^+$
$^1$H-NMR (CDCl$_3$) δ: 7.97 (1H, s), 7.90-7.94 (1H, m), 7.69 (1H, d, J=2.0), 7.57 (1H, s), 7.56-7.58 (1H, m), 7.35-7.43 (3H, m), 6.95 (1H, d, J=8.5), 3.99 (3H, s), 3.96 (3H, s)

Production of (Z)-3-(2-chloro-6-methoxy-quinolin-3-yl)-2-(3,4-dimethoxy-phenyl)-acrylonitrile (Compound 73)

2-Chloro-6-methoxy-3-quinolinecarboxaldehyde (500 mg) was condensed with 3,4-dimethoxybenzyl cyanide (400 mg) through Method A (production step 2), to thereby yield the target product (yield: 784 mg, 91%).
Slightly Yellow Powder
MS (ESI, m/z): 381 (M+H)$^+$
$^1$H-NMR (CDCl$_3$) δ: 8.78 (1H, s), 7.93 (1H, d, J=9.3), 7.82 (1H, s), 7.44 (1H, dd, J=2.9, 9.3), 7.36 (1H, dd, J=2.2, 8.5), 7.22 (1H, d, J=2.2), 7.19 (1H, d, J=2.9), 6.97 (1H, d, J=8.5), 4.00 (3H, s), 3.97 (3H, s), 3.96 (3H, s)

Production of (E)-2-benzothiazol-2-yl-3-(3,4-dimethoxy-phenyl)-acrylonitrile (Compound 74)

3,4-Dimethoxybenzaldehyde (191 mg) was condensed with 2-benzothiazoleacetonitrile (200 mg) through Method B (production step 2), to thereby yield the target product (yield: 330 mg, 89%).
Yellow Powder
MS (ESI, m/z): 323 (M+H)$^+$
$^1$H-NMR (CDCl$_3$): 8.18 (1H, s), 8.05-8.08 (1H, m), 7.89-7.92 (1H, m), 7.83 (1H, d, J=2.2), 7.50-7.55 (2H, m), 7.40-7.44 (1H, m), 6.97 (1H, d, J=8.5), 3.99 (3H, s), 3.98 (3H, s)

Production of (Z)-3-(2,3-dihydro-benzofuran-5-yl)-2-(3,4-dimethoxy-phenyl)-acrylonitrile (Compound 75)

2,3-Dihydrobenzofuran-5-carboxaldehyde (150 mg) was condensed with 3,4-dimethoxybenzyl cyanide (180 mg) through Method A (production step 2), to thereby yield the target product (yield: 154 mg, 50%).
Yellow Powder
MS (APSI, m/z): 308 (M+H)$^+$
$^1$H-NMR (CDCl$_3$) δ: 7.93 (1H, br s), 7.55 (1H, d, J=1.6, 8.4), 7.34 (1H, s), 7.22 (1H, dd, J=2.2, 8.4), 7.12 (1H, d, J=2.2), 6.91 (1H, d, J=8.5), 6.85 (1H, d, J=8.5), 4.66 (2H, t, J=8.7), 3.96 (3H, s), 3.92 (3H, s), 3.29 (2H, t, J=8.7)

Production of (Z)-2-(3,4-dimethoxy-phenyl)-3-[5-(4-fluoro-phenyl)-isoxazol-3-yl]-acrylonitrile (Compound 76)

5-(4-Fluorophenyl)-isoxazole-3-carboxaldehyde (200 mg) was condensed with 3,4-dimethoxybenzyl cyanide (185 mg) through Method A (production step 2), to thereby yield the target product (yield: 150 mg, 41%).
Yellow Powder
MS (ESI, m/z): 351 (M+H)$^+$
$^1$H-NMR (CDCl$_3$) δ: 3.95 (3H, s), 3.98 (3H, s), 6.95 (1H, d, J=8.5), 7.18-7.24 (3H, m), 7.35 (1H, dd, J=2.3, 8.5), 7.44 (1H, s), 7.59 (1H, s), 7.87 (2H, dd, J=2.5, 9.5)

Production of (Z)-2-(3,4-dimethoxy-phenyl)-3-[5-(4-methoxy-phenyl)-isoxazol-3-yl]-acrylonitrile (Compound 77)

5-(4-Methoxyphenyl)-isoxazole-3-carboxaldehyde (200 mg) was condensed with 3,4-dimethoxybenzyl cyanide (174 mg) through Method A (production step 2), to thereby yield the target product (yield: 127 mg, 36%).
Yellow Powder
MS (ESI, m/z): 363 (M+H)$^+$
$^1$H-NMR (CDCl$_3$) δ: 7.81 (1H, d, J=9.4), 7.59 (1H, s), 7.37 (1H, s), 7.35 (1H, dd, J=2.2, 8.5), 7.19 (1H, d, J=2.2), 7.01 (2H, d, J=9.4), 6.95 (1H, d, J=8.5), 3.97 (3H, s), 3.95 (3H, s), 3.89 (3H, s)

Production of (Z)-2-(3,4-dimethoxy-phenyl)-3-quinolin-2-yl-acrylonitrile (Compound 78)

2-Quinolinecarboxaldehyde (200 mg) was condensed with 3,4-dimethoxybenzyl cyanide (225 mg) through Method A (production step 2), to thereby yield the target product (yield: 252 mg, 63%).

Yellow Powder
MS (ESI, m/z): 316 (M+H)$^+$
$^1$H-NMR (CDCl$_3$) δ: 8.27 (1H, d, J=8.5), 8.18 (1H, d, J=8.5), 8.15 (1H, d, J=8.5), 7.86 (1H, br d, J=8.5), 7.76 (1H, s), 7.74-7.80 (1H, m), 7.58-7.62 (1H, m), 7.43 (1H, dd, J=2.2, 8.3), 7.29 (1H, d, J=2.2), 6.96 (1H, d, J=8.3), 3.99 (3H, s), 3.96 (3H, s)

Production of (Z)-3-(2-chloro-6-methoxy-quinolin-3-yl)-2-pyridin-2-yl-acrylonitrile (Compound 79)

2-Chloro-6-methoxy-3-quinolinecarboxaldehyde (222 mg) was condensed with 2-pyridineacetonitrile (118 mg) through Method B (production step 3), to thereby yield the target product (yield: 311 mg, 97%).
Slightly Yellow Crystals
MS (ESI, m/z): 322 (M+H)$^+$
$^1$H-NMR (CDCl$_3$) δ: 8.883 (1H, s), 8.875 (1H, s), 8.71-8.74 (1H, m), 7.94 (1H, d, J=9.1), 7.83-7.87 (2H, m), 7.46 (1H, d, J=2.8, 9.1), 7.35-7.39 (1H, m), 7.21 (1H, d, J=2.8), 3.97 (3H, s)

Production of (Z)-3-(2-chloro-6-methoxy-quinolin-3-yl)-2-pyridin-3-yl-acrylonitrile (Compound 80)

2-Chloro-6-methoxy-3-quinolinecarboxaldehyde (222 mg) was condensed with 3-pyridineacetonitrile (118 mg) through Method B (production step 3), to thereby yield the target product (yield: 251 mg, 78%).
White Crystals
MS (ESI, m/z): 322 (M+H)$^+$
$^1$H-NMR (CDCl$_3$) δ: 9.03 (1H, d, J=2.4), 8.84 (1H, s), 8.72 (1H, dd, J=1.5, 4.9), 8.03-8.07 (1H, m), 8.02 (1H, s), 7.95 (1H, d, J=9.0), 7.44-7.50 (2H, m), 7.21 (1H, d, J=2.7), 3.97 (3H, s)

Production of (E)-3-(2-chloro-6-methoxy-quinolin-3-yl)-2-thiophen-2-yl-acrylonitrile (Compound 81)

2-Chloro-6-methoxy-3-quinolinecarboxaldehyde (222 mg) was condensed with 2-thiopheneacetonitrile (123 mg) through Method B (production step 3), to thereby yield the target product (yield: 301 mg, 92%).
Pale Yellow Crystals
MS (ESI, m/z): 327 (M+H)$^+$
$^1$H-NMR (CDCl$_3$) δ: 8.77 (1H, s), 7.92 (1H, d, J=9.3), 7.79 (1H, s), 7.50 (1H, dd, J=1.2, 3.7), 7.44 (1H, dd, J=2.7, 9.3), 7.42 (1H, dd, J=1.5, 6.6), 7.18 (1H, d, J=2.7), 7.14 (1H, dd, J=3.7, 5.1), 3.96 (3H, s)

Production of (Z)-3-(2-chloro-6-methoxy-quinolin-3-yl)-2-thiophen-3-yl-acrylonitrile (Compound 82)

2-Chloro-6-methoxy-3-quinolinecarboxaldehyde (222 mg) was condensed with 3-thiopheneacetonitrile (123 mg) through Method B (production step 3), to thereby yield the target product (yield: 273 mg, 83%).
Slightly Yellow Crystals
MS (ESI, m/z): 327 (M+H)$^+$
$^1$H-NMR (CDCl$_3$) δ: 8.78 (1H, s), 7.92 (1H, d, J=9.1), 7.85 (1H, s), 7.72-7.75 (1H, m), 7.46-7.48 (2H, m), 7.44 (1H, dd, J=2.8, 9.1), 7.18 (1H, d, J=2.8), 3.96 (3H, s)

Production of (E)-2-benzotriazol-1-yl-3-(2-chloro-6-methoxy-quinolin-3-yl)-acrylonitrile (Compound 83)

2-Chloro-6-methoxy-3-quinolinecarboxaldehyde (111 mg) was condensed with 1H-benzotriazole-1-acetonitrile (79 mg) through Method B (production step 3), to thereby yield the target product (yield: 129 mg, 71%).
White Powder
MS (ESI, m/z): 362 (M+H)$^+$
$^1$H-NMR (CDCl$_3$) δ: 8.85 (1H, s), 8.21 (1H, d, J=8.3), 8.36 (1H, s), 8.00 (1H, t, J=9.3), 7.98 (1H, t, J=9.3), 7.69-7.73 (1H, m), 7.53-7.57 (1H, m), 7.51 (1H, dd, J=2.8, 9.3), 7.24 (1H, d, J=2.8), 3.99 (3H, s)

Production of (E)-2-benzothiazol-2-yl-3-(2-chloro-6-methoxy-quinolin-3-yl)-acrylonitrile (Compound 84)

2-Chloro-6-methoxy-3-quinolinecarboxaldehyde (111 mg) was condensed with 2-benzothiazoleacetonitrile (87 mg) through Method B (production step 3), to thereby yield the target product (yield: 148 mg, 78%).
Yellow Crystals
MS (ESI, m/z): 378 (M+H)$^+$
$^1$H-NMR (CDCl$_3$) δ: 8.99 (1H, s), 8.65 (1H, s), 8.17 (1H, d, J=8.1), 7.90-7.95 (2H, m), 7.55-7.61 (1H, m), 7.46-7.52 (2H, m), 7.22 (1H, d, J=2.7), 3.98 (3H, s)

Production of (Z)-2-pyridin-2-yl-3-quinolin-4-yl-acrylonitrile (Compound 85)

4-Quinolinecarboxaldehyde (157 mg) was condensed with 2-pyridineacetonitrile (118 mg) through Method B (production step 3), to thereby yield the target product (yield: 138 mg, 54%).
Slightly Pink Crystals
MS (ESI, m/z): 258 (M+H)$^+$
$^1$H-NMR (CDCl$_3$) δ: 9.22 (1H, s), 9.06 (1H, d, J=4.4), 8.72-8.74 (1H, m), 8.21 (1H, d, J=8.3), 8.10 (1H, d, J=8.3), 7.96 (1H, d, J=4.4), 7.80-7.83 (2H, m), 7.75-7.82 (1H, m), 7.62-7.67 (1H, m), 7.38-7.41 (1H, m)

Production of (Z)-2-pyridin-3-yl-3-quinolin-4-yl-acrylonitrile (Compound 86)

4-Quinolinecarboxaldehyde (157 mg) was condensed with 3-pyridineacetonitrile (118 mg) through Method B (production step 3), to thereby yield the target product (yield: 76 mg, 29%).
White Powder
MS (ESI, m/z): 258 (M+H)$^+$
$^1$H-NMR (CDCl$_3$) δ: 9.08 (1H, d, J=4.6), 9.07 (1H, d, J=2.4), 8.74 (1H, d, J=1.6, 4.8), 8.27 (1H, s), 8.23 (1H, d, J=7.8), 8.09 (1H, ddd, J=1.7, 2.4, 8.1), 7.98 (1H, d, J=8.5), 7.91 (1H, d, J=4.8), 7.80-7.84 (1H, m), 7.64-7.68 (1H, m), 7.49 (1H, dd, J=4.8, 8.1)

Production of (E)-3-quinolin-4-yl-2-thiophen-2-yl-acrylonitrile (Compound 87)

4-Quinolinecarboxaldehyde (157 mg) was condensed with 2-thiopheneacetonitrile (123 mg) through Method B (production step 3), to thereby yield the target product (yield: 175 mg, 67%).
Slightly Yellow Crystals
MS (ESI, m/z): 263 (M+H)$^+$
$^1$H-NMR (CDCl$_3$) δ: 9.03 (1H, d, J=4.4), 8.20 (1H, d, J=8.5), 8.03 (1H, s), 7.99 (1H, d, J=8.5), 7.89 (1H, dd, J=0.9, 4.4), 7.78-7.82 (1H, m), 7.63-7.67 (1H, m), 7.53 (1H, dd, J=1.2, 3.7), 7.45 (1H, dd, J=1.2, 5.1), 7.16 (1H, dd, J=3.7, 5.1)

Production of (Z)-3-quinolin-4-yl-2-thiophen-3-yl-acrylonitrile (Compound 88)

4-Quinolinecarboxaldehyde (157 mg) was condensed with 3-thiopheneacetonitrile (123 mg) through Method B (production step 3), to thereby yield the target product (yield: 81 mg, 31%).
Yellow Powder
MS (ESI, m/z): 263 (M+H)$^+$
$^1$H-NMR (CDCl$_3$) δ: 9.03 (1H, d, J=4.4), 8.20 (1H, d, J=8.4), 8.09 (1H, s), 7.98 (1H, d, J=8.4), 7.87 (1H, d, J=4.4), 7.76-7.82 (2H, m), 7.61-7.65 (1H, m), 7.50 (1H, s), 7.49 (1H, s)

Production of (E)-3-benzo[b]thiophen-3-yl-2-thiophen-2-yl-acrylonitrile (Compound 89)

Benzo[b]thiophene-3-carboxaldehyde (81 mg) was condensed with 2-thiopheneacetonitrile (62 mg) through Method B (production step 3), to thereby yield the target product (yield: 40 mg, 30%).
Yellow Powder
MS (ESI, m/z): 268 (M+H)$^+$
$^1$H-NMR (CDCl$_3$) δ: 8.55 (1H, s), 7.91-7.93 (1H, m), 7.89 (1H, dd, J=1.2, 7.3), 7.67 (1H, s), 7.49 (1H, dd, J=1.2, 7.9), 7.46 (1H, dd, J=1.2, 7.9), 7.42 (1H, dd, J=1.2, 3.7), 7.34 (1H, dd, J=1.2, 5.1), 7.11 (1H, dd, J=3.7, 5.1)

Production of (E)-3-benzo[b]thiophen-3-yl-2-benzothiazol-2-yl-acrylonitrile (Compound 90)

Benzo[b]thiophene-3-carboxaldehyde (81 mg) was condensed with 2-benzothiazoleacetonitrile (87 mg) through Method B (production step 3), to thereby yield the target product (yield: 111 mg, 69%).
Yellow Powder
MS (ESI, m/z): 319 (M+H)$^+$
$^1$H-NMR (CDCl$_3$) δ: 8.89 (1H, s), 8.60 (1H, s), 8.11 (1H, br d, J=8.2), 8.06 (1H, br d, J=7.8), 7.91-7.96 (2H, m), 7.53-7.58 (2H, m), 7.43-7.52 (2H, m)

Production of (Z)-3-benzofuran-2-yl-2-benzofuran-3-yl-acrylonitrile (Compound 91)

2-Benzofurancarboxaldehyde (73 mg) was condensed with benzofuran-3-acetonitrile (79 mg) through Method B (production step 3), to thereby yield the target product (yield: 110 mg, 77%).
Yellow Powder
MS (ESI, m/z): 319 (M+H)$^+$
$^1$H-NMR (CDCl$_3$) δ: 8.06 (1H, s), 7.92-7.96 (1H, m), 7.66 (1H, br d, J=7.8), 7.58 (1H, s), 7.56-7.60 (2H, m), 7.47 (1H, s), 7.38-7.45 (3H, m), 7.28-7.32 (1H, m)

Production of (E)-2-benzothiazol-2-yl-3-(1-methyl-1H-indol-3-yl)-acrylonitrile (Compound 92)

1-Methylindole-3-carboxaldehyde (79 mg) was condensed with 2-benzothiazoleacetonitrile (87 mg) through Method B (production step 3), to thereby yield the target product (yield: 157 mg, 99%).
Yellow Powder
MS (ESI, m/z): 316 (M+H)$^+$
$^1$H-NMR (CDCl$_3$) δ: 8.56 (1H, s), 8.50 (1H, s), 8.03-8.07 (1H, m), 7.90-7.94 (1H, m), 7.86-7.90 (1H, m), 7.48-7.53 (1H, m), 7.33-7.45 (4H, m), 3.95 (3H, s)

Production of (Z)-3-(10-chloro-anthracen-9-yl)-2-(3,4-dimethoxy-phenyl)-acrylonitrile (Compound 93)

10-Chloro-9-anthraldehyde (500 mg) was condensed with 3,4-dimethoxybenzyl cyanide (368 mg) through Method A (production step 2), to thereby yield the target product (yield: 466 mg, 56%).
Yellow Powder
MS (APSI, m/z): 400 (M+H)$^+$
$^1$H-NMR (CDCl$_3$) δ: 8.61 (2H, d, J=8.5), 8.27 (1H, s), 8.09 (2H, d, J=8.5), 7.62-7.68 (2H, m), 7.55-7.61 (2H, m), 7.48 (1H, dd, J=2.2, 8.5), 7.35 (1H, d, J=2.2), 7.02 (1H, d, J=8.5), 4.01 (3H, s), 3.99 (3H, s)

Production of (Z)-2-(3,4-dimethoxy-phenyl)-3-naphthalen-2-yl-acrylonitrile (Compound 94)

2-Naphthaldehyde (500 mg) was condensed with 3,4-dimethoxybenzyl cyanide (567 mg) through Method A (production step 2), to thereby yield the target product (yield: 872 mg, 86%).
Yellow Powder
MS (APSI, m/z): 316 (M+H)$^+$
$^1$H-NMR (CDCl$_3$) δ: 8.27 (1H, s), 8.07 (1H, dd, J=1.7, 8.8), 7.84-7.93 (3H, m), 7.59 (1H, s), 7.51-7.58 (2H, m), 7.32 (1H, dd, J=2.2, 8.5), 7.20 (1H, d, J=2.2), 6.94 (1H, d, J=8.5), 3.99 (3H, s), 3.94 (3H, s)

Production of (Z)-2-(3,4-dimethoxy-phenyl)-3-phenanthren-9-yl-acrylonitrile (Compound 95)

Phenanthrene-9-aldehyde (250 mg) was condensed with 3,4-dimethoxybenzyl cyanide (214 mg) through Method A (production step 2), to thereby yield the target product (yield: 278 mg, 63%).
Yellow Powder
MS (APSI, m/z): 366 (M+H)$^+$
$^1$H-NMR (CDCl$_3$) δ: 8.77 (1H, d, J=7.8), 8.70 (1H, d, J=7.8), 8.26 (1H, s), 8.15 (1H, d, J=1.2), 7.99-8.02 (2H, m), 7.70-7.76 (2H, m), 7.63-7.68 (2H, m), 7.40 (1H, dd, J=2.4, 8.3), 7.28 (1H, d, J=2.4), 6.99 (1H, d, J=8.3), 4.00 (3H, s), 3.97 (3H, s)

Production of 1-[5-[(Z)-2-cyano-2-(3,4-dimethoxy-phenyl)-vinyl]-thiophen-2-yl]-piperidin-4-yl diethylamino-acetate p-toluenesulfonate (Compound 96)

Compound 6 (480 mg) was dissolved in toluene (100 mL), and N,N-diethylglycin sodium salt (296 mg) and p-toluenesulfonic acid monohydrate (490 mg) were added to the solution, followed by stirring under reflux for 5 hours. The solvent was evaporated to dryness, and the residue was purified by silica gel column chromatography (CHCl$_3$-MeOH), to thereby yield the target product (yield: 237 mg, 37.7%).
Yellow Powder
MS (ESI, m/z): 484 (M+H)$^+$
$^1$H-NMR (DMSO) δ: 7.94 (1H, s), 7.49 (4H, d, J=7.8), 7.43 (1H, d, J=4.1), 7.17 (1H, d, J=2.2), 7.12 (4H, d, J=7.8), 7.09 (1H, dd, J=2.2, 8.5), 7.00 (1H, d, J=8.5), 6.32 (1H, d, J=4.1), 5.09-5.12 (1H, m), 4.26 (2H, s), 3.83 (3H, s), 3.78 (3H, s), 3.51-3.55 (2H, m), 3.31-3.37 (2H, m), 3.22 (4H, q, J=7.1), 2.29 (6H, s), 2.02-2.06 (2H, m), 1.78-1.82 (2H, m), 1.21 (6H, t, J=7.1)

Production of 1-[5-[(Z)-2-cyano-2-(3,4-dimethoxy-phenyl)-vinyl]-thiophen-2-yl]-piperidin-4-yl diethyl-carbamate (Compound 97)

Compound 6 (150 mg) was dissolved in pyridine (1 mL), and diethylcarbamoyl chloride (55 mg) was added to the solution, followed by stirring under reflux for 2 hours. After completion of reaction, methanol was added to the reaction mixture, followed by stirring for 30 minutes. The solvent was evaporated to dryness, and the residue was extracted with chloroform and purified water. The organic layer was dried over sodium sulfate anhydrate, and the solvent was evaporated to dryness. The residue was recrystallized from ethyl acetate, to thereby yield the target product (yield: 40.6 mg, 21.3%).

Yellow Powder

MS (ESI, m/z): 470 (M+H)$^+$ $^1$H-NMR (CDCl$_3$) δ: 7.37 (1H, s), 7.23 (1H, d, J=4.4), 7.13 (1H, dd, J=2.2, 8.5), 7.04 (1H, d, J=2.2), 6.87 (1H, d, J=8.5), 6.05 (1H, d, J=4.4), 4.93-4.97 (1H, m), 3.74 (3H, s), 3.90 (3H, s), 3.48-3.54 (2H, m), 3.30-3.36 (6H, m), 2.01-2.08 (2H, m), 1.83-1.91 (2H, m), 1.14 (6H, t, J=7.1)

Production of 1-[5-[(Z)-2-cyano-2-(3,4-dimethoxy-phenyl)-vinyl]-thiophen-2-yl]-piperidin-4-yl N-(2-diethylamino-ethyl)-N-methyl-succinamate hydrochloride (Compound 98)

Compound 18 (500 mg) was dissolved in methylene chloride (10 mL), and 2-chloro-4,6-dimethoxy-1,3,5-triazine (224 mg) and N-methylmorpholine (129 μL) were added to the solution, followed by stirring with ice cooling for 30 minutes. Subsequently, N,N-diethyl-N'-methylethylenediamine (166 μL) and N-methylmorpholine (215 μL) were added to the mixture, followed by stirring at room temperature for 17 hours. The solvent was evaporated to dryness, and the residue was purified by silica gel column chromatography (CHCl3-MeOH), to thereby yield the target product (yield: 503 mg, 76%).

Yellow Powder

MS (ESI, m/z): 583 (M−HCl+H)$^+$ $^1$H-NMR (CDCl$_3$)d: 7.60 (1H, m), 7.37 (1H, s), 7.22 (1H, d, J=4.1), 7.13 (1H, dd, J=2.2, 8.3), 7.04 (1H, d, J=2.2), 6.87 (1H, d, J=4.1), 6.05 (1H, d, J=8.5 Hz), 4.96-5.00 (1H, m), 3.94 (3H, s), 3.90 (3H, s), 3.50-3.56 (2H, m), 3.39-3.43 (2H, m), 3.25-3.31 (2H, m), 3.05-3.17 (6H, m), 3.13 (3H, s), 2.65-2.69 (2H, m), 2.56-2.59 (2H, m), 2.02-2.12 (2H, m), 1.97-2.01 (2H, m), 1.83-1.90 (2H, m), 1.39 (6H, t, J=7.3)

Production of 1-[5-[(Z)-2-cyano-2-(3,4-dimethoxy-phenyl)-vinyl]-thiophen-2-yl]-piperidin-4-yl N-(4-diethylamino-phenyl)-succinamate (Compound 99)

Compound 18 (500 mg) was dissolved in methylene chloride (10 mL), and 2-chloro-4,6-dimethoxy-1,3,5-triazine (224 mg) and N-methylmorpholine (129 μL) were added to the solution, followed by stirring with ice cooling for 30 minutes. Subsequently, N,N-diethyl-1,4-phenylenediamine (209 μL) and N methylmorpholine (215 μL) were added to the mixture, followed by stirring at room temperature for 17 hours. The solvent was evaporated to dryness, and the residue was purified by silica gel column chromatography (CHCl$_3$-MeOH), to thereby yield the target product (yield: 322 mg, 49%).

Yellow Powder

MS (ESI, m/z): 617 (M+H)$^+$ $^1$H-NMR (CDCl$_3$) δ: 7.91 (1H, s), 7.40 (1H, d, J=4.4), 7.30 (2H, d, J=8.5), 7.17 (1H, d, J=2.2), 7.09 (1H, dd, J=2.2, 8.3), 7.00 (1H, d, J=8.8), 6.57 (2H, d, J=8.8), 6.27 (1H, d, J=4.1), 4.91-4.95 (1H, m), 3.83 (3H, s), 3.78 (3H, s), 3.44-3.49 (2H, m), 3.25-3.30 (6H, m), 2.57-2.60 (4H, m), 1.91-1.97 (2H, m), 1.71-1.74 (2H, m), 1.03 (6H, t, J=6.8)

Production of (Z)-2-(3,4-dimethoxy-phenyl)-3-{5-[4-(2-hydroxy-ethyl)-piperazin-1-yl]-thiophen-2-yl}-acrylonitrile ½ sulfate (Compound 100)

0.1-mol/L Sulfuric acid (6.35 mL) and purified water (18.65 mL) were added to Compound 9 (500 mg), and the mixture was heated for dissolution (external temperature: 90° C.). The solution was returned to room temperature, and allowed to stand overnight. The precipitated crystals were recovered through filtration, and the recovered crystals were washed sequentially with a small amount of purified water and hexane. The crystals were thoroughly dried, to thereby yield the target product (yield: 560 mg, ca. 100%).

Yellowish Orange Crystals

MS (ESI, m/z): 400 (M−0.5H$_2$SO$_4$+H)$^+$ $^1$H-NMR (DMSO-d$_6$) δ: 7.95 (1H, s), 7.43 (1H, d, J=4.4), 7.18 (1H, d, J=2.2) 7.10 (1H, dd, J=2.2, 8.5), 7.01 (1H, d, J=8.5), 6.35 (1H, d, J=4.4), 3.83 (3H, s), 3.78 (3H, s), 3.62-3.68 (2H, m), 3.38-3.50 (4H, m), 2.85-3.05 (6H, m)

Production of (Z)-2-(3,4-dimethoxy-phenyl)-3-{5-[4-(2-hydroxy-ethyl)-piperazin-1-yl]-thiophen-2-yl}-acrylonitrile sulfate (Compound 101)

0.1-mol/L Sulfuric acid (12.70 mL) and purified water (12.30 mL) were added to Compound 9 (500 mg), and the mixture was heated for dissolution (external temperature: 90° C.). The solution was returned to room temperature, and allowed to stand overnight. The precipitated crystals were recovered through filtration, and the recovered crystals were washed sequentially with a small amount of purified water and hexane. The crystals were thoroughly dried, to thereby yield the target product (yield: 564 mg, 91%).

Yellowish Orange Crystals

MS (ESI, m/z): 400 (M−H$_2$SO$_4$+H)$^+$ $^1$H-NMR (DMSO-d$_6$) δ: 7.95 (1H, s), 7.43 (1H, d, J=4.4), 7.18 (1H, d, J=2.2), 7.10 (1H, dd, J=2.2, 8.5), 7.01 (1H, d, J=8.5), 6.35 (1H, d, J=4.4), 3.83 (3H, s), 3.78 (3H, s), 3.62-3.68 (2H, m), 3.38-3.50 (4H, m), 2.83-3.07 (6H, m)

Production of (Z)-2-(3,4-dimethoxy-phenyl)-3-{5-[4-(2-hydroxy-ethyl)-piperazin-1-yl]-thiophen-2-yl}-acrylonitrile nitrate (Compound 102)

0.1-mol/L Nitric acid (12.70 mL) and purified water (12.30 mL) were added to Compound 9 (501 mg), and the mixture was heated for dissolution (external temperature: 90° C.). The solution was returned to room temperature, and allowed to stand overnight. The precipitated crystals were recovered through filtration, and the recovered crystals were washed sequentially with a small amount of purified water and hexane. The crystals were thoroughly dried, to thereby yield the target product (yield: 530 mg, 91%).

Yellow Crystals

MS (ESI, m/z): 400 (M−HNO$_3$+H)$^+$ $^1$H-NMR (DMSO-d$_6$) δ: 9.67 (1H, br s), 7.98 (1H, s), 7.45 (1H, d, J=4.4), 7.20 (1H, d, J=2.2), 7.12 (1H, dd, J=2.2, 8.5), 7.02 (1H, d, J=8.5), 6.42 (1H, d, J=4.4), 5.42 (1H, br s), 3.84 (3H, s), 3.79 (3H, s), 3.75-3.83 (4H, m), 3.57-3.64 (2H, m), 3.25-3.40 (6H, m)

Production of 1-[5-[(Z)-2-cyano-2-(3,4-dimethoxy-phenyl)-vinyl]-thiophen-2-yl]-piperidin-4-yl diethylamino-acetate (Compound 103)

Compound 6 (3.70 g) was dissolved in pyridine (100 mL), and N,N-diethylglycin sodium salt (7.66 g) was added to the solution, followed by stirring at room temperature for 1 hour. Subsequently, p-toluenesulfonyl chloride (9.43 g) was added to the mixture, followed by stirring under reflux for 12 hours. After completion of reaction, the solvent was evaporated under reduced pressure. Chloroform (1,000 mL) was added to the residue, and the mixture was washed with water three times. The pH of the aqueous layer was checked by use of a pH testpaper, and adjusted to 4 to 5 with 1N aqueous hydrochloric acid. The organic layer was dried over sodium sulfate anhydrate, and the solvent was evaporated to dryness. The residue was purified by silica gel column chromatography ($CHCl_3$-Hexane), to thereby yield the target product (yield: 3.62 g, 75%).

Yellow Powder
MS (ESI, m/z): 484 $(M+H)^+$
$^1$H-NMR ($CDCl_3$) δ: 7.36 (1H, s), 7.22 (1H, d, J=4.6), 7.13 (1H, dd, J=2.2, 8.5), 7.04 (1H, d, J=2.2), 6.87 (1H, d, J=8.5), 6.05 (1H, d, J=4.4), 5.03-5.07 (1H, m), 3.94 (3H, s), 3.91 (3H, s), 3.52-3.58 (2H, m), 3.34 (2H, s), 3.25-3.31 (2H, m), 2.67 (4H, q, J=7.1), 2.02-2.07 (2H, m), 1.82-1.90 (2H, m), 1.07 (6H, t, J=7.1)

Production of 1-[5-[(Z)-2-cyano-2-(3,4-dimethoxyphenyl)-vinyl]-thiophen-2-yl]-piperidin-4-yl dimethylamino-acetate hydrochloride (Compound 104)

Ethanol (5 mL) and 12N hydrochloric acid (28 μL) were added to Compound 62 (150 mg), and the mixture was heated for dissolution (external temperature: 40° C.). The solution was returned to room temperature, and allowed to stand overnight. The precipitated crystals were recovered through filtration, and the recovered crystals were recrystallized from isopropanol, to thereby yield the target product (yield: 78.7 mg, 48.6%).

Yellow Powder
MS (ESI, m/z): 456 $(M-HCl+H)^+$.
$^1$H-NMR ($CDCl_3$) δ: 7.37 (1H, s), 7.22 (1H, d, J=4.1), 7.13 (1H, dd, J=2.2, 8.3), 7.04 (1H, d, J=2.2), 6.88 (1H, d, J=8.5), 6.07 (1H, d, J=4.1), 5.13-5.17 (1H, m), 3.94 (3H, s), 3.91 (3H, s), 3.89 (2H, s), 3.55-3.61 (2H, m), 3.25-3.31 (2H, m), 3.02 (6H, s), 2.02-2.12 (2H, m), 1.88-1.96 (2H, m)

Production of 1-[5-[(Z)-2-cyano-2-(3,4-dimethoxyphenyl)-vinyl]-thiophen-2-yl]-piperidin-4-yl diethylamino-acetate hydrochloride (Compound 105)

Isopropanol (10 mL) and 12N hydrochloric acid (59 μL) were added to Compound 103 (338 mg), and the mixture was heated for dissolution (external temperature: 80° C.). The solution was returned to room temperature, and allowed to stand overnight. The precipitated crystals were recovered through filtration, and the recovered crystals were recrystallized from isopropanol, to thereby yield the target product (yield: 254.5 mg, 70.0%).

Yellow Powder
MS (ESI, m/z): 484 $(M-HCl+H)^+$
$^1$H-NMR ($CDCl_3$) δ: 7.38 (1H, s), 7.22 (1H, d, J=4.6), 7.14 (1H, dd, J=2.2, 8.5), 7.05 (1H, d, J=2.2), 6.88 (1H, d, J=8.5), 6.07 (1H, d, J=4.5), 5.10-5.15 (1H, m), 3.95 (3H, s), 3.91 (2H, s), 3.91 (3H, s), 3.54-3.60 (2H, m), 3.39 (4H, q, J=7.3), 3.26-3.32 (2H, m), 2.07-2.12 (2H, m), 1.88-1.96 (2H, m), 1.48 (6H, t, J=7.3)

Example 2

Effect of Overcoming Anticancer Agent Resistance of A549/SN-38-4 Cells

The effect of the compounds of the present invention on BCRP-mediated anticancer agent resistance was studied by use of the human lung cancer A549/SN-38-4 cells (see International Publication WO 2004/069233), which had acquired anticancer agent resistance through BCRP expression. The human lung cancer A549 cells or the A549/SN-38-4 cells were suspended in a Ham's F-12 medium containing 10% FBS, 100 U/mL of penicillin, and 100 μg/mL of streptomycin (10% FBS/Ham's F-12), and the resultant suspension was inoculated into a 96-well microplate ($2 \times 10^3$ cells/50 μL/well), followed by culturing at 5% $CO_2$ and 37° C. overnight. Thereafter, a 10% FBS/Ham's F-12 solution (25 μL) containing each of Compounds 1 to 102 of the present invention and SN-38 was added to each of the wells, followed by culturing at 5% $CO_2$ and 37° C. for 48 hours. After completion of culturing, the number of viable cells was counted by use of a viable cell counting reagent [TetraColor ONE (trademark), product of Seikagaku Corporation] according to the attached instruction manual. Tables 1 to 4 show the effect of each acrylonitrile derivatives in overcoming SN-38 resistance, which is represented by $EC_{50}$. "$EC_{50}$" corresponds to the concentration of an acrylonitrile derivative required for 50% reduction of the relative resistance value. The relative resistance value is obtained by dividing the $IC_{50}$ (i.e., the concentration of an anticancer agent required for 50% inhibition of cell growth) for the A549/SN-38-4 cells by the $IC_{50}$ for the A549 cells (parental cells). The greater the relative resistance value, the higher the level of acquired resistance. The tests have revealed that each of the compounds of the present invention exhibits potent effect of overcoming the SN-38 resistance of the A549/SN-38-4 cells. When each of the acrylonitrile derivatives was solely employed in the absence of SN-38, both A549 cell growth and A549/SN-38-4 cell growth were not affected. This suggests that the acrylonitrile derivative of the present invention inhibits BCRP, and therefore overcomes the anticancer agent resistance of cancer cells or potentiates sensitivity of cancer cells to the anticancer agent.

TABLE 1

| Compound | Effect of overcoming resistance $EC_{50}$ (ng/mL) |
|---|---|
| 1 | 6 |
| 2 | 130 |
| 3 | 32 |
| 4 | 12 |
| 5 | 13 |
| 6 | 10 |
| 7 | 39 |
| 8 | 45 |
| 9 | 46 |
| 10 | 120 |
| 11 | 49 |
| 12 | 58 |
| 13 | 33 |
| 14 | 87 |
| 15 | 200 |
| 19 | 14 |
| 20 | 490 |
| 21 | 20 |
| 22 | 13 |
| 23 | 58 |
| 24 | 34 |
| 25 | 13 |
| 26 | 75 |
| 27 | 200 |
| 28 | 120 |
| 29 | 420 |

TABLE 2

| Compound | Effect of overcoming resistance EC$_{50}$ (ng/mL) |
|---|---|
| 30 | 20 |
| 31 | 37 |
| 32 | 28 |
| 33 | 520 |
| 34 | 58 |
| 35 | 190 |
| 36 | 120 |
| 37 | 120 |
| 38 | 60 |
| 39 | 37 |
| 40 | 75 |
| 41 | 280 |
| 42 | 220 |
| 43 | 160 |
| 44 | 56 |
| 45 | 50 |
| 46 | 100 |
| 47 | 30 |
| 50 | 110 |
| 51 | 510 |
| 54 | 36 |
| 56 | 37 |
| 59 | 61 |
| 61 | 44 |

TABLE 3

| Compound | Effect of overcoming resistance EC$_{50}$ (ng/mL) |
|---|---|
| 62 | 62 |
| 64 | 53 |
| 65 | 11 |
| 66 | 37 |
| 67 | 100 |
| 68 | 11 |
| 69 | 43 |
| 70 | 11 |
| 71 | 13 |
| 72 | 11 |
| 73 | 11 |
| 74 | 21 |
| 75 | 17 |
| 76 | 2 |
| 77 | 110 |
| 78 | 77 |
| 79 | 6 |
| 80 | 19 |
| 82 | 78 |
| 83 | 190 |
| 85 | 230 |
| 86 | 120 |
| 87 | 46 |
| 88 | 70 |

TABLE 4

| Compound | Effect of overcoming resistance EC$_{50}$ (ng/mL) |
|---|---|
| 90 | 460 |
| 91 | 520 |
| 92 | 41 |
| 93 | 280 |
| 95 | 8 |
| 96 | 120 |
| 97 | 78 |
| 98 | 100 |
| 99 | 63 |
| 100 | 12 |
| 101 | 13 |
| 102 | 17 |

Example 3

Effect of Overcoming Anticancer Agent Resistance of Human BCRP Gene-Transduced Mouse Leukemia P388 Cells Mouse leukemia P388 cells or human BCRP gene-transduced P388 cells (P388/BCRP cells) (see JP-A-2003-063989) were suspended in 10% FBS/RPMI1640 containing 2-mercaptethanol (50 µM), and the resultant suspension was added to a 96-well microplate (1×10$^4$ cells/50 µL/well). Thereafter, a solution of each of Compounds 1, 14, 21, 31, 39, and 41 of the present invention and SN-38 in 100 FBS/RPNI1640 (25 µL) was added to each of the wells, followed by culturing at 5% CO$_2$ and 37° C. for 48 hours. After completion of culturing, the number of viable cells was counted by use of TetraColor ONE according to the manufacture's instruction manual. The results are shown in FIG. 1. Each of the tested compounds of the present invention exhibited potent effect of overcoming the SN-38 resistance of the P388/BCRP cells, but did not affect the sensitivity of the P388 cells to SN-38. Use of sole acrylonitrile derivative did not affect proliferation of P388 cells and P388/BCRP cells. This demonstrates that the acrylonitrile derivative of the present invention has BCRP-inhibiting effect.

Example 4

Effect on Multidrug Resistance of Human MDR1 Gene-Transduced

Human Leukemia K562 cells Human leukemia K562 cells or human MDR1 gene-transduced K562 cells (K562/MDR cells) (see Mutat. Res., 1998, 401: 133-141) were suspended in 10% FBS/RPMI1640, and the resultant suspension was added to a 96-well microplate (1×10$^3$ cells/50 µL/well). Thereafter, a solution of paclitaxel and each of the Compounds listed in Tables 5 and 6 in 10% FBS/RPNI1640 (25 µL) was added to each of the wells, followed by culturing at 5% CO$_2$ and 37° C. for 72 hours. After completion of culturing, the number of viable cells was counted by use of TetraColor ONE according to the manufacture's instruction manual. Tables 5 and 6 show the effect of each of the tested acrylonitrile derivatives on multidrug resistance by use of EC$_{50}$. "EC$_{50}$" corresponds to the concentration of an acrylonitrile derivative required for 50% reduction of the relative resistance value. As a result, most of the acrylonitrile derivatives of the present invention do not affect the paclitaxel resistance of the K562/MDR cells. In addition, when the concentration of the acrylonitrile derivative falls within the range employed for the test, the acrylonitrile derivative per se did not affect growth of the K562 cells and the K562/MDR cells. This indicates that the acrylonitrile derivative of the present invention does not act on P-glycoprotein, and has high BCRP specificity.

TABLE 5

| Compound | Effect of overcoming resistance EC$_{50}$ (ng/mL) |
|---|---|
| 1 | >5000 |
| 3 | >5000 |
| 4 | >5000 |
| 5 | >5000 |
| 6 | >5000 |
| 14 | >5000 |
| 17 | >5000 |

TABLE 5-continued

| Compound | Effect of overcoming resistance $EC_{50}$ (ng/mL) |
|---|---|
| 18 | >5000 |
| 19 | >5000 |
| 20 | >5000 |
| 21 | >5000 |
| 25 | >5000 |
| 26 | >5000 |
| 27 | >5000 |
| 28 | >5000 |
| 30 | >5000 |
| 31 | >5000 |
| 32 | >5000 |
| 33 | >5000 |
| 34 | >5000 |
| 36 | >5000 |
| 38 | >5000 |
| 39 | >5000 |
| 40 | >5000 |
| 41 | >5000 |
| 42 | >5000 |

TABLE 6

| Compound | Effect of overcoming resistance $EC_{50}$ (ng/mL) |
|---|---|
| 43 | >5000 |
| 44 | >5000 |
| 45 | >5000 |
| 46 | >5000 |
| 47 | >5000 |
| 52 | >5000 |
| 53 | >5000 |
| 55 | >5000 |
| 56 | >5000 |

Example 5

Effect on Amount of Anticancer Agent Accumulated in BCRP-Expressing Cells

Figure 2:
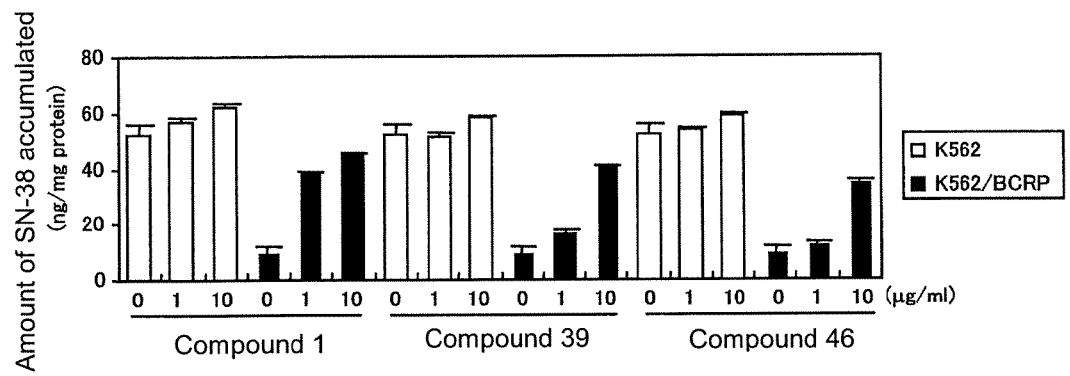
FIG. 2 A graph showing the SN-38 accumulation promoting action of some compounds of the present invention in K562/BCRP cells.

K562 cells or human BCRP gene-transduced K562 cells (K562/BCRP cells) (see JP-A-2003-063989) were suspended in 10% FBS/RPMI1640 (1 mL) (5×10⁶ cells/mL), and SN-38 and each of Compounds 1, 39, and 46 of the present invention (final concentration: 500 ng/mL) were added to the resultant suspension, followed by incubation at 37° C. for 30 minutes. Thereafter, centrifugation was performed (2° C., 1,400×g, 1 min), and the resultant supernatant was removed. Ice-cooled PBS containing 1% BSA was added to the thus-pelletized cells, and the cells were resuspended, followed by centrifugation (2° C., 1,400×g, 1 min) for washing the cells. This washing procedure was performed again, followed by addition of PBS (250 μL) and sonication of the cells. To the resultant cell sonicate, methanol (250 μL) and 10% zinc sulfate solution (10 μL) were added, and the resultant mixture was stirred, followed by centrifugation (2° C., 12,500×g, 5 min) and collection of the supernatant. The thus-collected supernatant was dispensed in a white 96-well microplate for fluorescence intensity measurement (200 μL/well), and then the amount of SN-38 contained in the supernatant was measured by use of a microplate fluorometer [SPECTRA max GEMINI XS (trademark), product of Molecular Devices] (SN-38: excitation wavelength 380 nm, emission wavelength 560 nm), to thereby calculate the amount of intracellular accumulation of SN-38. As is clear from FIG. 2, the acrylonitrile derivative of the present invention increased the amount of accumulation of SN-38 in the K562/BCRP cells. In contrast, the amount of accumulation of SN-38 in the K562 cells (parental cells) in which BCRP had not been expressed was virtually unaffected. This suggests that the acrylonitrile derivative of the present invention inhibits BCRP, and increases the amount of intracellular accumulation of an anticancer agent.

Example 6

Effect of Overcoming Anticancer Agent Resistance In Vivo

Human colon cancer HCT116 cells or BCRP gene-transduced HCT116 cells (HCT116/BCRP cells) (obtained from Dr. Yoshikazu Sugimoto, The Cancer Chemotherapy Center of Japanese Foundation for Cancer Research) were transplanted subcutaneously (3×10⁶ cells/0.1 mL/mouse) to the inguinal region of each of 6-week-old BALB/c male nude mice (5 mice/group). When the tumor volume as estimated from ½ab² (a: longer tumor diameter, b: shorter tumor diameter) reached about 150 to 200 mm³, each of the compounds of the present invention shown in Tables 7 and 8 (6.3, 12.5, or 25 mg/kg/day) and CPT-11 (10 mg/kg/day) were intravenously administered once a day to the mice for seven days. For administration, each of the compounds of the invention was dissolved in physiological saline or in a mixture of ethanol, polyoxyethylene (20) sorbitan monooleate [Tween 80 (trademark), product of Tokyo Kasei Kogyo Co., Ltd.], and 5% glucose (ethanol/Tween 80/5% glucose=5:5:90), and CPT-11 was dissolved in physiological saline. A solvent was solely administered to a control group. On the day 21 from the start of administration, a tumor was extirpated from each mice and weighed, and the tumor growth inhibition ratio IR (%) was derived from the following equation:

Tumor growth inhibition ratio IR(%)=(1−average tumor weight of each administration group/average tumor weight of control group)×100.

The results are shown in Tables 7 and 8. As is clear from Tables 7 and 8, the acrylonitrile derivatives of the present invention inhibit BCRP also in vivo, exhibiting effect of overcoming resistance to anticancer agent.

TABLE 7

| Transplanted cancer cell | Compound | Dose (mg/kg/day) Compound | Dose (mg/kg/day) CPT-11 | Tumor weight (g) Mean ± S.D. | IR (%) |
|---|---|---|---|---|---|
| HCT116/BCRP | 23 | 12.5 | 10 | 1.21 ± 0.17 | 12.3 |
| | | 25 | 10 | 0.71 ± 0.11** | 48.8 |
| | 31 | 12.5 | 10 | 0.74 ± 0.06** | 46.6 |
| | | 25 | 10 | 0.67 ± 0.18** | 51.1 |
| | Solvent | 0 | 10 | 1.20 ± 0.15 | 13.2 |
| | | 0 | 0 | 1.38 ± 0.35 | |
| HCT116 | Solvent | 0 | 10 | 0.37 ± 0.08 | 72.0 |
| | | 0 | 0 | 1.31 ± 0.20 | |

**P < 0.01: significant difference with respect to solvent + CPT-11 (HCT116/BCRP) (Dunnett's test)

TABLE 8

| Transplanted cancer cell | Compound | Dose (mg/kg/day) Compound | Dose (mg/kg/day) CPT-11 | Tumor weight (g) Mean ± S.D. | IR (%) |
|---|---|---|---|---|---|
| HCT116/BCRP | 13 | 12.5 | 10 | 0.87 ± 0.18 | 31.7 |
| | | 25 | 10 | 0.83 ± 0.08* | 35.0 |
| | 14 | 12.5 | 10 | 0.79 ± 0.14* | 37.7 |
| | | 25 | 10 | 0.70 ± 0.10** | 45.1 |
| | 32 | 6.3 | 10 | 0.75 ± 0.24** | 40.8 |
| | | 12.5 | 10 | 0.52 ± 0.11** | 59.0 |

TABLE 8-continued

| Transplanted cancer cell | Compound | Dose (mg/kg/day) Compound | Dose (mg/kg/day) CPT-11 | Tumor weight (g) Mean ± S.D. | IR (%) |
|---|---|---|---|---|---|
| | 46 | 12.5 | 10 | 0.79 ± 0.21* | 37.7 |
| | | 25 | 10 | 0.67 ± 0.07** | 47.7 |
| | Solvent | 0 | 10 | 1.10 ± 0.10 | 13.3 |
| | | 0 | 0 | 1.27 ± 0.15 | |

*P < 0.05,
**P < 0.01: significant difference with respect to solvent + CPT-11 (HCT116/BCRP) (Dunnett's test)

Example 7

The following ingredients were mixed and tableted.

TABLE 9

| Compound 1 | 100 mg |
|---|---|
| Lactose | 100 mg |
| Potato starch | 39 mg |
| Microcrystalline cellulose | 30 mg |
| Synthetic aluminum silicate | 30 mg |
| Calcium stearate | 1 mg |
| Total (one tablet) | 300 mg |

The invention claimed is:
1. An acrylonitrile derivative or a salt thereof selected from the group consisting of:
(Z)-2-(3,4-dimethoxy-phenyl)-3-(5-nitro-thiophen-2-yl)-acrylonitrile,
(Z)-3-(5-bromo-thiophen-2-yl)-2-(3,4-dimethoxy-phenyl)-acrylonitrile,
(Z)-3-(5-amino-thiophen-2-yl)-2-(3,4-dimethoxy-phenyl)-acrylonitrile,
(Z)-2-(3,4-dimethoxy-phenyl)-3-(5-piperidin-1-yl-thiophen-2-yl)-acrylonitrile,
(Z)-2-(3,4-dimethoxy-phenyl)-3-(5-morpholin-4-yl-thiophen-2-yl)-acrylonitrile,
(Z)-2-(3,4-dimethoxy-phenyl)-3-[5-(4-hydroxy-piperidin-1-yl)-thiophen-2-yl]-acrylonitrile,
(Z)-2-(3,4-dimethoxy-phenyl)-3-{5-[(2-hydroxy-ethyl)-methyl-amino]-thiophen-2-yl}-acrylonitrile,
(Z)-2-(3,4-dimethoxy-phenyl)-3-[5-(4-methyl-piperazin-1-yl)-thiophen-2-yl]-acrylonitrile,
(Z)-2-(3,4-dimethoxy-phenyl)-3-{5-[4-(2-hydroxy-ethyl)-piperazin-1-yl]-thiophen-2-yl}-acrylonitrile,
mono-(1-{5-[(Z)-2-cyano-2-(3,4-dimethoxy-phenyl)-vinyl]-thiophen-2-yl}-piperidin-4-yl)phosphate,
mono-(1-{5-[(Z)-2-cyano-2-(3,4-dimethoxy-phenyl)-vinyl]-thiophen-2-yl}-piperidin-4-yl)succinate,
(Z)-2-(3,4-dimethoxy-phenyl)-3-(5-nitro-furan-2-yl)-acrylonitrile,
(Z)-2-(3,4-dimethoxy-phenyl)-3-(5-hydroxy-methyl-furan-2-yl)-acrylonitrile,
(Z)-2-(3,4-dimethoxy-phenyl)-3-[5-(3-nitro-phenyl)-furan-2-yl]-acrylonitrile,
(Z)-3-[5-(3-amino-phenyl)-furan-2-yl]-2-(3,4-dimethoxy-phenyl)-acrylonitrile,
(Z)-2-(3,4-dimethoxy-phenyl)-3-(5-piperidin-1-yl-furan-2-yl)-acrylonitrile,
(Z)-2-(3,4-dimethoxy-phenyl)-3-(5-morpholin-4-yl-furan-2-yl)-acrylonitrile,
(Z)-2-(3,4-dimethoxy-phenyl)-3-[5-(4-hydroxy-piperidin-1-yl)-furan-2-yl]-acrylonitrile,
(Z)-2-(3,4-dimethoxy-phenyl)-3-[5-(4-methyl-piperazin-1-yl)-furan-2-yl]-acrylonitrile,
(Z)-2-(3,4-dimethoxy-phenyl)-3-[(5-[4-(2-hydroxy-ethyl)-piperazin-1-yl]-furan-2-yl]-acrylonitrile,
(Z)-2-(3,4-dimethoxy-phenyl)-3-pyridin-4-yl-acrylonitrile N-oxide,
(Z)-2-(3,4-dimethoxy-phenyl)-3-(6-methoxy-pyridin-3-yl)-acrylonitrile,
(Z)-2-(3,4-dimethoxy-phenyl)-3-(1H-pyrrol-2-yl)-acrylonitrile,
(Z)-2-(3,4-dimethoxy-phenyl)-3-(3H-imidazol-4-yl)-acrylonitrile,
(Z)-3-(3-benzyl-2-methylsulfanyl-3H-imidazol-4-yl)-2-(3,4-dimethoxy-phenyl)-acrylonitrile,
(Z)-2-(3,4-dimethoxy-phenyl)-3-(4-methyl-2-phenyl-thiazol-5-yl)-acrylonitrile,
mono-(1-{5-[(Z)-2-cyano-2-(3,4-dimethoxy-phenyl)-vinyl]-furan-2-yl}-piperidin-4-yl)succinate,
mono-(1-{5-[(Z)-2-cyano-2-(3,4-dimethoxy-phenyl)-vinyl]-furan-2-yl}-piperidin-4-yl)phosphate,
(Z)-3-(5-bromo-furan-2-yl)-2-(3,4-dimethoxy-phenyl)-acrylonitrile,
(Z)-3-(3,4-dimethoxy-phenyl)-2-thiophen-3-yl-acrylonitrile,
1-[5-[(Z)-2-cyano-2-(3,4-dimethoxy-phenyl)-vinyl]-thiophen-2-yl]-piperidin-4-yl N-(3-diethylamino-propyl)-succinamate,
1-[5-[(Z)-2-cyano-2-(3,4-dimethoxy-phenyl)-vinyl]-thiophen-2-yl]-piperidin-4-yl dimethylamino-acetate,
1-[5-[(Z)-2-cyano-2-(3,4-dimethoxy-phenyl)-vinyl]-thiophen-2-yl]-piperidin-4-yl [1,4']bipiperidinyl-1'-carboxylate,
1-[5-[(Z)-2-cyano-2-(3,4-dimethoxy-phenyl)-vinyl]-thiophen-2-yl]-piperidin-4-yl 4-[1,4']bipiperidinyl-1'-yl-4-oxo-butylate,
(Z)-3-benzo[b]thiophen-3-yl-2-(3,4-dimethoxy-phenyl)-acrylonitrile,
(Z)-2-(3,4-dimethoxy-phenyl)-3-(1-methyl-1H-benzimidazol-2-yl)-acrylonitrile,
(Z)-2-(3,4-dimethoxy-phenyl)-3-(1-methyl-1H-indol-3-yl)-acrylonitrile,
(Z)-3-(2-chloro-quinolin-3-yl)-2-(3,4-dimethoxy-phenyl)-acrylonitrile,
(Z)-2-benzofuran-3-yl-3-(3,4-dimethoxy-phenyl)-acrylonitrile,
(Z)-3-(2-chloro-6-methoxy-quinolin-3-yl)-2-(3,4-dimethoxy-phenyl)-acrylonitrile,
(E)-2-benzothiazol-2-yl-3-(3,4-dimethoxy-phenyl)-acrylonitrile,
(Z)-3-(2,3-dihydro-benzofuran-5-yl)-2-(3,4-dimethoxy-phenyl)-acrylonitrile,
(Z)-2-(3,4-dimethoxy-phenyl)-3-[5-(4-fluoro-phenyl)-isoxazol-3-yl]-acrylonitrile,
(Z)-2-(3,4-dimethoxy-phenyl)-3-[5-(4-methoxy-phenyl)-isoxazol-3-yl]-acrylonitrile,
(Z)-3-(2-chloro-6-methoxy-quinolin-3-yl)-2-pyridin-2-yl-acrylonitrile,
(Z)-3-(2-chloro-6-methoxy-quinolin-3-yl)-2-pyridin-3-yl-acrylonitrile,
(E)-3-(2-chloro-6-methoxy-quinolin-3-yl)-2-thiophen-2-yl-acrylonitrile,
(Z)-3-(2-chloro-6-methoxy-quinolin-3-yl)-2-thiophen-3-yl-acrylonitrile,
(E)-2-benzotriazol-1-yl-3-(2-chloro-6-methoxy-quinolin-3-yl)-acrylonitrile,
(Z)-2-pyridin-2-yl-3-quinolin-4-yl-acrylonitrile,
(E)-3-quinolin-4-yl-2-thiophen-2-yl-acrylonitrile,

(Z)-3-quinolin-4-yl-2-thiophen-3-yl-acrylonitrile,
(E)-3-benzo[b]thiophen-3-yl-2-benzothiazol-2-yl-acrylonitrile,
(Z)-3-benzofuran-2-yl-2-benzofuran-3-yl-acrylonitrile,
(E)-2-benzothiazol-2-yl-3-(1-methyl-1H-indol-3-yl)-acrylonitrile,
(Z)-3-(10-chloro-anthracen-9-yl)-2-(3,4-dimethoxy-phenyl)-acrylonitrile,
1-[5-[(Z)-2-cyano-2-(3,4-dimethoxy-phenyl)-vinyl]-thiophen-2-yl]-piperidin-4-yl diethylamino-acetate,
1-[5-[(Z)-2-cyano-2-(3,4-dimethoxy-phenyl)-vinyl]-thiophen-2-yl]-piperidin-4-yl diethyl-carbamate,
1-[5-[(Z)-2-cyano-2-(3,4-dimethoxy-phenyl)-vinyl]-thiophen-2-yl]-piperidin-4-yl N-(2-diethylamino-ethyl)-N-methyl-succinamate, and
1-[5-[(Z)-2-cyano-2-(3,4-dimethoxy-phenyl)-vinyl]-thiophen-2-yl]-piperidin-4-yl N-(4-diethylamino-phenyl)-succinamate; or
a salt thereof.

2. A acrylonitrile derivative or a salt thereof of selected from the group consisting of:
(Z)-2-(3,4-dimethoxy-phenyl)-3-(5-nitro-thiophen-2-yl)-acrylonitrile,
(Z)-3-(5-bromo-thiophen-2-yl)-2-(3,4-dimethoxy-phenyl)-acrylonitrile,
(Z)-3-(5-amino-thiophen-2-yl)-2-(3,4-dimethoxy-phenyl)-acrylonitrile,
(Z)-2-(3,4-dimethoxy-phenyl)-3-(5-piperidin-1-yl-thiophen-2-yl)-acrylonitrile,
(Z)-2-(3,4-dimethoxy-phenyl)-3-(5-morpholin-4-yl-thiophen-2-yl)-acrylonitrile,
(Z)-2-(3,4-dimethoxy-phenyl)-3-[5-(4-hydroxy-piperidin-1-yl)-thiophen-2-yl]-acrylonitrile,
(Z)-2-(3,4-dimethoxy-phenyl)-3-{5-[(2-hydroxy-ethyl)-methyl-amino]-thiophen-2-yl}-acrylonitrile,
(Z)-2-(3,4-dimethoxy-phenyl)-3-[5-(4-methyl-piperazin-1-yl)-thiophen-2-yl]-acrylonitrile,
(Z)-2-(3,4-dimethoxy-phenyl)-3-{5-[4-(2-hydroxy-ethyl)-piperazin-1-yl]-thiophen-2-yl}-acrylonitrile,
mono-(1-{5-[(Z)-2-cyano-2-(3,4-dimethoxy-phenyl)-vinyl]-thiophen-2-yl}-piperidin-4-yl)phosphate,
mono-(1-{5-[(Z)-2-cyano-2-(3,4-dimethoxy-phenyl)-vinyl]-thiophen-2-yl}-piperidin-4-yl)succinate,
(Z)-2-(3,4-dimethoxy-phenyl)-3-(5-nitro-furan-2-yl)-acrylonitrile,
(Z)-2-(3,4-dimethoxy-phenyl)-3-(5-hydroxy-methyl-furan-2-yl)-acrylonitrile,
(Z)-2-(3,4-dimethoxy-phenyl)-3-[5-(3-nitro-phenyl)-furan-2-yl]-acrylonitrile,
(Z)-3-[5-(3-amino-phenyl)-furan-2-yl]-2-(3,4-dimethoxy-phenyl)-acrylonitrile,
(Z)-2-(3,4-dimethoxy-phenyl)-3-(5-piperidin-1-yl-furan-2-yl)-acrylonitrile,
(Z)-2-(3,4-dimethoxy-phenyl)-3-(5-morpholin-4-yl-furan-2-yl)-acrylonitrile,
(Z)-2-(3,4-dimethoxy-phenyl)-3-[5-(4-hydroxy-piperidin-1-yl)-furan-2-yl]-acrylonitrile,
(Z)-2-(3,4-dimethoxy-phenyl)-3-[5-(4-methyl-piperazin-1-yl)-furan-2-yl]-acrylonitrile,
(Z)-2-(3,4-dimethoxy-phenyl)-3-{5-[4-(2-hydroxy-ethyl)-piperazin-1-yl]-furan-2-yl}-acrylonitrile,
(Z)-2-(3,4-dimethoxy-phenyl)-3-(1H-pyrrol-2-yl)-acrylonitrile,
(Z)-2-(3,4-dimethoxy-phenyl)-3-(3H-imidazol-4-yl)-acrylonitrile,
(Z)-3-(3-benzyl-2-methylsulfanyl-3H-imidazol-4-yl)-2-(3,4-dimethoxy-phenyl)-acrylonitrile,
(Z)-2-(3,4-dimethoxy-phenyl)-3-(4-methyl-2-phenyl-thiazol-5-yl)-acrylonitrile,
mono-(1-{5-[(Z)-2-cyano-2-(3,4-dimethoxy-phenyl)-vinyl]-furan-2-yl}-piperidin-4-yl)succinate,
mono-(1-{5-[(Z)-2-cyano-2-(3,4-dimethoxy-phenyl)-vinyl]-furan-2-yl}-piperidin-4-yl)phosphate,
(Z)-3-(5-bromo-furan-2-yl)-2-(3,4-dimethoxy-phenyl)-acrylonitrile,
(Z)-3-(3,4-dimethoxy-phenyl)-2-thiophen-3-yl-acrylonitrile,
1-[5-[(Z)-2-cyano-2-(3,4-dimethoxy-phenyl)-vinyl]-thiophen-2-yl]-piperidin-4-yl N\-(3-diethylamino-propyl)-succinamate,
1-[5-[(Z)-2-cyano-2-(3,4-dimethoxy-phenyl)-vinyl]-thiophen-2-yl]-piperidin-4-yl dimethylamino-acetate,
1-[5-[(Z)-2-cyano-2-(3,4-dimethoxy-phenyl)-vinyl]-thiophen-2-yl]-piperidin-4-yl [1,4']bipiperidinyl-1'-carboxylate,
1-[5-[(Z)-2-cyano-2-(3,4-dimethoxy-phenyl)-vinyl]-thiophen-2-yl]-piperidin-4-yl 4-[1,4']bipiperidinyl-1'-yl-4-oxo-butylate,
(Z)-3-benzo[b]thiophen-3-yl-2-(3,4-dimethoxy-phenyl)-acrylonitrile,
(Z)-2-(3,4-dimethoxy-phenyl)-3-(1-methyl-1H-benzimidazol-2-yl)-acrylonitrile,
(Z)-2-(3,4-dimethoxy-phenyl)-3-(1-methyl-1H-indol-3-yl)-acrylonitrile,
(Z)-3-(2-chloro-quinolin-3-yl)-2-(3,4-dimethoxy-phenyl)-acrylonitrile,
(Z)-2-benzofuran-3-yl-3-(3,4-dimethoxy-phenyl)-acrylonitrile,
(Z)-3-(2-choro-6-methoxy-quinolin-3-yl)-2-(3,4-dimethoxy-phenyl)-acrylonitrile,
(E)-2-benzothiazol-2-yl-3-(3,4-dimethoxy-phenyl)-acrylonitrile,
(Z)-3-(2,3-dihydro-benzofuran-5-yl)-2-(3,4-dimethoxy-phenyl)-acrylonitrile,
(Z)-2-(3,4-dimethoxy-phenyl)-3-[5-(4-fluoro-phenyl)-isoxazol-3-yl]-acrylonitrile,
(Z)-2-(3,4-dimethoxy-phenyl)-3-[5-(4-methoxy-phenyl)-isoxazol-3-yl]-acrylonitrile,
(Z)-3-(2-chloro-6-methoxy-quinolin-3-yl)-2-pyridin-2-yl-acrylonitrile,
(Z)-3-(2-chloro-6-methoxy-quinolin-3-yl)-2-pyridin-3-yl-acrylonitrile,
(E)-3-(2-chloro-6-methoxy-quinolin-3-yl)-2-thiophen-2-yl-acrylonitrile,
(Z)-3-(2-chloro-6-methoxy-quinolin-3-yl)-2-thiophen-3-yl-acrylonitrile,
(E)-2-benzotriazol-1-yl-3-(2-chloro-6-methoxy-quinolin-3-yl)-acrylonitrile,
(Z)-2-pyridin-2-yl-3-quinolin-4-yl-acrylonitrile,
(E)-3-quinolin-4-yl-2-thiophen-2-yl-acrylonitrile,
(Z)-3-quinolin-4-yl-2-thiophen-3-yl-acrylonitrile,
(E)-3-benzo[b]thiophen-3-yl-2-benzothiazol-2-yl-acrylonitrile,
(Z)-3-benzofuran-2-yl-2-benzofuran-3-yl-acrylonitrile,
(E)-2-benzothiazol-2-yl-3-(1-methyl-H-indol-3-yl)-acrylonitrile,
(Z)-3-(10-chloro-anthracen-9-yl)-2-(3,4-dimethoxy-phenyl)-acrylonitrile,
1-[5-[(Z)-2-cyano-2-(3,4-dimethoxy-phenyl)-vinyl]-thiophen-2-yl]-piperidin-4-yl diethylamino-acetate,
1-[5-[(Z)-2-cyano-2-(3,4-dimethoxy-phenyl)-vinyl]-thiophen-2-yl]-piperidin-4-yl diethyl-carbamate,
1-[5-[(Z)-2-cyano-2-(3,4-dimethoxy-phenyl)-vinyl]-thiophen-2-yl]-piperidin-4-yl N-(2-diethylamino-ethyl)-N-methyl-succinamate, and 1-[5-[(Z)-2-cyano-2-(3,4-dimethoxy-phenyl)-vinyl]-thiophen-2-yl]-piperidin-4-yl N-(4-diethylamino-phenyl)-succinamate; or
a salt thereof.

3. The acrylonitrile derivative or a salt thereof of claim 2 selected from the group consisting of:
(Z)-3-benzo[b]thiophen-3-yl-2-(3,4-dimethoxy-phenyl)-acrylonitrile,
(Z)-2-(3,4-dimethoxy-phenyl)-3-(1-methyl-1H-benzimidazol-2-yl)-acrylonitrile,
(Z)-2-(3,4-dimethoxy-phenyl)-3-(1-methyl-1H-indol-3-yl)-acrylonitrile,
(Z)-3-(2-chloro-quinolin-3-yl)-2-(3,4-dimethoxy-phenyl)-acrylonitrile,
(Z)-2-benzofuran-3-yl-3-(3,4-dimethoxy-phenyl)-acrylonitrile,
(Z)-3-(2-choro-6-methoxy-quinolin-3-yl)-2-(3,4-dimethoxy-phenyl)-acrylonitrile,
(E)-2-benzothiazol-2-yl-3-(3,4-dimethoxy-phenyl)-acrylonitrile,
(Z)-3-(2,3-dihydro-benzofuran-5-yl)-2-(3,4-dimethoxy-phenyl)-acrylonitrile; or
a salt thereof.

4. The acrylonitrile derivative or a salt thereof of claim 2 selected from the group consisting of:
(Z)-3-(2-chloro-6-methoxy-quinolin-3-yl)-2-pyridin-2-yl-acrylonitrile,
(Z)-3-(2-chloro-6-methoxy-quinolin-3-yl)-2-pyridin-3-yl-acrylonitrile,
(E)-3-(2-chloro-6-methoxy-quinolin-3-yl)-2-thiophen-2-yl-acrylonitrile,
(Z)-3-(2-chloro-6-methoxy-quinolin-3-yl)-2-thiophen-3-yl-acrylonitrile,
(E)-2-benzotriazol-1-yl-3-(2-chloro-6-methoxy-quinolin-3-yl)-acrylonitrile; or
a salt thereof.

5. The acrylonitrile derivative or a salt thereof of claim 2 selected from the group consisting of:
(Z)-2-pyridin-2-yl-3-quinolin-4-yl-acrylonitrile,
(E)-3-quinolin-4-yl-2-thiophen-2-yl-acrylonitrile,
(Z)-3-quinolin-4-yl-2-thiophen-3-yl-acrylonitrile; or
a salt thereof.

6. The acrylonitrile derivative or a salt thereof of claim 2 selected from the group consisting of:
(E)-3-benzo[b]thiophen-3-yl-2-benzothiazol-2-yl-acrylonitrile,
(Z)-3-benzofuran-2-yl-2-benzofuran-3-yl-acrylonitrile,
(E)-2-benzothiazol-2-yl-3-(1-methyl-H-indol-3-yl)-acrylonitrile; or
a salt thereof.

7. The acrylonitrile derivative or a salt thereof of claim 2 selected from the group consisting of:
1-[5-[(Z)-2-cyano-2-(3,4-dimethoxy-phenyl)-vinyl]-thiophen-2-yl]-piperidin-4-yl diethylamino-acetate,
1-[5-[(Z)-2-cyano-2-(3,4-dimethoxy-phenyl)-vinyl]-thiophen-2-yl]-piperidin-4-yl diethyl-carbamate,
1-[5-[(Z)-2-cyano-2-(3,4-dimethoxy-phenyl)-vinyl]-thiophen-2-yl]-piperidin-4-yl N-(2-diethylamino-ethyl)-N-methyl-succinamate, and
1-[5-[(Z)-2-cyano-2-(3,4-dimethoxy-phenyl)-vinyl]-thiophen-2-yl]-piperidin-4-yl N-(4-diethylamino-phenyl)-succinamate; or
a salt thereof.

8. The acrylonitrile derivative or a salt thereof of claim 2 comprising
(Z)-2-(3,4-dimethoxy-phenyl)-3-[5-(4-hydroxy-piperidin-1-yl)-thiophen-2-yl]-acrylonitrile; or a salt thereof.

9. The acrylonitrile derivative or a salt thereof of claim 2 comprising
1-[5-[(Z)-2-cyano-2-(3,4-dimethoxy-phenyl)-vinyl]-thiophen-2-yl]-piperidin-4-yl diethylamino-acetate; or
a salt thereof.

10. A drug composition comprising at last one a compound or a salt thereof of claim 1.

11. A pharmaceutical composition comprising a compound or a salt thereof as recited in claim 1 and a pharmaceutically acceptable carrier.

12. A pharmaceutical composition comprising:
an acrylonitrile derivative or a salt thereof as recited in claim 1, and
an anticancer agent which serves as a BCRP (breast cancer resistance protein) substrate.

* * * * *